(12) United States Patent
Linnen et al.

(10) Patent No.: US 7,927,840 B2
(45) Date of Patent: Apr. 19, 2011

(54) METHOD FOR DETECTING WEST NILE VIRUS NUCLEIC ACIDS IN THE 3' NON-CODING REGION

(75) Inventors: Jeffrey M. Linnen, Poway, CA (US); Reinhold B. Pollner, San Diego, CA (US)

(73) Assignee: Gen Probe Incorporated, San Diego, CA (US)

( * ) Notice: Subject to any disclaimer, the term of this patent is extended or adjusted under 35 U.S.C. 154(b) by 0 days.

(21) Appl. No.: 11/932,012

(22) Filed: Oct. 31, 2007

(65) Prior Publication Data

US 2008/0108055 A1   May 8, 2008

Related U.S. Application Data

(63) Continuation of application No. 11/519,359, filed on Sep. 11, 2006, now Pat. No. 7,732,169.

(51) Int. Cl.
    *C12Q 1/68* (2006.01)
    *C12P 19/34* (2006.01)

(52) U.S. Cl. .......................... 435/91.2; 435/6

(58) Field of Classification Search .................. None
     See application file for complete search history.

(56) References Cited

U.S. PATENT DOCUMENTS

| | | | |
|---|---|---|---|
| 5,399,491 A | 3/1995 | Kacian et al. | |
| 5,472,841 A | 12/1995 | Jayasena et al. | |
| 5,639,604 A | 6/1997 | Arnold, Jr. et al. | |
| 5,734,034 A | 3/1998 | Jayasena et al. | |
| 5,760,207 A | 6/1998 | Kinzler et al. | |
| 5,770,356 A | 6/1998 | Light, II et al. | |
| 5,837,447 A | 11/1998 | Gorski | |
| 5,888,779 A | 3/1999 | Kacian et al. | |
| 5,939,254 A | 8/1999 | Ennis et al. | |
| 5,962,332 A | 10/1999 | Singer et al. | |
| 6,056,957 A | 5/2000 | Chou et al. | |
| 6,087,331 A | 7/2000 | Newman et al. | |
| 6,127,116 A | 10/2000 | Rice et al. | |
| 6,172,039 B1 | 1/2001 | De Angelo et al. | |
| 6,197,500 B1 | 3/2001 | Sutherland et al. | |
| 6,218,150 B1 | 4/2001 | Uemori et al. | |
| 6,242,576 B1 | 6/2001 | Sutherland et al. | |
| 6,251,607 B1 | 6/2001 | Tsen et al. | |
| 6,251,632 B1 | 6/2001 | Lillicrap et al. | |
| 6,284,249 B1 | 9/2001 | Barban | |
| 6,309,645 B1 | 10/2001 | Rhode et al. | |
| 6,312,892 B1 | 11/2001 | Barany et al. | |
| 6,316,200 B1 | 11/2001 | Nadeau et al. | |
| 6,329,144 B1 | 12/2001 | Kubista et al. | |
| 6,333,158 B1 | 12/2001 | Uemori et al. | |
| 6,337,070 B1 | 1/2002 | Okuno et al. | |
| 6,423,511 B1 | 7/2002 | Nakamura et al. | |
| 6,448,003 B1 | 9/2002 | Guida et al. | |
| 6,451,982 B1 | 9/2002 | Chou et al. | |
| 6,465,438 B1 | 10/2002 | Schoor et al. | |
| 6,538,123 B2 | 3/2003 | Barban | |
| 6,586,229 B1 | 7/2003 | Ben-Bassat et al. | |
| 6,586,244 B2 | 7/2003 | Reinhard et al. | |
| 2002/0198144 A1 | 12/2002 | Wong et al. | |
| 2003/0008277 A1 | 1/2003 | Escriou et al. | |
| 2003/0064074 A1 | 4/2003 | Chang et al. | |
| 2003/0082547 A1 * | 5/2003 | Ewing et al. | 435/6 |
| 2003/0087847 A1 | 5/2003 | Jarvis et al. | |
| 2003/0093819 A1 | 5/2003 | D'Andrea et al. | |
| 2003/0096239 A1 | 5/2003 | Gunderson et al. | |
| 2003/0101476 A1 | 5/2003 | Short et al. | |
| 2003/0109007 A1 | 6/2003 | Koizumi et al. | |
| 2003/0188326 A1 | 10/2003 | D'Andrea et al. | |
| 2003/0194694 A1 | 10/2003 | Kawaoka | |
| 2003/0207380 A1 | 11/2003 | Saito et al. | |
| 2004/0229261 A1 | 11/2004 | Young | |

FOREIGN PATENT DOCUMENTS

| | | |
|---|---|---|
| EP | 0 388 232 A1 | 3/1990 |
| EP | 0 318 216 B2 | 8/2001 |
| EP | 1 178 116 A1 | 2/2002 |
| WO | WO89/04669 A1 | 6/1989 |
| WO | WO98/37211 A1 | 8/1998 |
| WO | WO00/66149 A1 | 11/2000 |
| WO | WO00/75338 A2 | 12/2000 |
| WO | WO01/21807 A1 | 3/2001 |
| WO | WO01/38360 A2 | 3/2001 |
| WO | WO01/34646 A2 | 5/2001 |
| WO | WO01/34647 A2 | 5/2001 |
| WO | WO01/34801 A2 | 5/2001 |
| WO | WO01/48245 A2 | 7/2001 |
| WO | WO01/51659 A2 | 7/2001 |
| WO | WO01/62298 A3 | 8/2001 |
| WO | 01/79546 A1 | 10/2001 |
| WO | WO01/83816 A2 | 11/2001 |
| WO | WO01/90337 A2 | 11/2001 |
| WO | WO02/02599 A2 | 1/2002 |
| WO | WO02/06463 A2 | 1/2002 |
| WO | WO02/12290 A2 | 2/2002 |
| WO | 02/068637 A1 | 9/2002 |
| WO | WO 02068637 A2 * | 9/2002 |
| WO | WO03/048184 A2 | 6/2003 |
| WO | WO 2004036190 A2 * | 4/2004 |
| WO | WO2004/042042 A1 | 5/2004 |
| WO | WO2004/055159 A2 | 7/2004 |
| WO | WO2004/092412 A2 | 10/2004 |

OTHER PUBLICATIONS

Hadfield et al., "Detection of West Nile virus in mosquitos by RT-PCR," Molecular and Cellular Probes, 2001, vol. 15, pp. 147-150.*
GenBank Accession No. AF458343, available Jul. 2002, Beasley et al.*
Briese et al., "Detection of West Nile virus sequences in cerebrospinal fluid," The Lancet, May 2000, vol. 355, pp. 1614-1615.*
Buck et al., "Design Strategies and Performance of Custom DNA Sequencing Primers," BioTechniques, Sep. 1999, vol. 27, pp. 528-536.*
Beasley et al., "Mouse Neuroinvasive Phenotype of West Nile Virus Strains Varies Depending upon Virus Genotype,", Virol., 2002, 296:17-23, Elsevier Science, USA.
Chang et al., "An Integrated Target Sequence and Signal Amplifictiion Assay, Reverse Transcriptase-PCR-Enzyme-Linked Immunosorbent Assay, To Detect and Characterize Flaviviruses,", J. Clin. Microbiol., Feb. 1994, 32(2):477-483, ASM, USA.

(Continued)

*Primary Examiner* — Young J Kim
(74) *Attorney, Agent, or Firm* — Michael J. Gilly

(57) ABSTRACT

Compositions, methods and kits for detecting flavivirus nucleic acids. Particularly described are methods for detecting West Nile virus nucleic acids in the 3' non-coding region.

10 Claims, 3 Drawing Sheets

OTHER PUBLICATIONS

Database GenBank, Accession AF404753, "West Nile Virus isolate WN MD 2000-crow265, complete genome," Jul. 2002, 298(1):96-105.

Database GenBank, Accession No. AF458348, "West Nile virus strain IbAn7019 nonstructural protein 5 gene, partial cds," Jul. 2002, 296(1):17-23.

Database GenBank, Accession No. AF458355, "West Nile virus strain Egypt101 nonstructural protein 5 gene, partial cds," Jul. 2002, 296(1):17-23.

Database GenBank, Accession No. AF481864, "West Nile virus strain IS-98 STD, complete genome," 298(1):392-397, May 2002.

Lanciotti et al., "Complete Genome Sequences and Phylogenetic Analysis of West Nile Virus Strains Isolated from the United States, Europe, and the Middle East," Virol., 2002, 298:96-105, Elsevier Science, USA.

Malkinson et al., "Introduction of *West Nile* virus in the Middle East by Migrating White Storks," Emerg. Infect. Dis., Apr. 2002, 8(4):392-397, CDC, USA.

Porter et al., "Detection of West Nile Virus by the Polymerase Chain Reaction and Analysis of Nucleotide Sequence Variation," Am. J. Trop. Med. Hyg., 1993, 48(3):440-446, American Society of Tropical Medicine and Hygiene, USA.

Tanaka, "Rapid identification of flavivirus using the polymerase chain reaction," J. Virol. Methods, 1993, 41:311-322, Elsevier Science Publishers B.V., Netherlands.

Brinton et al., "The 3'-Nucleotides of Flavivirus Genomic RNA Form a Conserved Secondary Structure," Virology, 1986, 153:113-121, Academic Press, Inc., USA.

Lanciotti et al., "Origin of the West Nile Virus Responsible for an Outbreak of Encephalitis in the Northeastern United States," Science, 1999, 286(5448):2333-2337, American Association for the Advancement of Science Washington, DC, USA.

Database Genbank, Accession No. AF196536, "West Nile virus isolate ArA1Dj polyprotein gene, partial cds.," Mar. 2002, 7(4):697-705.

Database Genbank, Accession No. AF196835, "West Nile virus strain NY99-flamingo382-99, complete genome," Dec. 2000, 286(5448):2333-2337.

Sherret et al., "The Relationships between West Nile and Kunjin Viruses," Emerg. Infect. Dis., 7(4):697-705, National Center for Infectious DiseasesCenters for Disease Control, Atlanta, GA, USA.

Scaramozzino et al., "Comparison of Flavivirus Universal Primer Pairs and Development of a Rapid, Highly Sensitive Heminested Reverse Transcription-PCT Assay for Detection of Flavviruses Targeted to a Conserved Region of the NS5 Gene Sequences," J. Clin. Microbio., 2001, 39(5):1922-1927, ASM, USA.

Briese et al., "Detection of West Nile Virus Sequences in Cerebrospinal Fluid," The Lancet, 2000, 355 (9215):1614-1615, Lancet Limited, GB.

Database GenBank, Accession No. AF481864, "West Nile virus strain IS-98 STD, complete genome," May 21, 2002, 298(1):392-397.

Sherret et al., "The Relationships between West Nile and Kunjin Viruses," Emerg. Infect. Dis., Aug. 2001, 7 (4):697-705, National Center for Infectious DiseasesCenters for Disease Control, Atlanta, GA, USA.

Shi et al., "High-Throughput Detection of West Nile Virus RNA," J. Clin. Microbiol., Apr. 2001, 39(4):1264-1271, Am. Society for Microbiology, USA.

Pierre et al., "Identification of mosquito-borne flavivirus sequences using universal primers and reverse transcription/polymerase chain reaction," Res. Virol., 1994, 145:93-104, Institut Pasteur/Elsevier, France.

* cited by examiner

SEQUENCE LISTING

<160> NUMBER OF SEQ ID NOS: 196

<210> SEQ ID NO 1
<211> LENGTH: 58
<212> TYPE: DNA
<213> ORGANISM: West Nile Virus

<400> SEQUENCE: 1
caattaacac agtgcgagct gtttcttagc acgaagatct cgatgtctaa gaaaccag          58

<210> SEQ ID NO 2
<211> LENGTH: 26
<212> TYPE: DNA
<213> ORGANISM: West Nile Virus

<400> SEQUENCE: 2
gaagatctcg atgtctaaga aaccag          26

<210> SEQ ID NO 3
<211> LENGTH: 27
<212> TYPE: DNA
<213> ORGANISM: West Nile Virus

<400> SEQUENCE: 3
caattaacac agtgcgagct gtttctt          27

<210> SEQ ID NO 4
<211> LENGTH: 24
<212> TYPE: DNA
<213> ORGANISM: West Nile Virus

<400> SEQUENCE: 4
caattaacac agtgcgagct gttt          24

<210> SEQ ID NO 5
<211> LENGTH: 24
<212> TYPE: DNA
<213> ORGANISM: West Nile Virus
<220> FEATURE:
<221> NAME/KEY: modified_base
<222> LOCATION: (11)...(11)
<223> OTHER INFORMATION: I

<400> SEQUENCE: 5
caattaacac ngtgcgagct gttt          24

<210> SEQ ID NO 6
<211> LENGTH: 23
<212> TYPE: DNA
<213> ORGANISM: West Nile Virus

<400> SEQUENCE: 6
taacacagtg cgagctgttt ctt          23

<210> SEQ ID NO 7
<211> LENGTH: 23
<212> TYPE: DNA
<213> ORGANISM: West Nile Virus
<220> FEATURE:
<221> NAME/KEY: modified_base
<222> LOCATION: (7)...(7)
<223> OTHER INFORMATION: I

<400> SEQUENCE: 7

-continued

```
taacacngtg cgagctgttt ctt                                            23

<210> SEQ ID NO 8
<211> LENGTH: 20
<212> TYPE: DNA
<213> ORGANISM: West Nile Virus

<400> SEQUENCE: 8
cgagctgttt cttagcacga                                                20

<210> SEQ ID NO 9
<211> LENGTH: 21
<212> TYPE: DNA
<213> ORGANISM: West Nile Virus

<400> SEQUENCE: 9
cgagctgttt cttagcacga a                                              21

<210> SEQ ID NO 10
<211> LENGTH: 24
<212> TYPE: DNA
<213> ORGANISM: West Nile Virus

<400> SEQUENCE: 10
gaagatctcg atgtctaaga aacc                                           24

<210> SEQ ID NO 11
<211> LENGTH: 23
<212> TYPE: DNA
<213> ORGANISM: West Nile Virus

<400> SEQUENCE: 11
aagatctcga tgtctaagaa acc                                            23

<210> SEQ ID NO 12
<211> LENGTH: 22
<212> TYPE: DNA
<213> ORGANISM: West Nile Virus

<400> SEQUENCE: 12
agatctcgat gtctaagaaa cc                                             22

<210> SEQ ID NO 13
<211> LENGTH: 22
<212> TYPE: DNA
<213> ORGANISM: West Nile Virus

<400> SEQUENCE: 13
gatctcgatg tctaagaaac ca                                             22

<210> SEQ ID NO 14
<211> LENGTH: 21
<212> TYPE: DNA
<213> ORGANISM: West Nile Virus

<400> SEQUENCE: 14
gatctcgatg tctaagaaac c                                              21

<210> SEQ ID NO 15
<211> LENGTH: 22
<212> TYPE: DNA
<213> ORGANISM: West Nile Virus

<400> SEQUENCE: 15
```

```
atctcgatgt ctaagaaacc ag                                              22
```

<210> SEQ ID NO 16
<211> LENGTH: 69
<212> TYPE: DNA
<213> ORGANISM: West Nile Virus

<400> SEQUENCE: 16

```
acatagccct cttcagtcca atcaaggaca acacgcgggg cattccgcgt tttagcatat     60
tgacagccc                                                             69
```

<210> SEQ ID NO 17
<211> LENGTH: 21
<212> TYPE: DNA
<213> ORGANISM: West Nile Virus

<400> SEQUENCE: 17

```
gttttagcat attgacagcc c                                               21
```

<210> SEQ ID NO 18
<211> LENGTH: 20
<212> TYPE: DNA
<213> ORGANISM: West Nile Virus

<400> SEQUENCE: 18

```
gttttagcat attgacagcc                                                 20
```

<210> SEQ ID NO 19
<211> LENGTH: 21
<212> TYPE: DNA
<213> ORGANISM: West Nile Virus

<400> SEQUENCE: 19

```
ttccgcgttt tagcatattg a                                               21
```

<210> SEQ ID NO 20
<211> LENGTH: 21
<212> TYPE: DNA
<213> ORGANISM: West Nile Virus

<400> SEQUENCE: 20

```
attccgcgtt ttagcatatt g                                               21
```

<210> SEQ ID NO 21
<211> LENGTH: 23
<212> TYPE: DNA
<213> ORGANISM: West Nile Virus

<400> SEQUENCE: 21

```
atcaaggaca acacgcgggg cat                                             23
```

<210> SEQ ID NO 22
<211> LENGTH: 23
<212> TYPE: DNA
<213> ORGANISM: West Nile Virus
<220> FEATURE:
<221> NAME/KEY: modified_base
<222> LOCATION: (12)...(12)
<223> OTHER INFORMATION: I

<400> SEQUENCE: 22

```
atcaaggaca anacgcgggg cat                                             23
```

<210> SEQ ID NO 23

```
<211> LENGTH: 24
<212> TYPE: DNA
<213> ORGANISM: West Nile Virus

<400> SEQUENCE: 23
cctcttcagt ccaatcaagg acaa                                          24

<210> SEQ ID NO 24
<211> LENGTH: 24
<212> TYPE: DNA
<213> ORGANISM: West Nile Virus

<400> SEQUENCE: 24
agccctcttc agtccaatca agga                                          24

<210> SEQ ID NO 25
<211> LENGTH: 24
<212> TYPE: DNA
<213> ORGANISM: West Nile Virus

<400> SEQUENCE: 25
tagccctctt cagtccaatc aagg                                          24

<210> SEQ ID NO 26
<211> LENGTH: 24
<212> TYPE: DNA
<213> ORGANISM: West Nile Virus

<400> SEQUENCE: 26
atagccctct tcagtccaat caag                                          24

<210> SEQ ID NO 27
<211> LENGTH: 22
<212> TYPE: DNA
<213> ORGANISM: West Nile Virus

<400> SEQUENCE: 27
tagccctctt cagtccaatc aa                                            22

<210> SEQ ID NO 28
<211> LENGTH: 24
<212> TYPE: DNA
<213> ORGANISM: West Nile Virus

<400> SEQUENCE: 28
acatagccct cttcagtcca atca                                          24

<210> SEQ ID NO 29
<211> LENGTH: 48
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(48)
<223> OTHER INFORMATION: WNV-complementary sequence

<400> SEQUENCE: 29
aatttaatac gactcactat agggagagtt ttagcatatt gacagccc                48

<210> SEQ ID NO 30
<211> LENGTH: 47
<212> TYPE: DNA
<213> ORGANISM: Artificial Sequence
```

<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(47)
<223> OTHER INFORMATION: WNV-complementary sequence

<400> SEQUENCE: 30
aatttaatac gactcactat agggagagtt ttagcatatt gacagcc 47

<210> SEQ ID NO 31
<211> LENGTH: 48
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter-primer
<221> NAME/KEY: misc_feature
<222> LOCATION: (28)...(48)
<223> OTHER INFORMATION: WNV-complementary sequence

<400> SEQUENCE: 31
aatttaatac gactcactat agggagattc cgcgttttag catattga 48

<210> SEQ ID NO 32
<211> LENGTH: 48
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(48)
<223> OTHER INFORMATION: WNV-complementary sequence

<400> SEQUENCE: 32
aatttaatac gactcactat agggagaatt ccgcgtttta gcatattg 48

<210> SEQ ID NO 33
<211> LENGTH: 50
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(50)
<223> OTHER INFORMATION: WNV-complementary sequence

<400> SEQUENCE: 33
aatttaatac gactcactat agggagaatc aaggacaaca cgcggggcat 50

<210> SEQ ID NO 34
<211> LENGTH: 50
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(50)
<223> OTHER INFORMATION: WNV-complementary sequence
<221> NAME/KEY: modified_base
<222> LOCATION: (39)...(39)
<223> OTHER INFORMATION: I

<400> SEQUENCE: 34
aatttaatac gactcactat agggagaatc aaggacaana cgcggggcat        50

<210> SEQ ID NO 35
<211> LENGTH: 51
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(51)
<223> OTHER INFORMATION: WNV-complementary sequence

<400> SEQUENCE: 35
aatttaatac gactcactat agggagacct cttcagtcca atcaaggaca a        51

<210> SEQ ID NO 36
<211> LENGTH: 51
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(51)
<223> OTHER INFORMATION: WNV-complementary sequence

<400> SEQUENCE: 36
aatttaatac gactcactat agggagaagc cctcttcagt ccaatcaagg a 51

<210> SEQ ID NO 37
<211> LENGTH: 51
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(51)
<223> OTHER INFORMATION: WNV-complementary sequence

<400> SEQUENCE: 37
aatttaatac gactcactat agggagatag ccctcttcag tccaatcaag g 51

<210> SEQ ID NO 38
<211> LENGTH: 51
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(51)
<223> OTHER INFORMATION: WNV-complementary sequence

<400> SEQUENCE: 38
aatttaatac gactcactat agggagaata gccctcttca gtccaatcaa g 51

<210> SEQ ID NO 39
<211> LENGTH: 49
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence -continued

```
<221> NAME/KEY: misc_feature
<222> LOCATION: (28)...(49)
<223> OTHER INFORMATION: WNV-complementary sequence

<400

```
<400> SEQUENCE: 46
tcgtgttctt ggccacccag ga                                              22

<210> SEQ ID NO 47
<211> LENGTH: 23
<212> TYPE: DNA
<213> ORGANISM: West Nile Virus
<220> FEATURE:
<221> NAME/KEY: modified_base
<222> LOCATION: (5)...(5)
<223> OTHER INFORMATION: I

<400> SEQUENCE: 47
ttganccttt tcagttgggc ctt                                             23

<210> SEQ ID NO 48
<211> LENGTH: 23
<212> TYPE: DNA
<213> ORGANISM: West Nile Virus
<220> FEATURE:
<221> NAME/KEY: modified_base
<222> LOCATION: (15)...(15)
<223> OTHER INFORMATION: I

<400> SEQUENCE: 48
ttgacccttt tcagntgggc ctt                                             23

<210> SEQ ID NO 49
<211> LENGTH: 22
<212> TYPE: DNA
<213> ORGANISM: West Nile Virus
<220> FEATURE:
<221> NAME/KEY: modified_base
<222> LOCATION: (9)...(9)
<223> OTHER INFORMATION: I

<400> SEQUENCE: 49
cttttcagnt gggccttctg gt                                              22

<210> SEQ ID NO 50
<211> LENGTH: 22
<212> TYPE: DNA
<213> ORGANISM: West Nile Virus
<220> FEATURE:
<221> NAME/KEY: modified_base
<222> LOCATION: (11)...(11)
<223> OTHER INFORMATION: I

<400> SEQUENCE: 50
tggtcgtgtt nttggccacc ca                                              22

<210> SEQ ID NO 51
<211> LENGTH: 22
<212> TYPE: DNA
<213> ORGANISM: West Nile Virus
<220> FEATURE:
<221> NAME/KEY: modified_base
<222> LOCATION: (12)...(12)
<223> OTHER INFORMATION: I

<400> SEQUENCE: 51
tggtcgtgtt cntggccacc ca                                              22

<210> SEQ ID NO 52
<211> LENGTH: 26
<212> TYPE: DNA
<213> ORGANISM: West Nile Virus
```

<400> SEQUENCE: 52
atagctggca tgctgatctt ggctgt                                              26

<210> SEQ ID NO 53
<211> LENGTH: 22
<212> TYPE: DNA
<213> ORGANISM: West Nile Virus

<400> SEQUENCE: 53
ctggcatgct gatcttggct gt                                                  22

<210> SEQ ID NO 54
<211> LENGTH: 23
<212> TYPE: DNA
<213> ORGANISM: West Nile Virus

<400> SEQUENCE: 54
atagctggca tgctgatctt ggc                                                 23

<210> SEQ ID NO 55
<211> LENGTH: 22
<212> TYPE: DNA
<213> ORGANISM: West Nile Virus

<400> SEQUENCE: 55
atagctggca tgctgatctt gg                                                  22

<210> SEQ ID NO 56
<211> LENGTH: 49
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(49)
<223> OTHER INFORMATION: WNV-complementary sequence

<400> SEQUENCE: 56
aatttaatac gactcactat agggagactg gcatgctgat cttggctgt                     49

<210> SEQ ID NO 57
<211> LENGTH: 50
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(50)
<223> OTHER INFORMATION: WNV-complementary sequence

<400> SEQUENCE: 57
aatttaatac gactcactat agggagaata gctggcatgc tgatcttggc 50

<210> SEQ ID NO 58
<211> LENGTH: 49
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(49)

<223> OTHER INFORMATION: WNV-complementary sequence

<400> SEQUENCE: 58
aatttaatac gactcactat agggagaata gctggcatgc tgatcttgg 49

<210> SEQ ID NO 59
<211> LENGTH: 31
<212> TYPE: DNA
<213> ORGANISM: West Nile Virus

<400> SEQUENCE: 59
tccgccaccg gaagttgagt agacggtgct g 31

<210> SEQ ID NO 60
<211> LENGTH: 19
<212> TYPE: DNA
<213> ORGANISM: West Nile Virus

<400> SEQUENCE: 60
tccgccaccg gaagttgag 19

<210> SEQ ID NO 61
<211> LENGTH: 19
<212> TYPE: DNA
<213> ORGANISM: West Nile Virus
<220> FEATURE:
<221> NAME/KEY: modified_base
<222> LOCATION: (1)...(1)
<223> OTHER INFORMATION: I

<400> SEQUENCE: 61
nccgccaccg gaagttgag 19

<210> SEQ ID NO 62
<211> LENGTH: 20
<212> TYPE: DNA
<213> ORGANISM: West Nile Virus

<400> SEQUENCE: 62
tccgccaccg gaagttgagt 20

<210> SEQ ID NO 63
<211> LENGTH: 21
<212> TYPE: DNA
<213> ORGANISM: West Nile Virus

<400> SEQUENCE: 63
tccgccaccg gaagttgagt a 21

<210> SEQ ID NO 64
<211> LENGTH: 18
<212> TYPE: DNA
<213> ORGANISM: West Nile Virus

<400> SEQUENCE: 64
cgccaccgga agttgagt 18

<210> SEQ ID NO 65
<211> LENGTH: 18
<212> TYPE: DNA
<213> ORGANISM: West Nile Virus
<220> FEATURE:
<221> NAME/KEY: modified_base
<222> LOCATION: (1)...(1)
<223> OTHER INFORMATION: I

```
<400> SEQUENCE: 65
ngccaccgga agttgagt                                                    18

<210> SEQ ID NO 66
<211> LENGTH: 19
<212> TYPE: DNA
<213> ORGANISM: West Nile Virus

<400> SEQUENCE: 66
cgccaccgga agttgagta                                                   19

<210> SEQ ID NO 67
<211> LENGTH: 21
<212> TYPE: DNA
<213> ORGANISM: West Nile Virus

<400> SEQUENCE: 67
ggaagttgag tagacggtgc t                                                21

<210> SEQ ID NO 68
<211> LENGTH: 22
<212> TYPE: DNA
<213> ORGANISM: West Nile Virus

<400> SEQUENCE: 68
ggaagttgag tagacggtgc tg                                               22

<210> SEQ ID NO 69
<211> LENGTH: 20
<212> TYPE: DNA
<213> ORGANISM: West Nile Virus

<400> SEQUENCE: 69
gaagttgagt agacggtgct                                                  20

<210> SEQ ID NO 70
<211> LENGTH: 21
<212> TYPE: DNA
<213> ORGANISM: West Nile Virus

<400> SEQUENCE: 70
gaagttgagt agacggtgct g                                                21

<210> SEQ ID NO 71
<211> LENGTH: 20
<212> TYPE: DNA
<213> ORGANISM: West Nile Virus

<400> SEQUENCE: 71
aagttgagta gacggtgctg                                                  20

<210> SEQ ID NO 72
<211> LENGTH: 70
<212> TYPE: DNA
<213> ORGANISM: West Nile Virus

<400> SEQUENCE: 72
tccgagacgg ttctgagggc ttacatggat cacttcgcag ctttgttcac ccagtcctcc      60
tggggttgag                                                             70

<210> SEQ ID NO 73
<211> LENGTH: 48
<212> TYPE: DNA
```

<213> ORGANISM: West Nile Virus

<400> SEQUENCE: 73
tccgagacgg ttctgagggc ttacatggat cacttcgcag ctttgttc        48

<210> SEQ ID NO 74
<211> LENGTH: 24
<212> TYPE: DNA
<213> ORGANISM: West Nile Virus

<400> SEQUENCE: 74
tccgagacgg ttctgagggc ttac        24

<210> SEQ ID NO 75
<211> LENGTH: 24
<212> TYPE: DNA
<213> ORGANISM: West Nile Virus

<400> SEQUENCE: 75
tccgagacgg ttctgagggc ttac        24

<210> SEQ ID NO 76
<211> LENGTH: 23
<212> TYPE: DNA
<213> ORGANISM: West Nile Virus

<400> SEQUENCE: 76
tccgagacgg ttctgagggc tta        23

<210> SEQ ID NO 77
<211> LENGTH: 22
<212> TYPE: DNA
<213> ORGANISM: West Nile Virus

<400> SEQUENCE: 77
tccgagacgg ttctgagggc tt        22

<210> SEQ ID NO 78
<211> LENGTH: 20
<212> TYPE: DNA
<213> ORGANISM: West Nile Virus

<400> SEQUENCE: 78
ccagtcctcc tggggttgag        20

<210> SEQ ID NO 79
<211> LENGTH: 22
<212> TYPE: DNA
<213> ORGANISM: West Nile Virus

<400> SEQUENCE: 79
acccagtcct cctggggttg ag        22

<210> SEQ ID NO 80
<211> LENGTH: 21
<212> TYPE: DNA
<213> ORGANISM: West Nile Virus

<400> SEQUENCE: 80
acccagtcct cctggggttg a        21

<210> SEQ ID NO 81
<211> LENGTH: 20
<212> TYPE: DNA

-continued

```
<213> ORGANISM: West Nile Virus

<400> SEQUENCE: 81
acccagtcct cctggggttg                                              20

<210> SEQ ID NO 82
<211> LENGTH: 20
<212> TYPE: DNA
<213> ORGANISM: West Nile Virus
<220> FEATURE:
<221> NAME/KEY: modified_base
<222> LOCATION: (7)...(7)
<223> OTHER INFORMATION: I
<221> NAME/KEY: modified_base
<222> LOCATION: (10)...(10)
<223> OTHER INFORMATION: I

<400> SEQUENCE: 82
gctacancan gtgggtcct                                               20

<210> SEQ ID NO 83
<211> LENGTH: 20
<212> TYPE: DNA
<213> ORGANISM: West Nile Virus
<220> FEATURE:
<221> NAME/KEY: modified_base
<222> LOCATION: (10)...(10)
<223> OTHER INFORMATION: I

<400> SEQUENCE: 83
gctacaacan gtgggtcct                                               20

<210> SEQ ID NO 84
<211> LENGTH: 51
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(51)
<223> OTHER INFORMATION: WNV-complementary sequence

<400> SEQUENCE: 84
aatttaatac gactcactat agggagatcc gagacggttc tgagggctta c           51

<210> SEQ ID NO 85
<211> LENGTH: 50
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(50)
<223> OTHER INFORMATION: WNV-complementary sequence

<400> SEQUENCE: 85
aatttaatac gactcactat agggagatcc gagacggttc tgagggctta             50

<210> SEQ ID NO 86
<211> LENGTH: 49
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence
```

```
<221> NAME/KEY: misc_feature
<222> LOCATION: (28)...(49)
<223> OTHER INFORMATION: WNV-complementary sequence

<400> SE

```
<213> ORGANISM: Artificial Sequence
<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(47)
<223> OTHER INFORMATION: WNV-complementary sequence
<221> NAME/KEY: modified_base
<222> LOCATION: (34)...(34)
<223> OTHER INFORMATION: I
<221> NAME/KEY: modified_base
<222> LOCATION: (37)...(37)
<223> OTHER INFORMATION: I

<400> SEQUENCE: 91
aatttaatac gactcactat agggagagct acancangtg gggtcct           47

<210> SEQ ID NO 92
<211> LENGTH: 47
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: T7 promoter sequence
<221> NAME/KEY: misc_feature
<222> LOCATION: (28)...(47)
<223> OTHER INFORMATION: WNV-complementary sequence
<221> NAME/KEY: modified_base
<222> LOCATION: (37)...(37)
<223> OTHER INFORMATION: I

<400> SEQUENCE: 92
aatttaatac gactcactat agggagagct acaacangtg gggtcct           47

<210> SEQ ID NO 93
<211> LENGTH: 65
<212> TYPE: DNA
<213> ORGANISM: West Nile Virus

<400> SEQUENCE: 93
tgtctaagaa accaggaggg cccggcaaga gccgggctgt caatatgcta aaacgcggaa     60
tgccc                                                                65

<210> SEQ ID NO 94
<211> LENGTH: 25
<212> TYPE: DNA
<213> ORGANISM: West Nile Virus

<400> SEQUENCE: 94
tgtctaagaa accaggaggg cccgg                                          25

<210> SEQ ID NO 95
<211> LENGTH: 37
<212> TYPE: DNA
<213> ORGANISM: West Nile Virus

<400> SEQUENCE: 95
gagccgggct gtcaatatgc taaaacgcgg aatgccc                             37

<210> SEQ ID NO 96
<211> LENGTH: 21
<212> TYPE: DNA
<213> ORGANISM: West Nile Virus
<220> FEATURE:
<221> NAME/KEY: misc_feature
<222> LOCATION: (1)...(21)
<223> OTHER INFORMATION: 2'-OMe nucleotide analogs
```

```
<400> SEQUENCE: 96
tgtctaagaa accaggaggg c                                          21

<210> SEQ ID NO 97
<211> LENGTH: 18
<212> TYPE: DNA
<213> ORGANISM: West Nile Virus
<220> FEATURE:
<221> NAME/KEY: misc_feature
<222> LOCATION: (1)...(18)
<223> OTHER INFORMATION: 2'-OMe nucleotide analogs

<400> SEQUENCE: 97
gaaaccagga gggcccgg                                              18

<210> SEQ ID NO 98
<211> LENGTH: 20
<212> TYPE: DNA
<213> ORGANISM: West Nile Virus
<220> FEATURE:
<221> NAME/KEY: misc_feature
<222> LOCATION: (1)...(20)
<223> OTHER INFORMATION: 2'-OMe nucleotide analogs

<400> SEQUENCE: 98
gctgtcaata tgctaaaacg                                            20

<210> SEQ ID NO 99
<211> LENGTH: 20
<212> TYPE: DNA
<213> ORGANISM: West Nile Virus

<400> SEQUENCE: 99
aggtccttcg caagaggtgg                                            20

<210> SEQ ID NO 100
<211> LENGTH: 19
<212> TYPE: DNA
<213> ORGANISM: West Nile Virus
<220> FEATURE:
<221> NAME/KEY: misc_feature
<222> LOCATION: (1)...(19)
<223> OTHER INFORMATION: 2'-OMe nucleotide analogs

<400> SEQUENCE: 100
ggtccttcgc aagaggtgg                                             19

<210> SEQ ID NO 101
<211> LENGTH: 87
<212> TYPE: DNA
<213> ORGANISM: West Nile Virus

<400> SEQUENCE: 101
gagtagacgg tgctgcctgc gactcaaccc caggaggact gggtgaacaa agccgcgaag    60
tgatccatgt aagccctcag aaccgtc                                       87

<210> SEQ ID NO 102
<211> LENGTH: 69
<212> TYPE: DNA
<213> ORGANISM: West Nile Virus

<400> SEQUENCE: 102
gagtagacgg tgctgcctgc gactcaaccc caggaggact gggtgaacaa agccgcgaag    60
tgatccatg                                                           69
```

```
<210> SEQ ID NO 103
<211> LENGTH: 52
<212> TYPE: DNA
<213> ORGANISM: West Nile Virus

<400> SEQUENCE: 103
tgcgactcaa ccccaggagg actgggtgaa caaagccgcg aagtgatcca tg        52

<210> SEQ ID NO 104
<211> LENGTH: 21
<212> TYPE: DNA
<213> ORGANISM: West Nile Virus
<220> FEATURE:
<221> NAME/KEY: misc_feature
<222> LOCATION: (1)...(21)
<223> OTHER INFORMATION: 2'-OMe nucleotide analogs

<400> SEQUENCE: 104
gagtagacgg tgctgcctgc g                                          21

<210> SEQ ID NO 105
<211> LENGTH: 19
<212> TYPE: DNA
<213> ORGANISM: West Nile Virus
<220> FEATURE:
<221> NAME/KEY: misc_feature
<222> LOCATION: (1)...(19)
<223> OTHER INFORMATION: 2'-OMe nucleotide analogs

<400> SEQUENCE: 105
gtagacggtg ctgcctgcg                                             19

<210> SEQ ID NO 106
<211> LENGTH: 22
<212> TYPE: DNA
<213> ORGANISM: West Nile Virus
<220> FEATURE:
<221> NAME/KEY: misc_feature
<222> LOCATION: (1)...(22)
<223> OTHER INFORMATION: 2'-OMe nucleotide analogs

<400> SEQUENCE: 106
tgcgactcaa ccccaggagg ac                                         22

<210> SEQ ID NO 107
<211> LENGTH: 18
<212> TYPE: DNA
<213> ORGANISM: West Nile Virus
<220> FEATURE:
<221> NAME/KEY: misc_feature
<222> LOCATION: (1)...(18)
<223> OTHER INFORMATION: 2'-OMe nucleotide analogs

<400> SEQUENCE: 107
tgcgactcaa ccccagga                                              18

<210> SEQ ID NO 108
<211> LENGTH: 20
<212> TYPE: DNA
<213> ORGANISM: West Nile Virus
<220> FEATURE:
<221> NAME/KEY: misc_feature
<222> LOCATION: (1)...(20)
<223> OTHER INFORMATION: 2'-OMe nucleotide analogs

<400> SEQUENCE: 108
cgactcaacc ccaggaggac                                            20
```

```
<210> SEQ ID NO 109
<211> LENGTH: 19
<212> TYPE: DNA
<213> ORGANISM: West Nile Virus
<220> FEATURE:
<221> NAME/KEY: misc_feature
<222> LOCATION: (1)...(19)
<223> OTHER INFORMATION: 2'-OMe nucleotide analogs

<400> SEQUENCE: 109
gactcaaccc caggaggac                                              19

<210> SEQ ID NO 110
<211> LENGTH: 18
<212> TYPE: DNA
<213> ORGANISM: West Nile Virus
<220> FEATURE:
<221> NAME/KEY: misc_feature
<222> LOCATION: (1)...(18)
<223> OTHER INFORMATION: 2'-OMe nucleotide analogs

<400> SEQUENCE: 110
gactcaaccc caggagga                                               18

<210> SEQ ID NO 111
<211> LENGTH: 18
<212> TYPE: DNA
<213> ORGANISM: West Nile Virus
<220> FEATURE:
<221> NAME/KEY: misc_feature
<222> LOCATION: (1)...(18)
<223> OTHER INFORMATION: 2'-OMe nucleotide analogs

<400> SEQUENCE: 111
actcaacccc aggaggac                                               18

<210> SEQ ID NO 112
<211> LENGTH: 19
<212> TYPE: RNA
<213> ORGANISM: West Nile Virus
<220> FEATURE:
<221> NAME/KEY: misc_feature
<222> LOCATION: (1)...(19)
<223> OTHER INFORMATION: 2'-OMe nucleotide analogs

<400> SEQUENCE: 112
caggaggacu gggugaaca                                              19

<210> SEQ ID NO 113
<211> LENGTH: 19
<212> TYPE: RNA
<213> ORGANISM: West Nile Virus
<220> FEATURE:
<221> NAME/KEY: misc_feature
<222> LOCATION: (1)...(19)
<223> OTHER INFORMATION: 2'-OMe nucleotide analogs

<400> SEQUENCE: 113
gaggacuggg ugaacaaag                                              19

<210> SEQ ID NO 114
<211> LENGTH: 20
<212> TYPE: DNA
<213> ORGANISM: West Nile Virus
<220> FEATURE:
<221> NAME/KEY: misc_feature
<222> LOCATION: (1)...(20)
<223> OTHER INFORMATION: 2'-OMe nucleotide analogs
```

```
<400> SEQUENCE: 114
gtgaacaaag ctgcgaagtg                                              20

<210> SEQ ID NO 115
<211> LENGTH: 20
<212> TYPE: DNA
<213> ORGANISM: West Nile Virus
<220> FEATURE:
<221> NAME/KEY: misc_feature
<222> LOCATION: (1)...(20)
<223> OTHER INFORMATION: 2'-OMe nucleotide analogs

<400> SEQUENCE: 115
aagccgcgaa gtgatccatg                                              20

<210> SEQ ID NO 116
<211> LENGTH: 19
<212> TYPE: DNA
<213> ORGANISM: West Nile Virus
<220> FEATURE:
<221> NAME/KEY: misc_feature
<222> LOCATION: (1)...(19)
<223> OTHER INFORMATION: 2'-OMe nucleotide analogs

<400> SEQUENCE: 116
gtaagccctc agaaccgtc                                               19

<210> SEQ ID NO 117
<211> LENGTH: 23
<212> TYPE: RNA
<213> ORGANISM: West Nile Virus
<220> FEATURE:
<221> NAME/KEY: misc_feature
<222> LOCATION: (1)...(23)
<223> OTHER INFORMATION: 2'-OMe nucleotide analogs

<400> SEQUENCE: 117
aauccucaca aacacuacua agu                                          23

<210> SEQ ID NO 118
<211> LENGTH: 23
<212> TYPE: DNA
<213> ORGANISM: West Nile Virus
<220> FEATURE:
<221> NAME/KEY: misc_feature
<222> LOCATION: (1)...(23)
<223> OTHER INFORMATION: 2'-OMe nucleotide analogs

<400> SEQUENCE: 118
aagaacgcca agagagccaa cac                                          23

<210> SEQ ID NO 119
<211> LENGTH: 26
<212> TYPE: RNA
<213> ORGANISM: West Nile Virus
<220> FEATURE:
<221> NAME/KEY: misc_feature
<222> LOCATION: (1)...(26)
<223> OTHER INFORMATION: 2'-OMe nucleotide analogs

<400> SEQUENCE: 119
ccucuuuucu uuuguuuuga gcuccg                                       26

<210> SEQ ID NO 120
<211> LENGTH: 23
<212> TYPE: DNA
<213> ORGANISM: West Nile Virus
```

```
<220> FEATURE:
<221> NAME/KEY: misc_feature
<222> LOCATION: (1)...(23)
<223> OTHER INFORMATION: 2'-OMe nucleotide analogs

<400> SEQUENCE: 120
aatcctcaca aacactacta agt                                              23

<210> SEQ ID NO 121
<211> LENGTH: 22
<212> TYPE: DNA
<213> ORGANISM: West Nile Virus
<220> FEATURE:
<221> NAME/KEY: misc_feature
<222> LOCATION: (1)...(22)
<223> OTHER INFORMATION: 2'-OMe nucleotide analogs

<400> SEQUENCE: 121
cctcctcttt tcttttgttt tg                                               22

<210> SEQ ID NO 122
<211> LENGTH: 25
<212> TYPE: RNA
<213> ORGANISM: West Nile Virus
<220> FEATURE:
<221> NAME/KEY: misc_feature
<222> LOCATION: (1)...(25)
<223> OTHER INFORMATION: 2'-OMe nucleotide analogs

<400> SEQUENCE: 122
ccuccucuuu ucuuuuguuu ugagc                                            25

<210> SEQ ID NO 123
<211> LENGTH: 25
<212> TYPE: DNA
<213> ORGANISM: West Nile Virus
<220> FEATURE:
<221> NAME/KEY: misc_feature
<222> LOCATION: (1)...(25)
<223> OTHER INFORMATION: 2'-OMe nucleotide analogs

<400> SEQUENCE: 123
cctcctcttt tcttttgttt tgagc                                            25

<210> SEQ ID NO 124
<211> LENGTH: 23
<212> TYPE: RNA
<213> ORGANISM: West Nile Virus
<220> FEATURE:
<221> NAME/KEY: misc_feature
<222> LOCATION: (1)...(23)
<223> OTHER INFORMATION: 2'-OMe nucleotide analogs

<400> SEQUENCE: 124
uucaucgcug uuuguuuguu cac                                              23

<210> SEQ ID NO 125
<211> LENGTH: 23
<212> TYPE: DNA
<213> ORGANISM: West Nile Virus
<220> FEATURE:
<221> NAME/KEY: misc_feature
<222> LOCATION: (1)...(23)
<223> OTHER INFORMATION: 2'-OMe nucleotide analogs

<400> SEQUENCE: 125
tgtgtctgca ctgtcagtga cct                                              23
```

```
<210> SEQ ID NO 126
<211> LENGTH: 23
<212> TYPE: RNA
<213> ORGANISM: West Nile Virus
<220> FEATURE:
<221> NAME/KEY: misc_feature
<222> LOCATION: (1)...(23)
<223> OTHER INFORMATION: 2'-OMe nucleotide analogs

<400> SEQUENCE: 126
ugugucugca cugucaguga ccu                                             23

<210> SEQ ID NO 127
<211> LENGTH: 21
<212> TYPE: RNA
<213> ORGANISM: West Nile Virus
<220> FEATURE:
<221> NAME/KEY: misc_feature
<222> LOCATION: (1)...(21)
<223> OTHER INFORMATION: 2'-OMe nucleotide analogs

<400> SEQUENCE: 127
guuuugucuu ccauccauuc a                                               21

<210> SEQ ID NO 128
<211> LENGTH: 22
<212> TYPE: RNA
<213> ORGANISM: West Nile Virus
<220> FEATURE:
<221> NAME/KEY: misc_feature
<222> LOCATION: (1)...(22)
<223> OTHER INFORMATION: 2'-OMe nucleotide analogs

<400> SEQUENCE: 128
guuuugucuu ccauccauuc au                                              22

<210> SEQ ID NO 129
<211> LENGTH: 25
<212> TYPE: RNA
<213> ORGANISM: West Nile Virus
<220> FEATURE:
<221> NAME/KEY: misc_feature
<222> LOCATION: (1)...(25)
<223> OTHER INFORMATION: 2'-OMe nucleotide analogs

<400> SEQUENCE: 129
ucucucucuu ucccaucaug uugua                                           25

<210> SEQ ID NO 130
<211> LENGTH: 22
<212> TYPE: RNA
<213> ORGANISM: West Nile Virus
<220> FEATURE:
<221> NAME/KEY: misc_feature
<222> LOCATION: (1)...(22)
<223> OTHER INFORMATION: 2'-OMe nucleotide analogs

<400> SEQUENCE: 130
ccuccucuuu ucuuuuguuu ug                                              22

<210> SEQ ID NO 131
<211> LENGTH: 23
<212> TYPE: RNA
<213> ORGANISM: West Nile Virus
<220> FEATURE:
<221> NAME/KEY: misc_feature
<222> LOCATION: (1)...(23)
<223> OTHER INFORMATION: 2'-OMe nucleotide analogs

<400> SEQUENCE: 131
```
ccaacugauc caaaguccca agc                                           23

<210> SEQ ID NO 132
<211> LENGTH: 24
<212> TYPE: RNA
<213> ORGANISM: West Nile Virus
<220> FEATURE:
<221> NAME/KEY: misc_feature
<222> LOCATION: (1)...(24)
<223> OTHER INFORMATION: 2'-OMe nucleotide analogs

<400> SEQUENCE: 132
accccuccaa cugauccaaa gucc                                          24

<210> SEQ ID NO 133
<211> LENGTH: 24
<212> TYPE: RNA
<213> ORGANISM: West Nile Virus
<220> FEATURE:
<221> NAME/KEY: misc_feature
<222> LOCATION: (1)...(24)
<223> OTHER INFORMATION: 2'-OMe nucleotide analogs

<400> SEQUENCE: 133 gaacacccu ccaacugauc caaa                                           24

<210> SEQ ID NO 134
<211> LENGTH: 20
<212> TYPE: RNA
<213> ORGANISM: West Nile Virus
<220> FEATURE:
<221> NAME/KEY: misc_feature
<222> LOCATION: (1)...(20)
<223> OTHER INFORMATION: 2'-OMe nucleotide analogs

<400> SEQUENCE: 134
gcagguccac gguguccgca                                               20

<210> SEQ ID NO 135
<211> LENGTH: 23
<212> TYPE: RNA
<213> ORGANISM: West Nile Virus
<220> FEATURE:
<221> NAME/KEY: misc_feature
<222> LOCATION: (1)...(23)
<223> OTHER INFORMATION: 2'-OMe nucleotide analogs

<400> SEQUENCE: 135
uucaucgcug uuuguuuguu cac                                           23

<210> SEQ ID NO 136
<211> LENGTH: 22
<212> TYPE: DNA
<213> ORGANISM: West Nile Virus
<220> FEATURE:
<221> NAME/KEY: misc_feature
<222> LOCATION: (1)...(22)
<223> OTHER INFORMATION: 2'-OMe nucleotide analogs

<400> SEQUENCE: 136
cctcctcttt tcttttgttt tg                                            22

<210> SEQ ID NO 137
<211> LENGTH: 20
<212> TYPE: DNA
<213> ORGANISM: West Nile Virus
<220> FEATURE:
<221> NAME/KEY: misc_feature

```
<222> LOCATION: (1)...(20)
<223> OTHER INFORMATION: 2'-OMe nucleotide analogs

<400> SEQUENCE: 137
gcaggtccac ggtgtccgca                                           20

<210> SEQ ID NO 138
<211> LENGTH: 22
<212> TYPE: RNA
<213> ORGANISM: West Nile Virus
<220> FEATURE:
<221> NAME/KEY: misc_feature
<222> LOCATION: (1)...(22)
<223> OTHER INFORMATION: 2'-OMe nucleotide analogs

<400> SEQUENCE: 138
cuuccaucca uucauucucc uc                                        22

<210> SEQ ID NO 139
<211> LENGTH: 24
<212> TYPE: RNA
<213> ORGANISM: West Nile Virus
<220> FEATURE:
<221> NAME/KEY: misc_feature
<222> LOCATION: (1)...(24)
<223> OTHER INFORMATION: 2'-OMe nucleotide analogs

<400> SEQUENCE: 139
guuuugucuu ccauccauuc auuc                                      24

<210> SEQ ID NO 140
<211> LENGTH: 22
<212> TYPE: DNA
<213> ORGANISM: West Nile Virus
<220> FEATURE:
<221> NAME/KEY: misc_feature
<222> LOCATION: (1)...(22)
<223> OTHER INFORMATION: 2'-OMe nucleotide analogs

<400> SEQUENCE: 140
gttttgtctt ccatccattc at                                        22

<210> SEQ ID NO 141
<211> LENGTH: 23
<212> TYPE: DNA
<213> ORGANISM: West Nile Virus
<220> FEATURE:
<221> NAME/KEY: misc_feature
<222> LOCATION: (1)...(23)
<223> OTHER INFORMATION: 2'-OMe nucleotide analogs

<400> SEQUENCE: 141
ctggggtttt gtcttccatc cat                                       23

<210> SEQ ID NO 142
<211> LENGTH: 23
<212> TYPE: RNA
<213> ORGANISM: West Nile Virus
<220> FEATURE:
<221> NAME/KEY: misc_feature
<222> LOCATION: (1)...(23)
<223> OTHER INFORMATION: 2'-OMe nucleotide analogs

<400> SEQUENCE: 142 cuggguuuu gucuuccauc cau                                        23

<210> SEQ ID NO 143
<211> LENGTH: 23
```

```
<212> TYPE: RNA
<213> ORGANISM: West Nile Virus
<220> FEATURE:
<221> NAME/KEY: misc_feature
<222> LOCATION: (1)...(23)
<223> OTHER INFORMATION: 2'-OMe nucleotide analogs

<400> SEQUENCE: 143
gcccuccugg uuucuuagac auc                                              23

<210> SEQ ID NO 144
<211> LENGTH: 30
<212> TYPE: RNA
<213> ORGANISM: West Nile Virus
<220> FEATURE:
<221> NAME/KEY: misc_feature
<222> LOCATION: (1)...(30)
<223> OTHER INFORMATION: 2'-OMe nucleotide analogs

<400> SEQUENCE: 144
uugccgggcc cuccugguuu cuuagacauc                                       30

<210> SEQ ID NO 145
<211> LENGTH: 24
<212> TYPE: RNA
<213> ORGANISM: West Nile Virus
<220> FEATURE:
<221> NAME/KEY: misc_feature
<222> LOCATION: (1)...(24)
<223> OTHER INFORMATION: 2'-OMe nucleotide analogs

<400> SEQUENCE: 145
cgcguuuuag cauauugaca gccc                                             24

<210> SEQ ID NO 146
<211> LENGTH: 23
<212> TYPE: RNA
<213> ORGANISM: West Nile Virus
<220> FEATURE:
<221> NAME/KEY: misc_feature
<222> LOCATION: (1)...(23)
<223> OTHER INFORMATION: 2'-OMe nucleotide analogs

<400> SEQUENCE: 146
uccaccucuu gcgaaggacc ucc                                              23

<210> SEQ ID NO 147
<211> LENGTH: 26
<212> TYPE: RNA
<213> ORGANISM: West Nile Virus
<220> FEATURE:
<221> NAME/KEY: misc_feature
<222> LOCATION: (1)...(26)
<223> OTHER INFORMATION: 2'-OMe nucleotide analogs

<400> SEQUENCE: 147
gucgcaggca gcaccgucua cucaac                                           26

<210> SEQ ID NO 148
<211> LENGTH: 24
<212> TYPE: RNA
<213> ORGANISM: West Nile Virus
<220> FEATURE:
<221> NAME/KEY: misc_feature
<222> LOCATION: (1)...(24)
<223> OTHER INFORMATION: 2'-OMe nucleotide analogs

<400> SEQUENCE: 148
caguccuccu ggguugagu cgca                                              24
```

<210> SEQ ID NO 149
<211> LENGTH: 23
<212> TYPE: RNA
<213> ORGANISM: West Nile Virus
<220> FEATURE:
<221> NAME/KEY: misc_feature
<222> LOCATION: (1)...(23)
<223> OTHER INFORMATION: 2'-OMe nucleotide analogs

<400> SEQUENCE: 149
gagacgguuc ugagggcuua cau                                          23

<210> SEQ ID NO 150
<211> LENGTH: 24
<212> TYPE: RNA
<213> ORGANISM: West Nile Virus
<220> FEATURE:
<221> NAME/KEY: misc_feature
<222> LOCATION: (1)...(24)
<223> OTHER INFORMATION: 2'-OMe nucleotide analogs

<400> SEQUENCE: 150 caguccccu gggguugagu cgca                                          24

<210> SEQ ID NO 151
<211> LENGTH: 24
<212> TYPE: RNA
<213> ORGANISM: West Nile Virus
<220> FEATURE:
<221> NAME/KEY: misc_feature
<222> LOCATION: (1)...(24)
<223> OTHER INFORMATION: 2'-OMe nucleotide analogs

<400> SEQUENCE: 151
caguccuccu gggguugagc cgca                                         24

<210> SEQ ID NO 152
<211> LENGTH: 24
<212> TYPE: RNA
<213> ORGANISM: West Nile Virus
<220> FEATURE:
<221> NAME/KEY: misc_feature
<222> LOCATION: (1)...(24)
<223> OTHER INFORMATION: 2'-OMe nucleotide analogs

<400> SEQUENCE: 152
cagucauccu gggguugagu cgca                                         24

<210> SEQ ID NO 153
<211> LENGTH: 27
<212> TYPE: DNA
<213> ORGANISM: Phage T7

<400> SEQUENCE: 153
aatttaatac gactcactat agggaga                                      27

<210> SEQ ID NO 154
<211> LENGTH: 15
<212> TYPE: RNA
<213> ORGANISM: West Nile Virus
<220> FEATURE:
<221> NAME/KEY: misc_feature
<222> LOCATION: (1)...(15)
<223> OTHER INFORMATION: 2'-OMe nucleotide analogs

<400> SEQUENCE: 154
gucaauaugc uaaaa                                                   15

```
<210> SEQ ID NO 155
<211> LENGTH: 14
<212> TYPE: RNA
<213> ORGANISM: West Nile Virus
<220> FEATURE:
<221> NAME/KEY: misc_feature
<222> LOCATION: (1)...(14)
<223> OTHER INFORMATION: 2'-OMe nucleotide analogs

<400> SEQUENCE: 155
gucaauaugc uaaa                                                         14

<210> SEQ ID NO 156
<211> LENGTH: 15
<212> TYPE: RNA
<213> ORGANISM: West Nile Virus
<220> FEATURE:
<221> NAME/KEY: misc_feature
<222> LOCATION: (1)...(15)
<223> OTHER INFORMATION: 2'-OMe nucleotide analogs

<400> SEQUENCE: 156
ugucaauaug cuaaa                                                        15

<210> SEQ ID NO 157
<211> LENGTH: 13
<212> TYPE: RNA
<213> ORGANISM: West Nile Virus
<220> FEATURE:
<221> NAME/KEY: misc_feature
<222> LOCATION: (1)...(13)
<223> OTHER INFORMATION: 2'-OMe nucleotide analogs

<400> SEQUENCE: 157
gagccgggcu guc                                                          13

<210> SEQ ID NO 158
<211> LENGTH: 15
<212> TYPE: RNA
<213> ORGANISM: West Nile Virus
<220> FEATURE:
<221> NAME/KEY: misc_feature
<222> LOCATION: (1)...(15)
<223> OTHER INFORMATION: 2'-OMe nucleotide analogs

<400> SEQUENCE: 158
aaacgcggaa ugccc                                                        15

<210> SEQ ID NO 159
<211> LENGTH: 25
<212> TYPE: RNA
<213> ORGANISM: West Nile Virus
<220> FEATURE:
<221> NAME/KEY: misc_feature
<222> LOCATION: (1)...(25)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (21)...(25)
<223> OTHER INFORMATION: Molecular beacon arm sequence

<400> SEQUENCE: 159
ccgaggucaa uaugcuaaaa cucgg                                             25

<210> SEQ ID NO 160
<211> LENGTH: 24
```

-continued

<212> TYPE: RNA
<213> ORGANISM: West Nile Virus
<220> FEATURE:
<221> NAME/KEY: misc_feature
<222> LOCATION: (1)...(24)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (20)...(24)
<223> OTHER INFORMATION: Molecular beacon arm sequence

<400> SEQUENCE: 160
ccgaggucaa uaugcuaaac ucgg 24

<210> SEQ ID NO 161
<211> LENGTH: 26
<212> TYPE: RNA
<213> ORGANISM: West Nile Virus
<220> FEATURE:
<221> NAME/KEY: misc_feature
<222> LOCATION: (1)...(26)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (22)...(26)
<223> OTHER INFORMATION: Molecular beacon arm sequence

<400> SEQUENCE: 161
ccgaguguca auaugcuaaa ccucgg 26

<210> SEQ ID NO 162
<211> LENGTH: 23
<212> TYPE: RNA
<213> ORGANISM: West Nile Virus
<220> FEATURE:
<221> NAME/KEY: misc_feature
<222> LOCATION: (1)...(23)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (19)...(23)
<223> OTHER INFORMATION: Molecular beacon arm sequence

<400> SEQUENCE: 162
ggcacgagcc gggcugucgu gcc 23

<210> SEQ ID NO 163
<211> LENGTH: 25
<212> TYPE: RNA
<213> ORGANISM: West Nile Virus
<220> FEATURE:
<221> NAME/KEY: misc_feature
<222> LOCATION: (1)...(25)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (21)...(25)
<223> OTHER INFORMATION: Molecular beacon arm sequence

<400> SEQUENCE: 163
ccgagaaacg cggaaugccc cucgg 25

<210> SEQ ID NO 164
<211> LENGTH: 16

```
<212> TYPE: RNA
<213> ORGANISM: West Nile Virus
<220> FEATURE:
<221> NAME/KEY: misc_feature
<222> LOCATION: (1)...(16)
<223> OTHER INFORMATION: 2'-OMe nucleotide analogs

<400> SEQUENCE: 164
gguccuucgc aagagg                                                    16

<210> SEQ ID NO 165
<211> LENGTH: 17
<212> TYPE: RNA
<213> ORGANISM: West Nile Virus
<220> FEATURE:
<221> NAME/KEY: misc_feature
<222> LOCATION: (1)...(17)
<223> OTHER INFORMATION: 2'-OMe nucleotide analogs

<400> SEQUENCE: 165
gguccuucgc aagaggu                                                   17

<210> SEQ ID NO 166
<211> LENGTH: 10
<212> TYPE: RNA
<213> ORGANISM: West Nile Virus
<220> FEATURE:
<221> NAME/KEY: misc_feature
<222> LOCATION: (1)...(10)
<223> OTHER INFORMATION: 2'-OMe nucleotide analogs

<400> SEQUENCE: 166
gguccuucgc                                                           10

<210> SEQ ID NO 167
<211> LENGTH: 18
<212> TYPE: RNA
<213> ORGANISM: West Nile Virus
<220> FEATURE:
<221> NAME/KEY: misc_feature
<222> LOCATION: (1)...(18)
<223> OTHER INFORMATION: 2'-OMe nucleotide analogs

<400> SEQUENCE: 167
agguccuucg caagaggu                                                  18

<210> SEQ ID NO 168
<211> LENGTH: 18
<212> TYPE: RNA
<213> ORGANISM: West Nile Virus
<220> FEATURE:
<221> NAME/KEY: misc_feature
<222> LOCATION: (1)...(18)
<223> OTHER INFORMATION: 2'-OMe nucleotide analogs

<400> SEQUENCE: 168
gguccuucgc aagaggug                                                  18

<210> SEQ ID NO 169
<211> LENGTH: 19
<212> TYPE: RNA
<213> ORGANISM: West Nile Virus
<220> FEATURE:
<221> NAME/KEY: misc_feature
<222> LOCATION: (1)...(19)
<223> OTHER INFORMATION: 2'-OMe nucleotide analogs

<400> SEQUENCE: 169
gguccuucgc aagaggugg                                                 19
```

<210> SEQ ID NO 170
<211> LENGTH: 20
<212> TYPE: RNA
<213> ORGANISM: West Nile Virus
<220> FEATURE:
<221> NAME/KEY: misc_feature
<222> LOCATION: (1)...(20)
<223> OTHER INFORMATION: 2'-OMe nucleotide analogs

<400> SEQUENCE: 170
agguccuucg caagaggugg        20

<210> SEQ ID NO 171
<211> LENGTH: 26
<212> TYPE: RNA
<213> ORGANISM: West Nile Virus
<220> FEATURE:
<221> NAME/KEY: misc_feature
<222> LOCATION: (1)...(26)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (22)...(26)
<223> OTHER INFORMATION: Molecular beacon arm sequence

<400> SEQUENCE: 171
ccgagggucc uucgcaagag gcucgg        26

<210> SEQ ID NO 172
<211> LENGTH: 27
<212> TYPE: RNA
<213> ORGANISM: West Nile Virus
<220> FEATURE:
<221> NAME/KEY: misc_feature
<222> LOCATION: (1)...(27)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (23)...(27)
<223> OTHER INFORMATION: Molecular beacon arm sequence

<400> SEQUENCE: 172
ccgagggucc uucgcaagag gucucgg        27

<210> SEQ ID NO 173
<211> LENGTH: 20
<212> TYPE: RNA
<213> ORGANISM: West Nile Virus
<220> FEATURE:
<221> NAME/KEY: misc_feature
<222> LOCATION: (1)...(20)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (16)...(20)
<223> OTHER INFORMATION: Molecular beacon arm sequence

<400> SEQUENCE: 173
ccgagggucc uucgccucgg        20

<210> SEQ ID NO 174
<211> LENGTH: 28
<212> TYPE: RNA
<213> ORGANISM: West Nile Virus

```
<220> FEATURE:
<221> NAME/KEY: misc_feature
<222> LOCATION: (1)...(28)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (24)...(28)
<223> OTHER INFORMATION: Molecular beacon arm sequence

<400> SEQUENCE: 174
ccgagagguc cuucgcaaga ggucucgg                                          28

<210> SEQ ID NO 175
<211> LENGTH: 28
<212> TYPE: RNA
<213> ORGANISM: West Nile Virus
<220> FEATURE:
<221> NAME/KEY: misc_feature
<222> LOCATION: (1)...(28)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (24)...(28)
<223> OTHER INFORMATION: Molecular beacon arm sequence

<400> SEQUENCE: 175
ccgagggucc uucgcaagag gugcucgg                                          28

<210> SEQ ID NO 176
<211> LENGTH: 29
<212> TYPE: RNA
<213> ORGANISM: West Nile Virus
<220> FEATURE:
<221> NAME/KEY: misc_feature
<222> LOCATION: (1)...(29)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (25)...(29)
<223> OTHER INFORMATION: Molecular beacon arm sequence

<400> SEQUENCE: 176
ccgagggucc uucgcaagag guggcucgg                                         29

<210> SEQ ID NO 177
<211> LENGTH: 30
<212> TYPE: RNA
<213> ORGANISM: West Nile Virus
<220> FEATURE:
<221> NAME/KEY: misc_feature
<222> LOCATION: (1)...(30)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (26)...(30)
<223> OTHER INFORMATION: Molecular beacon arm sequence

<400> SEQUENCE: 177
ccgagagguc cuucgcaaga gguggcucgg                                        30

<210> SEQ ID NO 178
<211> LENGTH: 18
<212> TYPE: DNA
<213> ORGANISM: West Nile Virus
```

```
<220> FEATURE:
<221> NAME/KEY: misc_feature
<222> LOCATION: (1)...(18)
<223> OTHER INFORMATION: 2'-OMe nucleotide analogs

<400> SEQUENCE: 178
tagacggtgc tgcctgcg                                                 18

<210> SEQ ID NO 179
<211> LENGTH: 14
<212> TYPE: RNA
<213> ORGANISM: West Nile Virus
<220> FEATURE:
<221> NAME/KEY: misc_feature
<222> LOCATION: (1)...(14)
<223> OTHER INFORMATION: 2'-OMe nucleotide analogs

<400> SEQUENCE: 179
cggugcugcc ugcg                                                     14

<210> SEQ ID NO 180
<211> LENGTH: 12
<212> TYPE: RNA
<213> ORGANISM: West Nile Virus
<220> FEATURE:
<221> NAME/KEY: misc_feature
<222> LOCATION: (1)...(12)
<223> OTHER INFORMATION: 2'-OMe nucleotide analogs

<400> SEQUENCE: 180
uagacggugc ug                                                       12

<210> SEQ ID NO 181
<211> LENGTH: 18
<212> TYPE: RNA
<213> ORGANISM: West Nile Virus
<220> FEATURE:
<221> NAME/KEY: misc_feature
<222> LOCATION: (1)...(18)
<223> OTHER INFORMATION: 2'-OMe nucleotide analogs

<400> SEQUENCE: 181
uagacggugc ugccugcg                                                 18

<210> SEQ ID NO 182
<211> LENGTH: 18
<212> TYPE: RNA
<213> ORGANISM: West Nile Virus
<220> FEATURE:
<221> NAME/KEY: misc_feature
<222> LOCATION: (1)...(18)
<223> OTHER INFORMATION: 2'-OMe nucleotide analogs

<400> SEQUENCE: 182
ugaacaaagc cgcgaagu                                                 18

<210> SEQ ID NO 183
<211> LENGTH: 17
<212> TYPE: RNA
<213> ORGANISM: West Nile Virus
<220> FEATURE:
<221> NAME/KEY: misc_feature
<222> LOCATION: (1)...(17)
<223> OTHER INFORMATION: 2'-OMe nucleotide analogs

<400> SEQUENCE: 183
cucaacccca ggaggac                                                  17
```

```
<210> SEQ ID NO 184
<211> LENGTH: 24
<212> TYPE: RNA
<213> ORGANISM: West Nile Virus
<220> FEATURE:
<221> NAME/KEY: misc_feature
<222> LOCATION: (1)...(24)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (20)...(24)
<223> OTHER INFORMATION: Molecular beacon arm sequence

<400> SEQUENCE: 184
ccgagcggug cugccugcgc ucgg                                              24

<210> SEQ ID NO 185
<211> LENGTH: 22
<212> TYPE: RNA
<213> ORGANISM: West Nile Virus
<220> FEATURE:
<221> NAME/KEY: misc_feature
<222> LOCATION: (1)...(22)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (18)...(22)
<223> OTHER INFORMATION: Molecular beacon arm sequence

<400> SEQUENCE: 185
ccgaguagac ggugcugcuc gg                                                22

<210> SEQ ID NO 186
<211> LENGTH: 28
<212> TYPE: RNA
<213> ORGANISM: West Nile Virus
<220> FEATURE:
<221> NAME/KEY: misc_feature
<222> LOCATION: (1)...(28)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (24)...(28)
<223> OTHER INFORMATION: Molecular beacon arm sequence

<400> SEQUENCE: 186
ccgaguagac ggugcugccu gcgcucgg                                          28

<210> SEQ ID NO 187
<211> LENGTH: 28
<212> TYPE: RNA
<213> ORGANISM: West Nile Virus
<220> FEATURE:
<221> NAME/KEY: misc_feature
<222> LOCATION: (1)...(28)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (24)...(28)
<223> OTHER INFORMATION: Molecular beacon arm sequence

<400> SEQUENCE: 187
ccgagugaac aaagccgcga agucucgg                                          28
```

```
<210> SEQ ID NO 188
<211> LENGTH: 27
<212> TYPE: RNA
<213> ORGANISM: West Nile Virus
<220> FEATURE:
<221> NAME/KEY: misc_feature
<222> LOCATION: (1)...(27)
<223> OTHER INFORMATION: 2'-OMe nucleotide analogs
<221> NAME/KEY: misc_feature
<222> LOCATION: (1)...(5)
<223> OTHER INFORMATION: Molecular beacon arm sequence
<221> NAME/KEY: misc_feature
<222> LOCATION: (23)...(27)
<223> OTHER INFORMATION: Molecular beacon arm sequence

<400> SEQUENCE: 188
ccgagcucaa ccccaggagg accucgg                                            27

<210> SEQ ID NO 189
<211> LENGTH: 17
<212> TYPE: DNA
<213> ORGANISM: West Nile Virus
<220> FEATURE:
<221> NAME/KEY: misc_feature
<222> LOCATION: (1)...(17)
<223> OTHER INFORMATION: 2'-OMe nucleotide analogs

<400> SEQUENCE: 189
ccctgcgact caacccc                                                       17

<210> SEQ ID NO 190
<211> LENGTH: 16
<212> TYPE: DNA
<213> ORGANISM: West Nile Virus
<220> FEATURE:
<221> NAME/KEY: misc_feature
<222> LOCATION: (1)...(16)
<223> OTHER INFORMATION: 2'-OMe nucleotide analogs

<400> SEQUENCE: 190
cctgcgactc aacccc                                                        16

<210> SEQ ID NO 191
<211> LENGTH: 15
<212> TYPE: DNA
<213> ORGANISM: West Nile Virus
<220> FEATURE:
<221> NAME/KEY: misc_feature
<222> LOCATION: (1)...(15)
<223> OTHER INFORMATION: 2'-OMe nucleotide analogs

<400> SEQUENCE: 191
cctgcgactc aaccc                                                         15

<210> SEQ ID NO 192
<211> LENGTH: 19
<212> TYPE: DNA
<213> ORGANISM: West Nile Virus
<220> FEATURE:
<221> NAME/KEY: misc_feature
<222> LOCATION: (1)...(19)
<223> OTHER INFORMATION: 2'-OMe nucleotide analogs

<400> SEQUENCE: 192
aggaggactg ggtgaacaa                                                     19

<210> SEQ ID NO 193
<211> LENGTH: 30
<212> TYPE: RNA
<213> ORGANISM: West Nile Virus
```

-continued

```
<220> FEATURE:
<221> NAME/KEY: misc_feature
<222> LOCATION: (1)...(30)
<223> OTHER INFORMATION: 2'-OMe nucleotide analogs

<400> SEQUENCE: 193
ccaguccucc ugggguugag ucgcagggca                                          30

<210> SEQ ID NO 194
<211> LENGTH: 22
<212> TYPE: RNA
<213> ORGANISM: West Nile Virus
<220> FEATURE:
<221> NAME/KEY: misc_feature
<222> LOCATION: (1)...(22)
<223> OTHER INFORMATION: 2'-OMe nucleotide analogs

<400> SEQUENCE: 194
cuuuguucac ccaguccucc ug                                                  22

<210> SEQ ID NO 195
<211> LENGTH: 36
<212> TYPE: RNA
<213> ORGANISM: West Nile Virus
<220> FEATURE:
<221> NAME/KEY: misc_feature
<222> LOCATION: (1)...(36)
<223> OTHER INFORMATION: 2'-OMe nucleotide analogs

<400> SEQUENCE: 195
gaucacuucg cagcuuuguu cacccagucc uccugg                                   36

<210> SEQ ID NO 196
<211> LENGTH: 23
<212> TYPE: RNA
<213> ORGANISM: West Nile Virus
<220> FEATURE:
<221> NAME/KEY: misc_feature
<222> LOCATION: (1)...(23)
<223> OTHER INFORMATION: 2'-OMe nucleotide analogs

<400> SEQUENCE: 196
acauggauca cuucgcggcu uug                                                 23
```

METHOD FOR DETECTING WEST NILE VIRUS NUCLEIC ACIDS IN THE 3' NON-CODING REGION

RELATED APPLICATIONS

This application is a continuation of U.S. patent application Ser. No. 11/519,359, filed Sep. 11, 2006, which claims the benefit of U.S. patent application Ser. No. 10/688,489, filed Oct. 16, 2003, now issued as U.S. Pat. No. 7,115,374, which claims the benefit of U.S. Provisional Application No. 60/449,810, filed Feb. 24, 2003; U.S. Provisional Application No. 60/429,006, filed Nov. 25, 2002; and U.S. Provisional Application No. 60/418,891, filed Oct. 16, 2002. The disclosures of these prior applications are hereby incorporated by reference.

GOVERNMENT INTEREST IN INVENTION

Certain aspects of the invention disclosed herein were made with government support under contract N01-HB-07148 with the National Heart, Lung and Blood Institute of the National Institutes of Health. The United States government has certain rights in these aspects of the invention.

FIELD OF THE INVENTION

The present invention relates to the field of biotechnology. More specifically, the invention relates to diagnostic assays for detecting the nucleic acids of flaviviruses, such as West Nile virus.

BACKGROUND OF THE INVENTION

West Nile virus (WNV) is an RNA virus that primarily infects birds and culex mosquitos, with humans and horses serving as incidental hosts. Amplification of virus in a bird-mosquito-bird cycle begins when adult mosquitos emerge in early spring and continues until fall. This timing coincides with the incidence of disease in humans, which peaks in late summer and early fall. Since it was first detected in New York during 1999, the virus has spread rapidly throughout most of the United States.

Indeed, during the first nine months of 2002, a total of more than 2,500 human cases with laboratory evidence of recent WNV infection were reported in 32 states and the District of Columbia. A total of more than 120 human deaths were reported, with the median age of decedents being 79 years. Additionally, there were reports of nearly 5,000 dead crows and nearly 4,000 other dead birds with WNV infection in the United States. Of more than 3,000 mammals detected with WNV infection, greater than 99% were horses. There were also nearly 3,400 WNV-positive mosquito pools reported.

Most human infections with the virus are not clinically apparent. Overall, only 1 in 150 infections results in severe neurologic illness such as meningitis (inflammation of the spinal cord) or encephalitis (inflammation of the brain). Milder symptoms, which generally last 3 to 6 days and are more commonly reported in connection with WNV infection, include a fever of sudden onset, often accompanied by malaise, anorexia, nausea, vomiting, eye pain, headache, myalgia, rash, and lymphadenopathy. The incubation period of WNV, although not precisely known, probably ranges from 3 to 14 days. An analysis of attack rates per million persons during the 1999 New York City outbreak showed that the incidence of severe neurologic disease was more than 40 times higher in those at least 80 years of age when compared with persons up to 19 years of age. Thus, advanced age is an important risk factor for more severe neurologic disease.

In addition to transmission from mosquitoes, transmission has been linked to blood transfusion and organ transplantation. For example, four recipients of transplanted organs from single donor in the U.S. became infected with West Nile virus in mid-2002. Three of the recipients developed encephalitis, with one of the three dying as a result. The fourth recipient developed mild symptoms of viral infection without encephalitis, but also tested positive for the virus. The organ donor, who was injured in an automobile accident, received numerous transfusions of blood products before dying. She was not known to have been ill before the accident, and a sample of her blood taken before any of the transfusions showed no evidence of West Nile virus. In a separate instance, a nursing mother whose breast milk contained WNV and a male liver transplant patient both received transfused blood from a common donor, and both developed West Nile virus infections. A stored blood sample from that donor tested positive for the WNV, again suggesting a common source of the infectious virus.

West Nile virus is a single-stranded plus-sense RNA virus taxonomically classified in the family *Flaviviridae*, under the genus *Flavivirus*. Accordingly, the virus is a member of the Japanese encephalitis virus serocomplex, which contains several medically important viruses associated with human encephalitis: Japanese encephalitis, St. Louis encephalitis, Murray Valley encephalitis, and Kunjin virus (an Australian subtype of West Nile virus). The viral genome size is approximately 11 kb.

Nucleic acid-based tests for WNV have been described. For example, Shi et al., in *J. Clin. Microbiol.* 39:1264 (2001) have described a real-time polymerase chain reaction (PCR) assay for WNV nucleic acids. Lanciotti et al., in *J. Clin. Microbiol.* 38:4066 (2001) have described a TaqMan-based assay for the detection of WNV RNA in human specimens, mosquito pools, and avian tissue specimens. Despite the availability of these PCR-based tests, there remains a need for a WNV screening assay that is specifically adapted for the needs of clinical testing laboratories. The method should particularly lend itself to high throughput screening which may be required for testing large numbers of clinical and donated blood or tissue samples.

SUMMARY OF THE INVENTION

A first aspect of the invention relates to a hybridization assay probe for detecting a nucleic acid. This hybridization assay probe includes a probe sequence that has a target-complementary sequence of bases, and optionally one or more base sequences that are not complementary to the nucleic acid that is to be detected. The target-complementary sequence of bases consists of 12-87 contiguous bases contained within the sequence of SEQ ID NO:101 or the complement thereof, allowing for the presence of RNA and DNA equivalents, nucleotide analogs and up to 10%, or even up to 20% base differences. In general, the invented hybridization assay probe can have a length of up to 100 bases. In a preferred embodiment, the target-complementary sequence of bases consists of 12-69 contiguous bases contained within the sequence of SEQ ID NO:102 or the complement thereof, allowing for the presence of RNA and DNA equivalents, nucleotide analogs and up to 10%, or even up to 20% base differences. Still more preferably, the hybridization assay probe includes the optional base sequences that are not complementary to the nucleic acid that is to be detected. Even still more preferably, the hybridization assay probe includes a detectable label. For example, the probe may include a fluorophore moiety and a quencher moiety. In such an instance the hybridization assay probe can be a molecular beacon. An exemplary molecular beacon can include a target-complementary sequence of bases that consists of any one of SEQ ID NO:179, SEQ ID NO:180 or SEQ ID NO:181. In accordance with another preferred embodiment of the invented hybridization assay probe, when the target-complementary sequence of bases consists of 12-69 contiguous bases contained within the sequence of SEQ ID NO:102 or the complement thereof, allowing for the presence of RNA and DNA equivalents, nucleotide analogs and up to 10%, or even up to 20% base differences, the probe sequence does not include the optional base sequences that are not complementary to the nucleic acid that is to be detected. Still more preferably, the invented hybridization assay probe has a length of up to 69 bases, and yet still more preferably includes a detectable label. In accordance with another preferred embodiment, the target-complementary sequence of bases consists of 18-52 contiguous bases contained within the sequence of SEQ ID NO:103 or the complement thereof, allowing for the presence of RNA and DNA equivalents, nucleotide analogs and up to 10%, or even up to 20% base differences. Still more preferably, the probe sequence does not include the optional base sequences that are not complementary to the nucleic acid that is to be detected, but may further include a detectable label. This detectable label can be either a chemiluminescent label or a fluorescent label. In accordance with an alternative embodiment, the hybridization assay probe consists of 18-52 contiguous bases contained within the sequence of SEQ ID NO:103 or the complement thereof, allowing for the presence of RNA and DNA equivalents, nucleotide analogs and up to 10%, or even up to 20% base differences, and has a length of up to 52 bases. When this is the case, the target-complementary sequence of bases can consist of 18-22 contiguous bases contained within the sequence of SEQ ID NO:103 or the complement thereof, allowing for the presence of RNA and DNA equivalents, nucleotide analogs and up to 10%, or even up to 20% base differences, and the hybridization assay probe can have a length of up to 22 bases. In one embodiment, the invented probe can have the sequence of SEQ ID NO:116. In another embodiment, the probe sequence can be any of SEQ ID NO:114, SEQ ID NO:111, SEQ ID NO:110, SEQ ID NO:109, SEQ ID NO:108, SEQ ID NO:107 or SEQ ID NO:106.

Another aspect of the invention relates to a kit for amplifying a target nucleic acid sequence that may be present in a biological sample. The invented kit contains a first primer that has a 3' terminal target-complementary sequence and optionally a first primer upstream sequence that is not complementary to the target nucleic acid sequence that is to be amplified. The 3' terminal target-complementary sequence of this first primer includes 22 contiguous bases contained within SEQ ID NO:73, allowing for the presence of RNA and DNA equivalents, nucleotide analogs and up to 10%, or even up to 20% base differences. Also included in the kit is a second primer that has a 3' terminal target-complementary sequence and optionally a second primer upstream sequence that is not complementary to the target nucleic acid sequence that is to be amplified. The 3' terminal target-complementary sequence of the second primer includes 18 contiguous bases contained within SEQ ID NO:59, allowing for the presence of RNA and DNA equivalents, nucleotide analogs and up to 10%, or even up to 20% base differences. In a preferred embodiment of the invented kit, the first primer and the second primer are each up to 60 bases in length. In another preferred embodiment, the 3' terminal target-complementary sequence of the first primer and the 3' terminal target-complementary sequence of the second primer are each up to 35 bases in length. When this is the case, it is preferable for the 3' terminal target-complementary sequence of the first primer to be up to 24 bases in length. Alternatively, and in accordance with yet another preferred embodiment, the 3' terminal target-complementary sequence of the first primer can be up to 35 bases in length and the 31 terminal target-complementary sequence of the second primer can be up to 22 bases in length. When the first primer is up to 24 bases in length, it is highly preferred for the 3' terminal target-complementary sequence of the second primer to be up to 22 bases in length. Still more preferably, the first primer includes a first primer upstream sequence, such as a promoter sequence for T7 RNA polymerase. In accordance with another preferred embodiment of the invented kit, when the 3' terminal target-complementary sequence of the first primer is up to 24 bases in length, and when the 3' terminal target-complementary sequence of the second primer is up to 22 bases in length, the 3' terminal target-complementary sequence of the first primer is preferably any of SEQ ID NO:75, SEQ ID NO:76 and SEQ ID NO:77, and the 3' terminal target-complementary sequence of the second primer is preferably any of SEQ ID NO:60, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70 and SEQ ID NO:71. In accordance with another preferred embodiment, when the 3' terminal target-complementary sequence of the first primer is up to 24 bases in length, and when the 3' terminal target-complementary sequence of the second primer is up to 35 bases in length, the 3' terminal target-complementary sequence of the first primer includes 22 contiguous bases contained within SEQ ID NO:74, allowing for the presence of RNA and DNA equivalents, nucleotide analogs and up to 10%, or even up to 20% base differences. When this is the case, the 3' terminal target-complementary sequence of the second primer can be up to 22 bases in length. Alternatively, the first primer may include a first primer upstream sequence, such as a promoter sequence for T7 RNA polymerase.

Another aspect of the invention relates to a hybridization assay probe for detecting a nucleic acid. The invented hybridization assay probe includes a probe sequence that has a target-complementary sequence of bases, and optionally one or more base sequences that are not complementary to the nucleic acid that is to be detected. The target-complementary sequence of bases consists of 10-20 contiguous bases contained within the sequence of SEQ ID NO:99 or the complement thereof, allowing for the presence of RNA and DNA equivalents, nucleotide analogs and up to 10%, or even up to 20% base differences. Finally, the invented hybridization assay probe can have a length of up to 100 bases. In a preferred embodiment, the length of the hybridization assay probe is up to 30 bases. Still more preferably, the probe sequence includes the optional base sequences that are not complementary to the nucleic acid that is to be detected. In accordance with a first version of this embodiment, there is further included a detectable label. In accordance with a second version of this embodiment, there is further included a fluorophore moiety and a quencher moiety, and the hybridization assay probe is a molecular beacon. In a different embodiment, wherein the length of the hybridization assay probe is up to 30 bases, the probe sequence consists of 10-20 contiguous bases contained within the sequence of SEQ ID NO:99 or the complement thereof, allowing for the presence of RNA and DNA equivalents, nucleotide analogs and up to 10%, or even up to 20% base differences, and does not include the optional base sequences that are not complementary to the WNV nucleic acids. More preferably, the hybridization assay probe has a length of up to 20 bases. In certain embodiments wherein the length of the hybridization assay probe is up to 30 bases, the target-complementary sequence of bases consists of 19-20 contiguous bases contained within the sequence of SEQ ID NO:99 or the complement thereof, allowing for the presence of RNA and DNA equivalents, nucleotide analogs and up to 10%, or even up to 20% base differences. In accordance with a first preferred version of this embodiment, the probe sequence consists of 19-20 contiguous bases contained within the sequence of SEQ ID NO:99 or the complement thereof, allowing for the presence of RNA and DNA equivalents, nucleotide analogs and up to 10%, or even up to 20% base differences, and does not include the optional base sequences that are not complementary to the nucleic acid that is to be detected. In accordance with a second preferred version of this embodiment, the hybridization assay probe further includes a detectable label, such as a chemiluminescent label or a fluorescent label. In accordance with a third preferred version of this embodiment, the target-complementary sequence of bases consists of 19-20 contiguous bases contained within the sequence of SEQ ID NO:99 or the complement thereof, allowing for the presence of RNA and DNA equivalents, nucleotide analogs and up to 10%, or even up to 20% base differences, and the hybridization assay probe has a length of up to 20 bases. For example, the probe sequence can be SEQ ID NO:100. In accordance with a different embodiment, when the length of the hybridization assay probe is up to 30 bases, and when the probe sequence includes the optional base sequences that are not complementary to the nucleic acid that is to be detected, the target-complementary sequence of bases may be any of SEQ ID NO:164, SEQ ID NO:165, SEQ ID NO:166, SEQ ID NO:167, SEQ ID NO:168, SEQ ID NO:169 or SEQ ID NO:170.

Another aspect of the invention relates to a kit for amplifying a target nucleic acid sequence that may be present in a biological sample. This kit contains a first primer that includes a 3' terminal target-complementary sequence and optionally a first primer upstream sequence that is not complementary to the target nucleic acid sequence that is to be amplified. The 3' terminal target-complementary sequence of the first primer includes 22 contiguous bases contained within SEQ ID NO:52, allowing for the presence of RNA and DNA equivalents, nucleotide analogs and up to 10%, or even up to 20% base differences. The kit further contains a second primer that includes a 3' terminal target-complementary sequence and optionally a second primer upstream sequence that is not complementary to the target nucleic acid sequence that is to be amplified. The 3' terminal target-complementary sequence of the second primer includes 22 contiguous bases contained within SEQ ID NO:41, allowing for the presence of RNA and DNA equivalents, nucleotide analogs and up to 10%, or even up to 20% base differences. In a preferred embodiment, the first primer and the second primer each are up to 60 bases in length. In a different preferred embodiment, the 3' terminal target-complementary sequence of the first primer and the 3' terminal target-complementary sequence of the second primer are each up to 35 bases in length. When this is the case, the 3' terminal target-complementary sequence of the first primer is preferably up to 26 bases in length. In accordance with a different preferred embodiment, when the 3' terminal target-complementary sequence of the first primer and the 3' terminal target-complementary sequence of the second primer are each up to 35 bases in length, the 3' terminal target-complementary sequence of the second primer can be up to 23 bases in length. In yet another preferred embodiment, the 3' terminal target-complementary sequence of the first primer is preferably up to 26 bases in length, and the 3' terminal target-complementary sequence of the second primer is up to 23 bases in length. In accordance with a first preferred version of this embodiment, the 3' terminal target-complementary sequence of the first primer may be selected from the group consisting of SEQ ID NO:53, SEQ ID NO:54 and SEQ ID NO:55, and the 3' terminal target-complementary sequence of the second primer may be selected from the group consisting of SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, and SEQ ID NO:51. In accordance with a second preferred version of this embodiment, the 3' terminal target-complementary sequence of the second primer is up to 23 bases in length. When this is the case, the first primer may include a first primer upstream sequence, such as a promoter sequence for T7 RNA polymerase.

Another aspect of the invention relates to a hybridization assay probe for detecting a nucleic acid. The invented hybridization assay probe has a probe sequence that includes a target-complementary sequence of bases, and optionally one or more base sequences that are not complementary to the nucleic acid that is to be detected. The target-complementary sequence of bases consists of 13-37 contiguous bases contained within the sequence of SEQ ID NO:95 or the complement thereof, allowing for the presence of RNA and DNA equivalents, nucleotide analogs and up to 10%, or even up to 20% base differences. Generally speaking, the hybridization assay probe can have a length of up to 100 bases. In a preferred embodiment, the length of the hybridization assay probe is up to 37 bases. More preferably, the hybridization assay probe includes the optional base sequences that are not complementary to the nucleic acid that is to be detected. Still more preferably, the hybridization assay probe further includes a detectable label. For example, the hybridization assay probe may further include a fluorophore moiety and a quencher moiety. In this instance the hybridization assay probe can be a molecular beacon. In a different embodiment of the invented hybridization assay probe, the probe sequence consists of 13-20 contiguous bases contained within the sequence of SEQ ID NO:95 or the complement thereof, allowing for the presence of RNA and DNA equivalents, nucleotide analogs and up to 10%, or even up to 20% base differences, and does not include the optional base sequences that are not complementary to the nucleic acid that is to be detected. In accordance with still another embodiment, when the length of the hybridization assay probe is up to 37 bases, the target-complementary sequence of bases consists of 13-20 contiguous bases contained within the sequence of SEQ ID NO:95 or the complement thereof, allowing for the presence of RNA and DNA equivalents, nucleotide analogs and up to 10%, or even up to 20% base differences. More preferably, the probe sequence consists of 20 contiguous bases contained within the sequence of SEQ ID NO:95 or the complement thereof, allowing for the presence of RNA and DNA equivalents, nucleotide analogs and up to 10%, or even up to 20% base differences, and does not include the optional base sequences that are not complementary to the nucleic acid that is to be detected. Still more preferably, the hybridization assay probe further includes a detectable label, such as a chemiluminescent label or a fluorescent label. In accordance with still yet another preferred embodiment, when the length of the hybridization assay probe is up to 37 bases, and when the target-complementary sequence of bases consists of 13-20 contiguous bases contained within the sequence of SEQ ID NO:95 or the complement thereof, allowing for the presence of RNA and DNA equivalents, nucleotide analogs and up to 10%, or even up to 20% base differences, the probe sequence does not include the optional base sequences that are not complementary to the nucleic acid that is to be detected, and the hybridization assay probe has a length of up to 20 bases. For example, the probe sequence may be SEQ ID NO:98. Generally speaking, when the length of the hybridization assay probe is up to 37 bases, the target-complementary sequence of bases can, for example, be any one of SEQ ID NO:154, SEQ ID NO:155, SEQ ID NO:156, SEQ ID NO:157, or SEQ ID NO:158.

Another aspect of the invention relates to a kit for amplifying a target nucleic acid sequence that may be present in a biological sample. The invented kit contains a first primer that includes a 3' terminal target-complementary sequence, and optionally a first primer upstream sequence that is not complementary to the target nucleic acid sequence that is to be amplified. The 3' terminal target-complementary sequence of the first primer includes 20 contiguous bases contained within SEQ ID NO:16, allowing for the presence of RNA and DNA equivalents, nucleotide analogs and up to 10%, or even up to 20% base differences. The kit further contains a second primer that includes a 3' terminal target-complementary sequence up to 30 bases in length, and optionally a second primer upstream sequence that is not complementary to the target nucleic acid sequence that is to be amplified. The 3' terminal target-complementary sequence of the second primer includes 20 contiguous bases contained within SEQ ID NO:1, allowing for the presence of RNA and DNA equivalents, nucleotide analogs and up to 10%, or even up to 20% base differences. In a preferred embodiment, the first primer and the second primer are each up to 60 bases in length. In a different preferred embodiment, the 3' terminal target-complementary sequence of the first primer is up to 35 bases in length. In accordance with a first preferred version of this embodiment, the 3' terminal target-complementary sequence of the first primer is up to 24 bases in length. In accordance with a second preferred version of this embodiment, the 3, terminal target-complementary sequence of the second primer is up to 24 bases in length. In yet another preferred embodiment, when the 3' terminal target-complementary sequence of the first primer is up to 24 bases in length, the 3' terminal target-complementary sequence of the second primer is preferably up to 24 bases in length. In an alternative embodiment the 3' terminal target-complementary sequence of the second primer is up to 26 bases in length and includes 20 contiguous bases contained within SEQ ID NO:2, allowing for the presence of RNA and DNA equivalents, nucleotide analogs and up to 10%, or even up to 20% base differences. In accordance with a first preferred version of this embodiment, the 3, terminal target-complementary sequence of the first primer is up to 24 bases in length. In accordance with a second preferred version of this embodiment, the 3' terminal target-complementary sequence of the second primer is up to 24 bases in length. Preferably, the 3' terminal target-complementary sequence of the second primer is up to 24 bases in length. Still more preferably, the 3' terminal target-complementary sequence of the first primer is any one of SEQ ID NO:24, SEQ ID NO:25, SEQ ID NO:26 or SEQ ID NO:28. In certain embodiments wherein the 3' terminal target-complementary sequence of the first primer is up to 24 bases in length, and the 3' terminal target-complementary sequence of the second primer is up to 26 bases in length and includes 20 contiguous bases contained within SEQ ID NO:2, allowing for the presence of RNA and DNA equivalents, nucleotide analogs and up to 10%, or even up to 20% base differences, the 3' terminal target-complementary sequence of the second primer is any one of SEQ ID NO:10, SEQ ID NO:11, SEQ ID NO:12, SEQ ID NO:13, SEQ ID NO:14 or SEQ ID NO:15. Alternatively, when the 3' terminal target-complementary sequence of the first primer is any one of SEQ ID NO:24, SEQ ID NO:25, SEQ ID NO:26 or SEQ ID NO:28, the 3' terminal target-complementary sequence of the second primer may be any of SEQ ID NO:10, SEQ ID NO:11, SEQ ID NO:12, SEQ ID NO:13, SEQ ID NO:14 or SEQ ID NO:15. In accordance with a highly preferred embodiment, the first primer includes the first primer upstream sequence, such as a promoter sequence for T7 RNA polymerase.

Definitions

The following terms have the following meanings for the purpose of this disclosure, unless expressly stated to the contrary herein.

As used herein, a "biological sample" is any tissue or polynucleotide-containing material obtained from a human, animal or environmental sample. Biological samples in accordance with the invention include peripheral blood, plasma, serum or other body fluid, bone marrow or other organ, biopsy tissues or other materials of biological origin. A biological sample may be treated to disrupt tissue or cell structure, thereby releasing intracellular components into a solution which may contain enzymes, buffers, salts, detergents and the like.

As used herein, "polynucleotide" means either RNA or DNA, along with any synthetic nucleotide analogs or other molecules that may be present in the sequence and that do not prevent hybridization of the polynucleotide with a second molecule having a complementary sequence.

As used herein, a "detectable label" is a chemical species that can be detected or can lead to a detectable response. Detectable labels in accordance with the invention can be linked to polynucleotide probes either directly or indirectly, and include radioisotopes, enzymes, haptens, chromophores such as dyes or particles that impart a detectable color (e.g., latex beads or metal particles), luminescent compounds (e.g., bioluminescent, phosphorescent or chemiluminescent moieties) and fluorescent compounds.

A "homogeneous detectable label" refers to a label that can be detected in a homogeneous fashion by determining whether the label is on a probe hybridized to a target sequence. That is, homogeneous detectable labels can be detected without physically removing hybridized from unhybridized forms of the label or labeled probe. Homogeneous detectable labels are preferred when using labeled probes for detecting WNV nucleic acids. Examples of homogeneous labels have been described in detail by Arnold et al., U.S. Pat. No. 5,283,174; Woodhead et al., U.S. Pat. No. 5,656,207; and Nelson et al., U.S. Pat. No. 5,658,737. Preferred labels for use in homogenous assays include chemiluminescent compounds (e.g., see Woodhead et al., U.S. Pat. No. 5,656,207; Nelson et al., U.S. Pat. No. 5,658,737; and Arnold, Jr., et al., U.S. Pat. No. 5,639,604). Preferred chemiluminescent labels are acridinium ester ("AE") compounds, such as standard AE or derivatives thereof (e.g., naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE).

A "homogeneous assay" refers to a detection procedure that does not require physical separation of hybridized probe from non-hybridized probe prior to determining the extent of specific probe hybridization. Exemplary homogeneous assays, such as those described herein, can employ molecular beacons or other self-reporting probes which emit fluorescent signals when hybridized to an appropriate target, chemiluminescent acridinium ester labels which can be selectively destroyed by chemical means unless present in a hybrid duplex, and other homogeneously detectable labels that will be familiar to those having an ordinary level of skill in the art.

As used herein, "amplification" refers to an in vitro procedure for obtaining multiple copies of a target nucleic acid sequence, its complement or fragments thereof.

By "target nucleic acid" or "target" is meant a nucleic acid containing a target nucleic acid sequence In general, a target nucleic acid sequence that is to be amplified will be positioned between two oppositely disposed primers, and will include the portion of the target nucleic acid that is fully complementary to each of the primers.

By "target nucleic acid sequence" or "target sequence" or "target region" is meant a specific deoxyribonucleotide or ribonucleotide sequence comprising all or part of the nucleotide sequence of a single-stranded nucleic acid molecule, and the deoxyribonucleotide or ribonucleotide sequence complementary thereto.

By "transcription associated amplification" is meant any type of nucleic acid amplification that uses an RNA polymerase to produce multiple RNA transcripts from a nucleic acid template. One example of a transcription associated amplification method, called "Transcription Mediated Amplification" (TMA), generally employs an RNA polymerase, a DNA polymerase, deoxyribonucleoside triphosphates, ribonucleoside triphosphates, and a promoter-template complementary oligonucleotide, and optionally may include one or more analogous oligonucleotides. Variations of TMA are well known in the art as disclosed in detail in Burg et al., U.S. Pat. No. 5,437,990; Kacian et al., U.S. Pat. Nos. 5,399,491 and 5,554,516; Kacian et al., PCT No. WO 9322461; Gingeras et al., PCT No. WO 8801302; Gingeras et al., PCT No. WO 88/10315; Malek et al., U.S. Pat. No. 5,130,238; Urdea et al., U.S. Pat. Nos. 4,868,105 and 5,124,246; McDonough et al., PCT No. WO 9403472; and Ryder et al., PCT No. WO 9503430. The methods of Kacian et al. are preferred for conducting nucleic acid amplification procedures of the type disclosed herein.

As used herein, an "oligonucleotide" or "oligomer" is a polymeric chain of at least two, generally between about five and about 100, chemical subunits, each subunit comprising a nucleotide base moiety, a sugar moiety, and a linking moiety that joins the subunits in a linear spacial configuration. Common nucleotide base moieties are guanine (G), adenine (A), cytosine (C), thymine (T) and uracil (U), although other rare or modified nucleotide bases able to hydrogen bond are well known to those skilled in the art. Oligonucleotides may optionally include analogs of any of the sugar moieties, the base moieties, and the backbone constituents. Preferred oligonucleotides of the present invention fall in a size range of about 10 to about 100 residues. Oligonucleotides may be purified from naturally occurring sources, but preferably are synthesized using any of a variety of well known enzymatic or chemical methods.

As used herein, a "probe" is an oligonucleotide that hybridizes specifically to a target sequence in a nucleic acid, preferably in an amplified nucleic acid, under conditions that promote hybridization, to form a detectable hybrid. A probe optionally may contain a detectable moiety which either may be attached to the end(s) of the probe or may be internal. The nucleotides of the probe which combine with the target polynucleotide need not be strictly contiguous, as may be the case with a detectable moiety internal to the sequence of the probe.

Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). The "target" of a probe generally refers to a sequence contained within an amplified nucleic acid sequence which hybridizes specifically to at least a portion of a probe oligonucleotide using standard hydrogen bonding (i.e., base pairing). A probe may comprise target-specific sequences and optionally other sequences that are non-complementary to the target sequence that is to be detected. These non-complementary sequences may comprise a promoter sequence, a restriction endonuclease recognition site, or sequences that contribute to three-dimensional conformation of the probe (e.g., as described in Lizardi et al., U.S. Pat. Nos. 5,118,801 and 5,312,728). Sequences that are "sufficiently complementary" allow stable hybridization of a probe oligonucleotide to a target sequence that is not completely complementary to the probe's target-specific sequence.

As used herein, an "amplification primer" is an oligonucleotide that hybridizes to a target nucleic acid, or its complement, and participates in a nucleic acid amplification reaction. For example, amplification primers, or more simply "primers," may be optionally modified oligonucleotides which are capable of hybridizing to a template nucleic acid and which have a 3' end that can be extended by a DNA polymerase activity. In general, a primer will have a downstream WNV-complementary sequence, and optionally an upstream sequence that is not complementary to WNV nucleic acids. The optional upstream sequence may, for example, serve as an RNA polymerase promoter or contain restriction endonuclease cleavage sites.

By "substantially homologous," "substantially corresponding" or "substantially corresponds" is meant that the subject oligonucleotide has a base sequence containing an at least 10 contiguous base region that is at least 70% homologous, preferably at least 80% homologous, more preferably at least 90% homologous, and most preferably 100% homologous to an at least 10 contiguous base region present in a reference base sequence (excluding RNA and DNA equivalents). Those skilled in the art will readily appreciate modifications that could be made to the hybridization assay conditions at various percentages of homology to permit hybridization of the oligonucleotide to the target sequence while preventing unacceptable levels of non-specific hybridization. The degree of similarity is determined by comparing the order of nucleobases making up the two sequences and does not take into consideration other structural differences which may exist between the two sequences, provided the structural differences do not prevent hydrogen bonding with complementary bases. The degree of homology between two sequences can also be expressed in terms of the number of base mismatches present in each set of at least 10 contiguous bases being compared, which may range from 0-2 base differences.

By "substantially complementary" is meant that the subject oligonucleotide has a base sequence containing an at least 10 contiguous base region that is at least 70% complementary, preferably at least 80% complementary, more preferably at least 90% complementary, and most preferably 100% complementary to an at least 10 contiguous base region present in a target nucleic acid sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.) The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 10 contiguous bases being compared, which may range from 0-2 base mismatches.

By "sufficiently complementary" is meant a contiguous nucleic acid base sequence that is capable of hybridizing to another base sequence by hydrogen bonding between a series of complementary bases. Complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are preferably at least about 80%, more preferably at least about 90%, and most preferably about 1100% complementary to a sequence to which an oligonucleotide is intended to specifically hybridize. Appropriate hybridization conditions are well known to those skilled in the art, can be predicted readily based on base sequence composition, or can be determined empirically by using routine testing (e.g., See Sambrook et al., *Molecular Cloning, A Laboratory Manual,* $2^{nd}$ ed. (Cold Spring Harbor Laboratory Press, Cold Spring Harbor, N.Y., 1989) at §§1.90-1.91, 7.37-7.57, 9.47-9.51 and 11.47-11.57 particularly at §§9.50-9.51, 11.12-11.13, 11.45-11.47 and 11.55-11.57).

By "capture oligonucleotide" is meant at least one nucleic acid oligonucleotide that provides means for specifically joining a target sequence and an immobilized oligonucleotide due to base pair hybridization. A capture oligonucleotide preferably includes two binding regions: a target sequence-binding region and an immobilized probe-binding region, usually contiguous on the same oligonucleotide, although the capture oligonucleotide may include a target sequence-binding region and an immobilized probe-binding region which are present on two different oligonucleotides joined together by one or more linkers. For example, an immobilized probe-binding region may be present on a first oligonucleotide, the target sequence-binding region may be present on a second oligonucleotide, and the two different oligonucleotides are joined by hydrogen bonding with a linker that is a third oligonucleotide containing sequences that hybridize specifically to the sequences of the first and second oligonucleotides.

By "immobilized probe" or "immobilized nucleic acid" is meant a nucleic acid that joins, directly or indirectly, a capture oligonucleotide to an immobilized support. An immobilized probe is an oligonucleotide joined to a solid support that facilitates separation of bound target sequence from unbound material in a sample.

By "separating" or "purifying" is meant that one or more components of the biological sample are removed from one or more other components of the sample. Sample components include nucleic acids in a generally aqueous solution phase which may also include materials such as proteins, carbohydrates, lipids and labeled probes. Preferably, the separating or purifying step removes at least about 70%, more preferably at least about 90% and, even more preferably, at least about 95% of the other components present in the sample.

By "RNA and DNA equivalents" or "RNA and DNA equivalent bases" is meant molecules, such as RNA and DNA, having the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

By "consisting essentially of" is meant that additional component(s), composition(s) or method step(s) that do not materially change the basic and novel characteristics of the present invention may be included in the compositions or kits or methods of the present invention. Such characteristics include the ability to selectively detect WNV nucleic acids in biological samples such as whole blood or plasma. Any component(s), composition(s), or method step(s) that have a material effect on the basic and novel characteristics of the present invention would fall outside of this term.

DETAILED DESCRIPTION OF THE INVENTION

Figure 1:
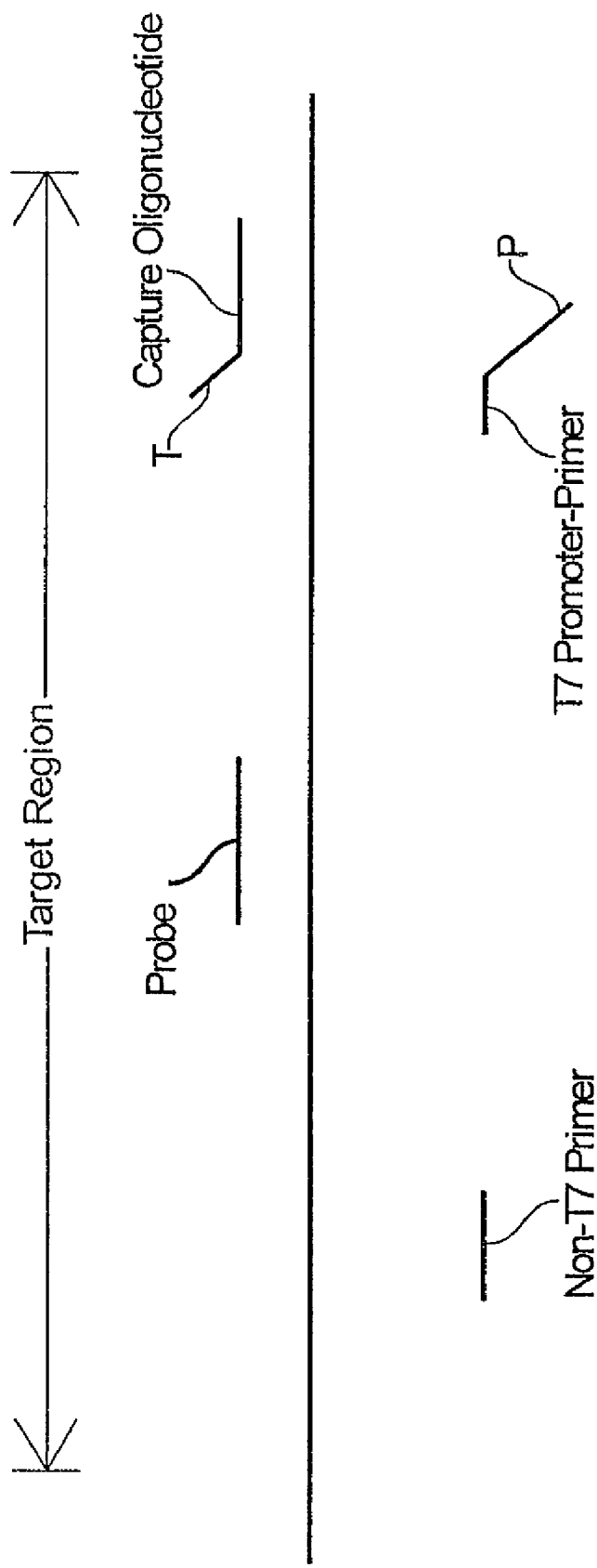
FIG. 1 is a schematic diagram illustrating the various polynucleotides that can be used for detecting a target region within the WNV nucleic acid (represented by a thick horizontal line). Positions of the following nucleic acids are shown relative to the target region: "Capture Oligonucleotide" refers to the nucleic acid used to hybridize to and capture the target nucleic acid prior to amplification, where "T" refers to a tail sequence used to hybridize an immobilized oligonucleotide having a complementary sequence (not shown); "Non-T7 Primer" and "P Promoter-Primer" represent two amplification primers used for conducting TMA, where "P" indicates the promoter sequence of the T7 promoter-primer; and "Probe" refers to the probe used for detecting amplified nucleic acid.

Disclosed herein are compositions, methods and kits for selectively detecting the nucleic acids of flaviviruses, such as West Nile virus (WNV), in biological samples such as blood, serum, plasma or other body fluid or tissue. The probes, primers and methods of the invention can be used either in diagnostic applications or for screening donated blood and blood products or other tissues that may contain infectious particles.

Introduction and Overview

The present invention includes compositions (nucleic acid capture oligonucleotides, amplification oligonucleotides and probes), methods and kits that are particularly useful for detecting WNV nucleic acids in a biological sample. To design oligonucleotide sequences appropriate for such uses, known WNV nucleic acid sequences were first compared to identify candidate regions of the viral genome that could serve as reagents in a diagnostic assay. As a result of these comparisons, three different regions of the WNV genome were selected as targets for detection using the capture oligonucleotides, primers and probes shown schematically in FIG. 1. Portions of sequences containing relatively few variants between the compared sequences were chosen as starting points for designing synthetic oligonucleotides suitable for use in capture, amplification and detection of amplified sequences.

Based on these analyses, the capture oligonucleotide, amplification primer and probe sequences presented below were designed. Those having an ordinary level of skill in the art will appreciate that any primer sequences specific for WNV or other flavivirus target, with or without a T7 promoter sequence, may be used as primers in the various primer-based in vitro amplification methods described below. It is also contemplated that oligonucleotides having the sequences disclosed herein could serve alternative functions in assays for detecting WNV nucleic acids. For example, the capture oligonucleotides disclosed herein could serve as hybridization probes, the hybridization probes disclosed herein could be used as amplification primers, and the amplification primers disclosed herein could be used as hybridization probes in alternative detection assays.

The amplification primers disclosed herein are particularly contemplated as components of multiplex amplification reactions wherein several amplicon species can be produced from an assortment of target-specific primers. For example, it is contemplated that certain preferred WNV-specific primers disclosed herein can be used in multiplex amplification reactions that are capable of amplifying polynucleotides of unrelated viruses without substantially compromising the sensitivities of those assays. Particular examples of these unrelated viruses include HIV-1, HIV-2, HCV and HBV.

Useful Amplification Methods

Amplification methods useful in connection with the present invention include: Transcription Mediated Amplification (TMA), Nucleic Acid Sequence-Based Amplification (NASBA), the Polymerase Chain Reaction (PCR), Strand Displacement Amplification (SDA), and amplification methods using self-replicating polynucleotide molecules and replication enzymes such as MDV-1 RNA and Q-beta enzyme. Methods for carrying out these various amplification techniques respectively can be found in U.S. Pat. No. 5,399,491, published European patent application EP 0 525 882, U.S. Pat. Nos. 4,965,188, 5,455,166, 5,472,840 and Lizardi et al., *BioTechnology* 6:1197 (1988). The disclosures of these documents which describe how to perform nucleic acid amplification reactions are hereby incorporated by reference.

In a highly preferred embodiment of the invention, WNV nucleic acid sequences are amplified using a TMA protocol. According to this protocol, the reverse transcriptase which provides the DNA polymerase activity also possesses an endogenous RNase H activity. One of the primers used in this procedure contains a promoter sequence positioned upstream of a sequence that is complementary to one strand of a target nucleic acid that is to be amplified. In the first step of the amplification, a promoter-primer hybridizes to the WNV target RNA at a defined site. Reverse transcriptase creates a complementary DNA copy of the target RNA by extension from the 3' end of the promoter-primer. Following interaction of an opposite strand primer with the newly synthesized DNA strand, a second strand of DNA is synthesized from the end of the primer by reverse transcriptase, thereby creating a double-stranded DNA molecule. RNA polymerase recognizes the promoter sequence in this double-stranded DNA template and initiates transcription. Each of the newly synthesized RNA amplicons re-enters the TMA process and serves as a template for a new round of replication, thereby leading to an exponential expansion of the RNA amplicon. Since each of the DNA templates can make 100-1000 copies of RNA amplicon, this expansion can result in the production of 10 billion amplicons in less than one hour. The entire process is autocatalytic and is performed at a constant temperature.

Structural Features of Primers

As indicated above, a "primer" refers to an optionally modified oligonucleotide which is capable of participating in a nucleic acid amplification reaction. Preferred primers are capable of hybridizing to a template nucleic acid and which has a 3' end that can be extended by a DNA polymerase activity. The 5' region of the primer may be non-complementary to the target nucleic acid. If the 5' non-complementary region includes a promoter sequence, it is referred to as a "promoter-primer." Those skilled in the art will appreciate that any oligonucleotide that can function as a primer (i.e., an oligonucleotide that hybridizes specifically to a target sequence and has a 3' end capable of extension by a DNA polymerase activity) can be modified to include a 5' promoter sequence, and thus could function as a promoter-primer. Similarly, any promoter-primer can be modified by removal of, or synthesis without, a promoter sequence and still function as a primer.

Nucleotide base moieties of primers may be modified (e.g., by the addition of propyne groups), as long as the modified base moiety retains the ability to form a non-covalent association with G, A, C, T or U, and as long as an oligonucleotide comprising at least one modified nucleotide base moiety or analog is not sterically prevented from hybridizing with a single-stranded nucleic acid. As indicated below in connection with the chemical composition of useful probes, the nitrogenous bases of primers in accordance with the invention may be conventional bases (A, G, C, T, U), known analogs thereof (e.g., inosine or "I" having hypoxanthine as its base moiety; see *The Biochemistry of the Nucleic Acids* 5-36, Adams et al., ed., $11^{th}$ ed., 1992), known derivatives of purine or pyrimidine bases (e.g., $N^4$-methyl deoxygaunosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines (see, Cook, PCT Int'l Pub. No. WO 93/13121) and "abasic" residues where the backbone includes no nitrogenous base for one or more residues of the polymer (see Arnold et al., U.S. Pat. No. 5,585,481). Common sugar moieties that comprise the primer backbone include ribose and deoxyribose, although 2'-O-methyl ribose (OMe), halogenated sugars, and other modified sugar moieties may also be used. Usually, the linking group of the primer backbone is a phosphorus-containing moiety, most commonly a phosphodiester linkage, although other linkages, such as, for example, phosphorothioates, methylphosphonates, and non-phosphorus-containing linkages such as peptide-like linkages found in "peptide nucleic acids" (PNA) also are intended for use in the assay disclosed herein.

Useful Probe Labeling Systems and Detectable Moieties

Essentially any labeling and detection system that can be used for monitoring specific nucleic acid hybridization can be used in conjunction with the present invention. Included among the collection of useful labels are radiolabels, enzymes, haptens, linked oligonucleotides, chemiluminescent molecules, fluorescent moieties (either alone or in combination with "quencher" moieties), and redox-active moieties that are amenable to electronic detection methods.

Preferred chemiluminescent molecules include acridinium esters of the type disclosed by Arnold et al., in U.S. Pat. No. 5,283,174 for use in connection with homogenous protection assays, and of the type disclosed by Woodhead et al., in U.S. Pat. No. 5,656,207 for use in connection with assays that quantify multiple targets in a single reaction. The disclosures contained in these patent documents are hereby incorporated by reference. Preferred electronic labeling and detection approaches are disclosed in U.S. Pat. Nos. 5,591,578 and 5,770,369, and the published international patent application WO 98/57158, the disclosures of which are hereby incorporated by reference. Redox active moieties useful as labels in the present invention include transition metals such as Cd, Mg, Cu, Co, Pd, Zn, Fe and Ru.

Particularly preferred detectable labels for probes in accordance with the present invention are detectable in homogeneous assay systems (i.e., where, in a mixture, bound labeled probe exhibits a detectable change, such as stability or differential degradation, compared to unbound labeled probe). While other homogeneously detectable labels, such as fluorescent labels and electronically detectable labels, are intended for use in the practice of the present invention, a preferred label for use in homogenous assays is a chemiluminescent compound (e.g., as described by Woodhead et al., in U.S. Pat. No. 5,656,207; by Nelson et al., in U.S. Pat. No. 5,658,737; or by Arnold et al., in U.S. Pat. No. 5,639,604). Particularly preferred chemiluminescent labels include acridinium ester ("AE") compounds, such as standard AE or derivatives thereof, such as naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AR.

In some applications, probes exhibiting at least some degree of self-complementarity are desirable to facilitate detection of probe:target duplexes in a test sample without first requiring the removal of unhybridized probe prior to detection. By way of example, structures referred to as "Molecular Torches" are designed to include distinct regions of self-complementarity (coined "the target binding domain" and "the target closing domain") which are connected by a joining region and which hybridize to one another under predetermined hybridization assay conditions. When exposed to denaturing conditions, the two complementary regions (which may be fully or partially complementary) of the Molecular Torch melt, leaving the target binding domain available for hybridization to a target sequence when the predetermined hybridization assay conditions are restored. Molecular Torches are designed so that the target binding domain favors hybridization to the target sequence over the target closing domain. The target binding domain and the target closing domain of a Molecular Torch include interacting labels (e.g., fluorescent/quencher) positioned so that a different signal is produced when the Molecular Torch is self-hybridized as opposed to when the Molecular Torch is hybridized to a target nucleic acid, thereby permitting detection of probe:target duplexes in a test sample in the presence of unhybridized probe having a viable label associated therewith. Molecular Torches are fully described in U.S. Pat. No. 6,361,945, the disclosure of which is hereby incorporated by reference.

Another example of a self-complementary hybridization assay probe that may be used in conjunction with the invention is a structure commonly referred to as a "Molecular Beacon." Molecular Beacons comprise nucleic acid molecules having a target complementary sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular Beacons are fully described in U.S. Pat. No. 5,925,517, the disclosure of which is hereby incorporated by reference. Molecular beacons useful for detecting WNV-specific nucleic acid sequences may be created by appending to either end of one of the probe sequences disclosed herein, a first nucleic acid arm comprising a fluorophore and a second nucleic acid arm comprising a quencher moiety. In this configuration, the WNV-specific probe sequence disclosed herein serves as the target-complementary "loop" portion of the resulting molecular beacon.

Molecular beacons preferably are labeled with an interactive pair of detectable labels. Examples of detectable labels that are preferred as members of an interactive pair of labels interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

When two labels are held sufficiently close that energy emitted by one label can be received or absorbed by the second label, whether by a FRET or non-FRET mechanism, the two labels are said to be in "energy transfer relationship" with each other. This is the case, for example, when a molecular beacon is maintained in the closed state by formation of a stem duplex, and fluorescent emission from a fluorophore attached to one arm of the probe is quenched by a quencher moiety on the opposite arm.

Highly preferred label moieties for the invented molecular beacons include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are preferably due to FRET, or to radiative energy transfer or non-FRET modes. When a molecular beacon having a pair of interactive labels in the closed state is stimulated by an appropriate frequency of light, a fluorescent signal is generated at a first level, which may be very low. When this same probe is in the open state and is stimulated by an appropriate frequency of light, the fluorophore and the quencher moieties are sufficiently separated from each other that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the molecular beacon is only "on" in the "open" conformation and indicates that the probe is bound to the target by emanating an easily detectable signal. The conformational state of the probe alters the signal generated from the probe by regulating the interaction between the label moieties.

Examples of donor/acceptor label pairs that may be used in connection with the invention, making no attempt to distinguish FRET from non-FRET pairs, include fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation. Preferred fluorophore moieties that can be used as one member of a donor-acceptor pair include fluorescein, ROX, and the CY dyes (such as CY5). Highly preferred quencher moieties that can be used as another member of a donor-acceptor pair include DABCYL and the BLACK HOLE QUENCHER moieties which are available from Biosearch Technologies, Inc., (Novato, Calif.).

Synthetic techniques and methods of bonding labels to nucleic acids and detecting labels are well known in the art (e.g., see Sambrook et al., *Molecular Cloning, A Laboratory Manual*, 2nd ed. (Cold Spring Harbor Laboratory Press, Cold Spring Harbor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; Kourilsky et al., U.S. Pat. No. 4,581,333), and Becker et al., European Patent App. No. 0 747 706.

Chemical Composition of Probes

Probes in accordance with the invention comprise polynucleotides or polynucleotide analogs and optionally may carry a detectable label covalently bonded thereto. Nucleosides or nucleoside analogs of the probe comprise nitrogenous heterocyclic bases, or base analogs, where the nucleosides are linked together, for example by phosphodiester bonds to form a polynucleotide. Accordingly, a probe may comprise conventional ribonucleic acid (RNA) and/or deoxyribonucleic acid (DNA), but also may comprise chemical analogs of these molecules. The "backbone" of a probe may be made up of a variety of linkages known in the art, including one or more sugar-phosphodiester linkages, peptide-nucleic acid bonds (sometimes referred to as "peptide nucleic acids" as described by Hyldig-Nielsen et al., PCT Int'l Pub. No. WO 9532305), phosphorothioate linkages, methylphosphonate linkages or combinations thereof. Sugar moieties of the probe may be either ribose or deoxyribose, or similar compounds having known substitutions, such as, for example, 2'-O-methyl ribose and 2' halide substitutions (e.g., 2'-F). The nitrogenous bases may be conventional bases (A, G, C, T, U), known analogs thereof (e.g., inosine or "I"; see *The Biochemistry of the Nucleic Acids* 5-36, Adams et al., ed., 11$^{th}$ ed., 1992), known derivatives of purine or pyrimidine bases (e.g., $N^4$-methyl deoxygaunosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines (see, Cook, PCT Int'l Pub. No. WO 93/13121) and "abasic" residues where the backbone includes no nitrogenous base for one or more residues of the polymer (see Arnold et al., U.S. Pat. No. 5,585,481). A probe may comprise only conventional sugars, bases and linkages found in RNA and DNA, or may include both conventional components and substitutions (e.g., conventional bases linked via a methoxy backbone, or a nucleic acid including conventional bases and one or more base analogs).

While oligonucleotide probes of different lengths and base composition may be used for detecting WNV nucleic acids, preferred probes in this invention have lengths of up to 100 nucleotides, and more preferably have lengths of up to 60 nucleotides. Preferred length ranges for the invented oligonucleotides are from 10 to 100 bases in length, or more preferably between 15 and 50 bases in length, or still more preferably between 15 and 30 bases in length. However, the specific probe sequences described below also may be provided in a nucleic acid cloning vector or transcript or other longer nucleic acid and still can be used for detecting WNV nucleic acids.

Selection of Amplification Primers and Detection Probes Specific for WNV

Useful guidelines for designing amplification primers and probes with desired characteristics are described herein. The optimal sites for amplifying and probing WNV nucleic acids contain two, and preferably three, conserved regions each greater than about 15 bases in length, within about 200 bases of contiguous sequence. The degree of amplification observed with a set of primers or promoter-primers depends on several factors, including the ability of the oligonucleotides to hybridize to their complementary sequences and their ability to be extended enzymatically. Because the extent and specificity of hybridization reactions are affected by a number of factors, manipulation of those factors will determine the exact sensitivity and specificity of a particular oligonucleotide, whether perfectly complementary to its target or not. The effects of varying assay conditions are known to those skilled in the art, and are described by Hogan et al., in U.S. Pat. No. 5,840,488, the disclosure of which is hereby incorporated by reference.

The length of the target nucleic acid sequence and, accordingly, the length of the primer sequence or probe sequence can be important. In some cases, there may be several sequences from a particular target region, varying in location and length, which will yield primers or probes having the desired hybridization characteristics. While it is possible for nucleic acids that are not perfectly complementary to hybridize, the longest stretch of perfectly homologous base sequence will normally primarily determine hybrid stability.

Amplification primers and probes should be positioned to minimize the stability of the oligonucleotide:nontarget (i.e., nucleic acid with similar sequence to target nucleic acid) nucleic acid hybrid. It is preferred that the amplification primers and detection probes are able to distinguish between target and non-target sequences. In designing primers and probes, the differences in these Tm values should be as large as possible (e.g., at least 2° C. and preferably 5° C.).

The degree of non-specific extension (primer-dimer or non-target copying) can also affect amplification efficiency. For this reason, primers are selected to have low self- or cross-complementarity, particularly at the 3' ends of the sequence. Long homopolymer tracts and high CC content are avoided to reduce spurious primer extension. Commercially available computer software can aid in this aspect of the design. Available computer programs include MacDNA-SIS™ 2.0 (Hitachi Software Engineering American Ltd.) and OLIGO ver. 6.6 (Molecular Biology Insights; Cascade, Colo.).

Those having an ordinary level of skill in the art will appreciate that hybridization involves the association of two single strands of complementary nucleic acid to form a hydrogen bonded double strand. It is implicit that if one of the two strands is wholly or partially involved in a hybrid, then that strand will be less able to participate in formation of a new hybrid. By designing primers and probes so that substantial portions of the sequences of interest are single stranded, the rate and extent of hybridization may be greatly increased. If the target is an integrated genomic sequence, then it will naturally occur in a double stranded form (as is the case with the product of the polymerase chain reaction). These double-stranded targets are naturally inhibitory to hybridization with a probe and require denaturation prior to the hybridization step.

The rate at which a polynucleotide hybridizes to its target is a measure of the thermal stability of the target secondary structure in the target binding region. The standard measurement of hybridization rate is the $C_0t^{1/2}$ which is measured as moles of nucleotide per liter multiplied by seconds. Thus, it is the concentration of probe multiplied by the time at which 50% of maximal hybridization occurs at that concentration. This value is determined by hybridizing various amounts of polynucleotide to a constant amount of target for a fixed time. The $C_0t^{1/2}$ is found graphically by standard procedures familiar to those having an ordinary level of skill in the art.

Preferred Amplification Primers

Primers useful for conducting amplification reactions can have different lengths to accommodate the presence of extraneous sequences that do not participate in target binding, and that may not substantially affect amplification or detection procedures. For example, promoter-primers useful for performing amplification reactions in accordance with the invention have at least a minimal sequence that hybridizes to the WNV target nucleic acid, and a promoter sequence positioned upstream of that minimal sequence. However, insertion of sequences between the target binding sequence and the promoter sequence could change the length of the primer without compromising its utility in the amplification reaction. Additionally, the lengths of the amplification primers and detection probes are matters of choice as long as the sequences of these oligonucleotides conform to the minimal essential requirements for hybridizing the desired complementary sequence.

Tables 1 and 2 present specific examples of oligonucleotide sequences that were used as primers for amplifying WNV nucleic acids in the 5' non-coding region. Table 1 presents the sequences of primers that were complementary to WNV sequences on one strand of nucleic acid. All of the illustrative primers presented in Table 1 have target-complementary sequences contained within the sequence of SEQ ID NO:1. Different subsets of preferred primers have target-complementary sequences contained within the sequence of SEQ ID NO:2 or SEQ ID NO:3. It is preferred for one of the primers used in the amplification procedure to have a target-complementary sequence falling within one of these domains. Table 2 presents the sequences of both the WNV target-complementary primers and the full sequences for promoter-primers that were used during development of the invention. All of the illustrative primers presented in Table 2 have target-complementary sequences contained within the sequence of SEQ ID NO:16, a feature which is presently preferred for one of the primers used in the amplification procedure. Notably, the oligonucleotide sequences in Table 1 and Table 2 are complementary to opposite strands of the WNV nucleic acid.

Primers useful for amplifying the 5' non-coding region of WNV can include nucleotide analogs. For example, the primers of SEQ ID NO:4 and SEQ ID NO:5 differ from each other by the substitution of a hypoxanthine base analog for an adenine base at position 11. Similarly, the primers of SEQ ID NO:6 and SEQ ID NO:7 also differ by the presence of this base analog, as do the opposite strand primers identified by SEQ ID NO:21 and SEQ ID NO:22. This illustrates how nucleobases in the primers may be substituted by modified bases or nucleobase analogs.

TABLE 1

Polynucleotide Sequences of Amplification Primers

| Sequence | SEQ ID NO: |
|---|---|
| CAATTAACACAGTGCGAGCTGTTT | SEQ ID NO: 4 |
| CAATTAACACIGTGCGAGCTGTTT | SEQ ID NO: 5 |
| TAACACAGTGCGAGCTGTTTCTT | SEQ ID NO: 6 |
| TAACACIGTGCGAGCTGTTTCTT | SEQ ID NO: 7 |
| CGAGCTGTTTCTTAGCACGA | SEQ ID NO: 8 |
| CGAGCTGTTTCTTAGCACGAA | SEQ ID NO: 9 |
| GAAGATCTCGATGTCTAAGAAACC | SEQ ID NO: 10 |
| AAGATCTCGATGTCTAAGAAACC | SEQ ID NO: 11 |
| AGATCTCGATGTCTAAGAAACC | SEQ ID NO: 12 |
| GATCTCGATGTCTAAGAAACCA | SEQ ID NO: 13 |
| GATCTCGATGTCTAAGAAACC | SEQ ID NO: 14 |
| ATCTCGATGTCTAAGAAACCAG | SEQ ID NO: 15 |

Table 2 presents WNV target-complementary oligonucleotide sequences and the corresponding promoter-primer sequences that were used for amplifying WNV nucleic acid sequences in the 5' non-coding region of the viral genome. As indicated above, all promoter-primers included sequences complementary to a WNV target sequence at their 3' ends, and a T7 promoter sequence at their 5' ends. Primers identified by SEQ ID Nos:29-40 in Table 2 are promoter-primers corresponding to the WNV-complementary primers identified as SEQ ID Nos:17-28, respectively.

TABLE 2

Polynucleotide Sequences of Amplification Primers

| Sequence | SEQ ID NO: |
|---|---|
| GTTTTAGCATATTGACAGCCC | SEQ ID: 17 |
| GTTTTAGCATATTGACAGCC | SEQ ID: 18 |
| TTCCGCGTTTTAGCATATTGA | SEQ ID: 19 |
| ATTCCGCGTTTTAGCATATTG | SEQ ID: 20 |
| ATCAAGGACAACACGCGGGGCAT | SEQ ID: 21 |
| ATCAAGGACAAIACGCGGGGCAT | SEQ ID: 22 |
| CCTCTTCAGTCCAATCAAGGACAA | SEQ ID: 23 |
| AGCCCTCTTCAGTCCAATCAAGGA | SEQ ID: 24 |
| TAGCCCTCTTCAGTCCAATCAAGG | SEQ ID: 25 |
| ATAGCCCTCTTCAGTCCAATCAAG | SEQ ID: 26 |
| TAGCCCTCTTCAGTCCAATCAA | SEQ ID: 27 |
| ACATAGCCCTCTTCAGTCCAATCA | SEQ ID: 28 |
| AATTTAATACGACTCACTATAGGGAGAGTTTTAGCATATTGACAGCCC | SEQ ID: 29 |
| AATTTAATACGACTCACTATAGGGAGAGTTTTAGCATATTGACAGCC | SEQ ID: 30 |
| AATTTAATACGACTCACTATAGGGAGATTCCGCGTTTTAGCATATTGA | SEQ ID: 31 |
| AATTTAATACGACTCACTATAGGGAGAATTCCGCGTTTTAGCATATTG | SEQ ID: 32 |
| AATTTAATACGACTCACTATAGGGAGAATCAAGGACAACACGCGGGGC | SEQ ID: 33 |
| AATTTAATACGACTCACTATAGGGAGAATCAAGGACAAIACGCGGGGC | SEQ ID: 34 |
| AATTTAATACGACTCACTATAGGGAGACCTCTTCAGTCCAATCAAGGA | SEQ ID: 35 |
| AATTTAATACGACTCACTATAGGGAGAAGCCCTCTTCAGTCCAATCAA | SEQ ID: 36 |
| AATTTAATACGACTCACTATAGGGAGATAGCCCTCTTCAGTCCAATCA | SEQ ID: 37 |
| AATTTAATACGACTCACTATAGGGAGAATAGCCCTCTTCAGTCCAATC | SEQ ID: 38 |
| AATTTAATACGACTCACTATAGGGAGATAGCCCTCTTCAGTCCAAT | SEQ ID: 39 |
| AATTTAATACGACTCACTATAGGGAGAACATAGCCCTCTTCAGTCC | SEQ ID: 40 |

Preferred sets of primers for amplifying WNV sequences in the 5'non-coding region include a first primer that hybridizes a WNV target sequence (such as one of the primers listed in Table 2) and a second primer that is complementary to the sequence of an extension product of the first primer (such as one of the primer sequences listed in Table 1). In a highly preferred embodiment, the first primer is a promoter-primer that includes a T7 promoter sequence at its 5' end.

Tables 3 and 4 present specific examples of oligonucleotide sequences that were used as primers for amplifying WNV nucleic acids in the 3000 region of the viral genome. Table 3 presents the sequences of primers that were complementary to WNV sequences on one strand of nucleic acid. All of the illustrative primers presented in Table 3 have target-complementary sequences contained within the sequence of SEQ ID NO:41, a feature which is presently preferred for one of the primers used in the amplification procedure. Table 4 presents the sequences of both the WNV target-complementary primers and the full sequences for promoter-primers that were used during development of the invention. All of the illustrative primers presented in Table 4 have target-complementary sequences contained within the sequence of SEQ ID NO:52, a feature which is presently preferred for one of the primers used in the amplification procedure. Notably, the oligonucleotide sequences in Table 3 and Table 4 are complementary to opposite strands of the WNV nucleic acid.

Primers useful for amplifying the 3000 region of WNV can include nucleotide analogs. For example, the primers of SEQ ID NO:42, SEQ ID NO:47 and SEQ ID NO:48 differ from each other by the substitution of a hypoxanthine base analog for the existing base at different individual positions within the primer sequence. Similarly, the primers of SEQ ID NO:43 and SEQ ID NO:49 also differ by the presence of this base analog, as do the primers identified by SEQ ID NO:45 and SEQ ID NO:50 and SEQ ID NO:51. This illustrates that nucleobases in the primers may be substituted by modified bases or nucleobase analogs.

TABLE 3

Polynucleotide Sequences of Amplification Primers

| Sequence | SEQ ID NO: |
|---|---|
| TTGACCCTTTTCAGTTGGGCCTT | SEQ ID NO: 42 |
| CTTTTCAGTTGGGCCTTCTGGT | SEQ ID NO: 43 |
| AGTTGGGCCTTCTGGTCGTGTT | SEQ ID NO: 44 |
| TGGTCGTGTTCTTGGCCACCCA | SEQ ID NO: 45 |
| TCGTGTTCTTGGCCACCCAGGA | SEQ ID NO: 46 |
| TTGAICCTTTTCAGTTGGGCCTT | SEQ ID NO: 47 |
| TTGACCCTTTTCAGITGGGCCTT | SEQ ID NO: 48 |
| CTTTTCAGITGGGCCTTCTGGT | SEQ ID NO: 49 |
| TGGTCGTGTTITTGGCCACCCA | SEQ ID NO: 50 |
| TGGTCGTGTTCITGGCCACCCA | SEQ ID NO: 51 |

Table 4 presents WNV target-complementary oligonucleotide sequences and the corresponding promoter-primer sequences that were used for amplifying WNV nucleic acid sequences in the 3000 region of the viral genome. As indicated above, all promoter-primers included sequences complementary to a WNV target sequence at their 3' ends, and a T7 promoter sequence at their 5' ends.

TABLE 4

Polynucleotide Sequences of Amplification Primers

| Identifier | Sequence | SEQ ID NO: |
|---|---|---|
| WNV complementary primer | CTGGCATGCTGATCTTGGCTGT | SEQ ID NO: 53 |
| WNV complementary primer | ATAGCTGGCATGCTGATCTTGGC | SEQ ID NO: 54 |
| WNV complementary primer | ATAGCTGGCATGCTGATCTTGG | SEQ ID NO: 55 |
| T7 promoter-primer | AATTTAATACGACTCACTATAGGG AGACTGGCATGCTGATCTTGGCTG | SEQ ID NO: 56 |
| T7 promoter-primer | AATTTAATACGACTCACTATAGGG | SEQ ID NO: 57 |
| T7 promoter-primer | AATTTAATACGACTCACTATAGGG | SEQ ID NO: 58 |

Preferred sets of primers for amplifying WNV sequences in the 3000 region of the viral genome include a first primer that hybridizes a WNV target sequence (such as one of the primers listed in Table 4) and a second primer that is complementary to the sequence of an extension product of the first primer (such as one of the primer sequences listed in Table 3). In a highly preferred embodiment, the first primer is a promoter-primer that includes a T7 promoter sequence at its 5' end.

Tables 5 and 6 present specific examples of oligonucleotide sequences that were used as primers for amplifying WNV nucleic acids in the 3' non-coding region of the viral genome. Table 5 presents the sequences of primers that were complementary to WNV sequences on one strand of nucleic acid. All of the illustrative primers presented in Table 5 have target-complementary sequences contained within the sequence of SEQ ID NO:59, a feature which is presently preferred for one of the primers used in the amplification procedure. Table 6 presents the sequences of both the WNV target-complementary primers and the full sequences for promoter-primers that were used during development of the invention. All of the illustrative primers presented in Table 6 have target-complementary sequences contained within the sequence of SEQ ID NO:72. Different subsets of preferred primers have target-complementary sequences contained within the sequence of SEQ ID NO:73 or SEQ ID NO:74. It is preferred for one of the primers used in the amplification procedure to have a target-complementary sequence falling within one of these domains. Notably, the oligonucleotide sequences in Table 5 and Table 6 are complementary to opposite strands of the WNV nucleic acid.

Primers useful for amplifying the 3' non-coding region of WNV can include nucleotide analogs. For example, the primers of SEQ ID NO:60 and SEQ ID NO:61 differ from each other by the substitution of a hypoxanthine base analog for a thymine base at position 1. Similarly, the primers of SEQ ID NO:64 and SEQ ID NO:65 also differ by the presence of this base analog, in this instance substituting for cytosine. Likewise, the WNV-complementary primer sequences of SEQ ID NO:83 and SEQ ID NO:82, together with the corresponding promoter-primer sequences, also contain hypoxanthine base analog substitutions. This further illustrates that nucleobases in the primers may be substituted by modified bases or nucleobase analogs.

TABLE 5

Polynucleotide Sequences of Amplification Primers

| Sequence | SEQ ID NO: |
|---|---|
| TCCGCCACCGGAAGTTGAG | SEQ ID NO: 60 |
| ICCGCCACCGGAAGTTGAG | SEQ ID NO: 61 |
| TCCGCCACCGGAAGTTGAGT | SEQ ID NO: 62 |
| TCCGCCACCGGAAGTTGAGTA | SEQ ID NO: 63 |
| CGCCACCGGAAGTTGAGT | SEQ ID NO: 64 |
| IGCCACCGGAAGTTGAGT | SEQ ID NO: 65 |
| CGCCACCGGAAGTTGAGTA | SEQ ID NO: 66 |
| GGAAGTTGAGTAGACGGTGCT | SEQ ID NO: 67 |
| GGAAGTTGAGTAGACGGTGCTG | SEQ ID NO: 68 |
| GAAGTTGAGTAGACGGTGCT | SEQ ID NO: 69 |
| GAAGTTGAGTAGACGGTGCTG | SEQ ID NO: 70 |
| AAGTTGAGTAGACGGTGCTG | SEQ ID NO: 71 |

Table 6 presents WNV target-complementary oligonucleotide sequences and the corresponding promoter-primer sequences that were used for amplifying WNV nucleic acid sequences in the 3' non-coding region of the viral genome. As indicated above, all promoter-primers included sequences complementary to a WNV target sequence at their 3' ends, and a T7 promoter sequence at their 5' ends.

TABLE 6

Polynucleotide Sequences of Amplification Primers

| Sequence | SEQ ID NO: |
|---|---|
| TCCGAGACGGTTCTGAGGGCTTAC | SEQ ID NO: 75 |
| TCCGAGACGGTTCTGAGGGCTTA | SEQ ID NO: 76 |
| TCCGAGACGGTTCTGAGGGCTT | SEQ ID NO: 77 |
| CCAGTCCTCCTGGGGTTGAG | SEQ ID NO: 78 |
| ACCCAGTCCTCCTGGGGTTGAG | SEQ ID NO: 79 |
| ACCCAGTCCTCCTGGGGTTGA | SEQ ID NO: 80 |
| ACCCAGTCCTCCTGGGGTTG | SEQ ID NO: 81 |
| GCTACAICAIGTGGGGTCCT | SEQ ID NO: 82 |
| GCTACAACAIGTGGGGTCCT | SEQ ID NO: 83 |
| AATTTAATACGACTCACTATAGGGAGATCCGAGACGGTTCTGAGGGCTTAC | SEQ ID NO: 84 |
| AATTTAATACGACTCACTATAGGGAGATCCGAGACGGTTCTGAGGGCTTA | SEQ ID NO: 85 |
| AATTTAATACGACTCACTATAGGGAGATCCGAGACGGTTCTGAGGGCTT | SEQ ID NO: 86 |
| AATTTAATACGACTCACTATAGGGAGACCAGTCCTCCTGGGGTTGAG | SEQ ID NO: 87 |
| AATTTAATACGACTCACTATAGGGAGAACCCAGTCCTCCTGGGGTTGAG | SEQ ID NO: 88 |
| AATTTAATACGACTCACTATAGGGAGAACCCAGTCCTCCTGGGGTTGA | SEQ ID NO: 89 |
| AATTTATACGACTCACTATAGGGAGAACCCAGTCCTCCTGGGGTTG | SEQ ID NO: 90 |
| AATTTAATACGACTCACTATAGGGAGAGCTACAICAIGTGGGGTCCT | SEQ ID NO: 91 |
| AATTTAATACGACTCACTATAGGGAGAGCTACAACAIGTGGGGTCCT | SEQ ID NO: 92 |

Preferred sets of primers for amplifying WNV sequences in the 3' non-coding region include a first primer that hybridizes a WNV target sequence (such as one of the primers listed in Table 6) and a second primer that is complementary to the sequence of an extension product of the first primer (such as one of the primer sequences listed in Table 5). In a highly preferred embodiment, the first primer is a promoter-primer that includes a T7 promoter sequence at its 5' end. Primers identified by SEQ ID Nos:84-92 in Table 6 are promoter-primers corresponding to the WNV-complementary primers identified as SEQ ID Nos:75-83, respectively.

Preferred Detection Probes

Another aspect of the invention relates to oligonucleotides that can be used as hybridization probes for detecting WNV nucleic acids. Methods for amplifying a target nucleic acid sequence present in the nucleic acid of WNV can include an optional further step for detecting amplicons. This procedure for detecting WNV nucleic acids includes a step for contacting a test sample with a hybridization assay probe that preferentially hybridizes to the target nucleic acid sequence, or the complement thereof, under stringent hybridization conditions, thereby forming a probe:target duplex that is stable for detection. Next there is a step for determining whether the hybrid is present in the test sample as an indication of the presence or absence of WNV nucleic acids in the test sample. This may involve detecting the probe:target duplex, and preferably involve homogeneous assay systems.

Hybridization assay probes useful for detecting WNV nucleic acid sequences include a sequence of bases substantially complementary to a WNV target nucleic acid sequence. Thus, probes of the invention hybridize one strand of a WNV target nucleic acid sequence, or the complement thereof. These probes may optionally have additional bases outside of the targeted nucleic acid region which may or may not be complementary to WNV nucleic acid.

Preferred probes are sufficiently homologous to the target nucleic acid to hybridize under stringent hybridization conditions corresponding to about 60° C. when the salt concentration is in the range of 0.6-0.9 M. Preferred salts include lithium chloride, but other salts such as sodium chloride and sodium citrate also can be used in the hybridization solution. Example high stringency hybridization conditions are alternatively provided by 0.48 M sodium phosphate buffer, 0.1% sodium dodecyl sulfate, and 1 mM each of EDTA and EGTA, or by 0.6 M LiCl, 1% lithium lauryl sulfate, 60 mM lithium succinate and 10 mM each of EDTA and EGTA.

Probes in accordance with the invention have sequences complementary to, or corresponding to one of three different domains of the WNV genome. As reiterated below, these domains were: (1) the 5' non-coding region/capsid region, (2) the 3000 region, and (3) the 3' non-coding region. Certain probes that are preferred for detecting WNV nucleic acid sequences have a probe sequence, which includes the target-complementary sequence of bases together with any base sequences that are not complementary to the nucleic acid that is to be detected, in the length range of from 10-100 nucleotides. Certain specific probes that are preferred for detecting WNV nucleic acid sequences have target-complementary sequences in the length range of from 12-87, from 10-20, from 13-37 or from 17-23 nucleotides. Of course, these target-complementary sequences may be linear sequences, or may be contained in the structure of a molecular beacon or other construct having one or more optional nucleic acid sequences that are non-complementary to the WNV target sequence that is to be detected. As indicated above, probes may be made of DNA, RNA, a combination DNA and RNA, a nucleic acid analog, or contain one or more modified nucleosides (e.g., a ribonucleoside having a 2'-O-methyl substitution to the ribofuranosyl moiety).

Simply stated, preferred probes for detecting target nucleic acids of interest in connection with the present invention include sequences that are contained within one or more of several defined probe domains or the complements thereof, allowing for the presence of RNA and DNA equivalents, nucleotide analogs, up to 10% mismatched bases, and even up to 20% mismatched bases. For example, preferred hybridization assay probes for detecting flaviviral nucleic acids, such as the nucleic acids of WNV, in the 5 non-coding region can include target-complementary sequences of bases contained within the sequence of SEQ ID NO:93, or within one of the subdomains defined by SEQ ID NO:94 or SEQ ID NO:95. Preferred hybridization assay probes for detecting flaviviral nucleic acids, such as the nucleic acids of WNV, in the 3000 region include target-complementary sequences of bases contained within the sequence of SEQ ID NO:99. Preferred hybridization assay probes useful for detecting flaviviral nucleic acids, such as the nucleic acids of WNV, in the 3' non-coding region include target-complementary sequences of bases contained within the sequence of SEQ ID NO:101, or within the subdomains defined by SEQ ID NO:102 or SEQ ID NO:103. Optional sequences which are not complementary to the nucleic acid sequence that is to be detected may be linked to the target-complementary sequence of the probe.

Referring particularly to the allowability of base differences which can distinguish useful probe sequences from a defined target region which contains the target-complementary complementary sequence of bases of that probe, it should be noted that base position 12 of the probe having the sequence of SEQ ID NO:114 (occupied by a T) differs from the corresponding position in the domain sequences defined by SEQ ID NO:101, SEQ ID NO:102 and SEQ ID NO:103 (all of which have a C at the corresponding position).

Certain preferred probes in accordance with the present invention include a detectable label.

In one embodiment this label is an acridinium ester joined to the probe by means of a non-nucleotide linker. For example, detection probes can be labeled with chemiluminescent acridinium ester compounds that are attached via a linker substantially as described in U.S. Pat. Nos. 5,585,481; and in 5,639,604, particularly as described at column 10, line 6 to column 11, line 3, and in Example 8. The disclosures contained in these patent documents are hereby incorporated by reference.

Table 7 presents the base sequences of some of the hybridization probes that were used for detecting WNV amplicons from each of the three WNV target regions. Since alternative probes for detecting WNV nucleic acid sequences can hybridize to the opposite-sense strand of WNV, the present invention also includes oligonucleotides that are complementary to the sequences presented in the table.

TABLE 7

Polynucleotide Sequences of WNV Detection Probes

| Target | Sequence | SEQ ID NO: |
|---|---|---|
| 5' Non-Coding Region | TGTCTAAGAAACCAGGAGGGC | SEQ ID NO: 96 |
| | GAAACCAGGAGGGCCCGG | SEQ ID NO: 97 |
| | GCTGTCAATATGCTAAAACG | SEQ ID NO: 98 |
| 3000 Region | GGTCCTTCGCAAGAGGTGG | SEQ ID NO: 100 |
| 3' Non-Coding Region | GAGTAGACGGTGCTGCCTGCG | SEQ ID NO: 104 |
| | GTAGACGGTGCTGCCTGCG | SEQ ID NO: 105 |
| | TGCGACTCAACCCCAGGAGGAC | SEQ ID NO: 106 |
| | TGCGACTCAACCCCAGGA | SEQ ID NO: 107 |
| | CGACTCAACCCCAGGAGGAC | SEQ ID NO: 108 |
| | GACTCAACCCCAGGAGGAC | SEQ ID NO: 109 |
| | GACTCAACCCCAGGAGGA | SEQ ID NO: 110 |
| | ACTCAACCCCAGGAGGAC | SEQ ID NO: 111 |
| | CAGGAGGACUGGGUGAACA | SEQ ID NO: 112 |
| | GAGGACUGGGUGAACAAAG | SEQ ID NO: 113 |
| | GTGAACAAAGCTGCGAAGTG | SEQ ID NO: 114 |
| | AAGCCGCGAAGTGATCCATG | SEQ ID NO: 115 |
| | GTAAGCCCTCAGAACCGTC | SEQ ID NO: 116 |

As indicated above, any number of different backbone structures can be used as a scaffold for the nucleobase sequences of the invented hybridization probes. In certain highly preferred embodiments, the probe sequence used for detecting WNV amplicons includes a methoxy backbone, or at least one methoxy linkage in the nucleic acid backbone.

Selection and Use of Capture Oligonucleotides

Preferred capture oligonucleotides include a first sequence that is complementary to a WNV sequence (i.e., a "WNV target sequence") covalently attached to a second sequence (i.e., a "tail" sequence) that serves as a target for immobilization on a solid support. Any backbone to link the base sequence of a capture oligonucleotide may be used. In certain preferred embodiments the capture oligonucleotide includes at least one methoxy linkage in the backbone. The tail sequence, which is preferably at the 3' end of a capture oligonucleotide, is used to hybridize to a complementary base sequence to provide a means for capturing the hybridized target WNV nucleic acid in preference to other components in the biological sample.

Although any base sequence that hybridizes to a complementary base sequence may be used in the tail sequence, it is preferred that the hybridizing sequence span a length of about 5-50 nucleotide residues. Particularly preferred tail sequences are substantially homopolymeric, containing about 10 to about 40 nucleotide residues, or more preferably about 14 to about 30 residues. A capture oligonucleotide according to the present invention may include a first sequence that specifically binds a WNV target polynucleotide, and a second sequence that specifically binds an oligo (dT) stretch immobilized to a solid support.

Using the components illustrated in FIG. 1, one assay for detecting WNV sequences in a biological sample includes the steps of capturing the target nucleic acid using the capture oligonucleotide, amplifying the captured target region using at least two primers, and detecting the amplified nucleic acid by first hybridizing the labeled probe to a sequence contained in the amplified nucleic acid and then detecting a signal resulting from the bound labeled probe.

The capturing step preferably uses a capture oligonucleotide where, under hybridizing conditions, one portion of the capture oligonucleotide specifically hybridizes to a sequence in the target nucleic acid and a tail portion serves as one component of a binding pair, such as a ligand (e.g., a biotin-avidin binding pair) that allows the target region to be separated from other components of the sample. Preferably, the tail portion of the capture oligonucleotide is a sequence that hybridizes to a complementary sequence immobilized to a solid support particle. Preferably, first, the capture oligonucleotide and the target nucleic acid are in solution to take advantage of solution phase hybridization kinetics. Hybridization produces a capture oligonucleotide:target nucleic acid complex which can bind an immobilized probe through hybridization of the tail portion of the capture oligonucleotide with a complementary immobilized sequence. Thus, a complex comprising a target nucleic acid, capture oligonucleotide and immobilized probe is formed under hybridization conditions. Preferably, the immobilized probe is a repetitious sequence, and more preferably a homopolymeric sequence (e.g., poly-A, poly-T, poly-C or poly-G), which is complementary to the tail sequence and attached to a solid support. For example, if the tail portion of the capture oligonucleotide contains a poly-A sequence, then the immobilized probe would contain a poly-T sequence, although any combination of complementary sequences may be used. The capture oligonucleotide may also contain "spacer" residues, which are one or more bases located between the base sequence that hybridizes to the target and the base sequence of the tail that hybridizes to the immobilized probe. Any solid support may be used for binding the target nucleic acid:capture oligonucleotide complex. Useful supports may be either matrices or particles free in solution (e.g., nitrocellulose, nylon, glass, polyacrylate, mixed polymers, polystyrene, silane polypropylene and, preferably, magnetically attractable particles). Methods of attaching an immobilized probe to the solid support are well known. The support is preferably a particle which can be retrieved from solution using standard methods (e.g., centrifugation, magnetic attraction of magnetic particles, and the like). Preferred supports are paramagnetic monodisperse particles (i.e., uniform in size ± about 5%).

Retrieving the target nucleic acid:capture oligonucleotide: immobilized probe complex effectively concentrates the target nucleic acid (relative to its concentration in the biological sample) and purifies the target nucleic acid from amplification inhibitors which may be present in the biological sample. The captured target nucleic acid may be washed one or more times, further purifying the target, for example, by resuspending the particles with the attached target nucleic acid:capture oligonucleotide:immobilized probe complex in a washing solution and then retrieving the particles with the attached complex from the washing solution as described above. In a preferred embodiment, the capturing step takes place by sequentially hybridizing the capture oligonucleotide with the target nucleic acid and then adjusting the hybridization conditions to allow hybridization of the tail portion of the capture oligonucleotide with an immobilized complementary sequence (e.g., as described in PCT No. WO 98/50583). After the capturing step and any optional washing steps have been completed, the target nucleic acid can then be amplified. To limit the number of handling steps, the target nucleic acid optionally can be amplified without releasing it from the capture oligonucleotide.

Useful capture oligonucleotides may contain mismatches to the above-indicated sequences, as long as the mismatched sequences hybridize to the WNV nucleic acid containing the sequence that is to be amplified. Each capture oligonucleotide described herein included one of the WNV-complementary sequences presented in Table 8 linked to a poly-(dA) tail at its 3' end. All of the capture oligonucleotides also included three optional thymidine nucleotides interposed between the WNV-complementary sequence and the poly-(dA) tail. The presence of these thymidine nucleotides is not believed to be essential for success of the capture procedure. The three thymidine nucleotides and the poly-(dA) tail were synthesized using DNA precursors, while the WNV-complementary portions of the oligonucleotides were synthesized using 2'-OMe nucleotide analogs.

TABLE 8

WNV-Complementary Portions of Capture Oligonucleotides

| Sequence | SEQ ID NO: |
| --- | --- |
| AAUCCUCACAAACACUACUAAGU | SEQ ID NO: 117 |
| AAGAACGCCAAGAGAGCCAACAC | SEQ ID NO: 118 |
| CCUCUUUUCUUUUGUUUUGAGCUCCG | SEQ ID NO: 119 |
| AATCCTCACAAACACTACTAAGT | SEQ ID NO: 120 |
| CCTCCTCTTTTCTTTTGTTTTG | SEQ ID NO: 121 |
| CCUCUCUUUUCUUUUGUUUUGAGC | SEQ ID NO: 122 |
| CCTCCTCTTTTCTTTTGTTTTGAGC | SEQ ID NO: 123 |
| UUCAUCGCUGUUUGUUUUGUUCAC | SEQ ID NO: 124 |
| TGTGTCTGCACTGTCAGTGACCT | SEQ ID NO: 125 |
| UGUGUCUGCACUGUCAGUGACCU | SEQ ID NO: 126 |
| GUUUUGUCUUCCAUCCAUUCA | SEQ ID NO: 127 |
| GUUUUGUCUUCCAUCCAUUCAU | SEQ ID NO: 128 |
| UCUCUCUCUUUCCCAUCAUGUUGUA | SEQ ID NO: 129 |
| CCUCCUCUUUUCUUUUGUUUUG | SEQ ID NO: 130 |

TABLE 8-continued

WNV-Complementary Portions of Capture Oligonucleotides

| Sequence | SEQ ID NO: |
| --- | --- |
| CCAACUGAUCCAAAGUCCCAAGC | SEQ ID NO: 131 |
| ACCCCUCCAACUGAUCCAAAGUCC | SEQ ID NO: 132 |
| GAACACCCCUCCAACUGAUCCAAA | SEQ ID NO: 133 |
| GCAGGUCCACGGUGUCCGCA | SEQ ID NO: 134 |
| UUCAUCGCUGUUUGUUUUGUUCAC | SEQ ID NO: 135 |
| CCTCCTCTTTTCTTTTGTTTTG | SEQ ID NO: 136 |
| GCAGGTCCACGGTGTCCGCA | SEQ ID NO: 137 |
| CUUCCAUCCAUUCAUUCUCCUC | SEQ ID NO: 138 |
| GUUUUGUCUUCCAUCCAUUCAUUC | SEQ ID NO: 139 |
| GTTTTGTCTTCCATCCATTCAT | SEQ ID NO: 140 |
| CTGGGGTTTTGTCTTCCATCCAT | SEQ ID NO: 141 |
| CUGGGGUUUUGUCUUCCAUCCAU | SEQ ID NO: 142 |

Preferred Methods for Amplifying and Detecting WNV Polynucleotide Sequences

Preferred methods of the present invention are described and illustrated by the Examples presented below. FIG. 1 schematically illustrates one system that may be used for detecting a target region of the WNV genome (shown by a thick solid horizontal line). This system includes four oligonucleotides (shown by the shorter solid lines): one capture oligonucleotide that includes a sequence that hybridizes specifically to a WNV sequence in the target region and a tail ("T") that hybridizes to a complementary sequence immobilized on a solid support to capture the target region present in a biological sample; one T7 promoter-primer which includes a sequence that hybridizes specifically to a WNV sequence in the target region and a T7 promoter sequence ("P") which, when double-stranded, serves as a functional promoter for T7 RNA polymerase; one non-T7 primer which includes a sequence that hybridizes specifically to a first strand cDNA made from the target region sequence using the T7 promoter-primer; and one labeled probe which includes a sequence that hybridizes specifically to a portion of the target region that is amplified using the two primers.

As indicated above, amplifying the captured target region using the two primers can be accomplished by any of a variety of known nucleic acid amplification reactions that will be familiar to those having an ordinary level of skill in the art. In a preferred embodiment, a transcription-associated amplification reaction, such as TMA, is employed. In such an embodiment, many strands of nucleic acid are produced from a single copy of target nucleic acid, thus permitting detection of the target by detecting probes that are bound to the amplified sequences. Preferably, transcription-associated amplification uses two types of primers (one being referred to as a promoter-primer because it contains a promoter sequence, labeled "P" in FIG. 1, for an RNA polymerase) two enzymes (a reverse transcriptase and an RNA polymerase), and substrates (deoxyribonucleoside triphosphates, ribonucleoside triphosphates) with appropriate salts and buffers in solution to produce multiple RNA transcripts from a nucleic acid template.

Referring to FIG. 1, during transcription-mediated amplification, the captured target nucleic acid is hybridized to a first primer shown as a T7 promoter-primer. Using reverse transcriptase, a complementary DNA strand is synthesized from the T7 promoter-primer using the target DNA as a template. A second primer, shown as a non-T7 primer, hybridizes to the newly synthesized DNA strand and is extended by the action of a reverse transcriptase to form a DNA duplex, thereby forming a double-stranded T7 promoter region. T7 RNA polymerase then generates multiple RNA transcripts by using this functional T7 promoter. The autocatalytic mechanism of TMA employs repetitive hybridization and polymerization steps following a cDNA synthesis step using the RNA transcripts as templates to produce additional transcripts, thereby amplifying target region-specific nucleic acid sequences.

The detecting step uses at least one detection probe that binds specifically to the amplified RNA transcripts or amplicons described above. Preferably, the detection probe is labeled with a label that can be detected using a homogeneous detection system. For example, the labeled probe can be labeled with an acridinium ester compound from which a chemiluminescent signal may be produced and detected, as described above. Alternatively, the labeled probe may comprise a fluorophore or fluorophore and quencher moieties. A molecular beacon is one embodiment of such a labeled probe that may be used in a homogeneous detection system.

Kits for Detecting WNV Nucleic Acids

The present invention also embraces kits for performing polynucleotide amplification reactions using viral nucleic acid templates. Certain preferred kits will contain a hybridization assay probe that includes a target-complementary sequence of bases, and optionally including primers or other ancilary oligonucleotides for amplifying the target that is to be detected. Other preferred kits will contain a pair of oligonucleotide primers that may be used for amplifying target nucleic acids in an in vitro amplification reaction. Exemplary kits include first and second amplification oligonucleotides that are complementary to opposite strands of a WNV nucleic acid sequence that is to be amplified. The kits may further contain one or more oligonucleotide detection probes. Still other kits in accordance with the invention may additionally include capture oligonucleotides for purifying WNV template nucleic acids away from other species prior to amplification.

The general principles of the present invention may be more fully appreciated by reference to the following non-limiting Examples.

Example 1 describes procedures that identified some of the hybridization probes which subsequently were used in assays for detecting WNV nucleic acids. More particularly, the following procedures identified probes that were capable of hybridizing to nucleic acids corresponding to one of three different WNV domains. These domains were: (1) the 5' non-coding region/capsid region (5' NCC), (2) the 3000 region (NS1/NS2a region), and (3) the 3' non-coding region (3' NC). Six synthetic oligonucleotides served as targets for binding the probes.

EXAMPLE 1

Oligonucleotide Probes for Detecting WNV

Synthetic WNV target oligonucleotides having the sequences presented in Table 9 were prepared according to standard laboratory procedures using 2'-OMe nucleotide analogs to mimic an RNA structure. Probes for hybridizing these synthetic WNV targets had the sequences given in Table 7, and were also prepared using 2'-OMe nucleotide analogs.

TABLE 9

| Target | Target Sequence | SEQ ID NO: |
|---|---|---|
| 5' Non-Coding Region | GCCCUCCUGGUUUCUUAGACAUC | SEQ ID NO: 143 |
| | UUGCCGGGCCCUCCUGGUUUCUUAGAC | SEQ ID NO: 144 |
| | AUC | SEQ ID NO: 145 |
| | CGCGUUUUAGCAUAUUGACAGCCC | |
| 3000 Region | UCCACCUCUUGCGAAGGACCUCC | SEQ ID NO: 146 |
| 3' Non-Coding Region | GUCGCAGGCAGCACCGUCUACUCAAC | SEQ ID NO: 147 |
| | CAGUCCUCCUGGGGUUGAGUCGCA | SEQ ID NO: 148 |
| | GAGACGGUUCUGAGGGCUUACAU | SEQ ID NO: 149 |
| | CAGUCCCCUGGGGUUGAGUCGCA | SEQ ID NO: 150 |
| | CAGUCCUCCUGGGGUUGAGCCGCA | SEQ ID NO: 151 |
| | CAGUCAUCCUGGGGUUGAGUCGCA | SEQ ID NO: 152 |

Hybridization reactions included about 1×10⁶ RLUs of AE-labeled probe having a specific activity of about 2×10⁸ RLU/pmole, and about 0.5 pmoles of synthetic WNV target oligonucleotide. Negative control reactions omitted the WNV target oligonucleotide. The probes listed in Table 7 were each labeled with an AE moiety joined to the oligonucleotide structure by an internally disposed non-nucleotide linker according to procedures described in U.S. Pat. Nos. 5,585,481 and 5,639,604, the disclosures of these patents having been incorporated by reference hereinabove. The linker on the probe of SEQ ID NO:96 was alternatively located between positions 5 and 6, between positions 9 and 10, between positions 13 and 14, or between positions 16 and 17. The linker on the probe of SEQ ID NO:97 was located between positions 9 and 10. The linker on the probe of SEQ ID NO:98 was alternatively located between positions 6 and 7, between positions 9 and 10, or between positions 11 and 12. The linker on the probe of SEQ ID NO:100 was alternatively located between positions 6 and 7, between positions 9 and 10, between positions 11 and 12, or between positions 13 and 14. The linker on the probe of SEQ ID NO:105 was alternatively located between positions 12 and 13, or between positions 13 and 14. The linker on the probe of SEQ ID NO:106 was located between positions 14 and 15. The linker on the probe of SEQ ID NO:107 was alternatively located between positions 6 and 7, or between positions 7 and 8. The linker on the probe of SEQ ID NO:108 was alternatively located between positions 6 and 7, or between positions 12 and 13. The linker on the probe of SEQ ID NO:109 was alternatively located between positions 5 and 6, or between positions 11 and 12. The linker on the probe of SEQ ID NO:110 was located between positions 11 and 12. The linker on the probe of SEQ ID NO:111 was alternatively located between positions 9 and 10, between positions 10 and 11, between positions 12 and 13, or between positions 13 and 14. The linker on the probe of SEQ ID NO:112 was alternatively located between positions 7 and 8, between positions 8 and 9, between positions 10 and 11, or between positions 11 and 12. The linker on the probe of SEQ ID NO:113 was alternatively located between positions 7 and 8, between positions 8 and 9, or between positions 9 and 10. The linker on the probe of SEQ ID NO:114 was located between positions 6 and 7. The linker on the probe of SEQ ID NO:115 was alternatively located between positions 12 and 13, between positions 13 and 14, or between positions 15 and 16. The linker on the probe of SEQ ID NO:116 was alternatively located between positions 5 and 6, between positions 10 and 11, or between positions 12 and 13. Use of all of these different linker positions confirmed the versatility of this labeling technique. Probe hybridizations were carried out at 62° C. for 15 minutes in 50 µl volumes of a succinate-buffered solution that included about 300 mM LiCl and about 0.75% (w/v) lithium lauryl sulfate. Hybridization reactions were followed by addition of 63 µl of 0.15 M sodium tetraborate (pH 8.5), and 1% TRITON X-100 (Union Carbide Corporation; Danbury, Conn.). These mixtures were first incubated at 62° C. for 10 minutes to inactivate the chemiluminescent label joined to unhybridized probe, and cooled briefly to 4° C. prior to reading the hybridization signal. Chemiluminescence due to hybridized probe in each sample was assayed using a LUMISTAR GALAXY luminescence microplate reader (BMG Labtechnologies Inc.; Durham, N.C.) configured for automatic injection of 1 mM nitric acid and 0.1% (v/v) hydrogen peroxide, followed by injection of a solution containing 1 N sodium hydroxide. Results for the chemiluminescent reactions were measured in relative light units (RLU). Representative results from this procedure are summarized in Table 10 for each of the three different target regions. Numerical values shown in the table indicate the average signal/noise ratio (S/N Avg.) calculated from either one or two trials, where each trial included four replicates.

TABLE 10

Probe Hybridization Results

| Target Region | Probe Identifier | Synthetic Target Identifier | S/N Avg.† |
|---|---|---|---|
| 5' Non-Coding Region | SEQ ID NO: 96 | SEQ ID NO: 143 | 814 |
| | | SEQ ID NO: 144 | 590 (n = 1) |
| | SEQ ID NO: 97 | SEQ ID NO: 144 | 45 |
| | SEQ ID NO: 98 | SEQ ID NO: 145 | 504 |
| 3000 Region | SEQ ID NO: 100 | SEQ ID NO: 146 | 1312 |
| 3' Non-Coding Region | SEQ ID NO: 104 | SEQ ID NO: 147 | 426 |
| | SEQ ID NO: 105 | SEQ ID NO: 147 | 720 |
| | SEQ ID NO: 106 | SEQ ID NO: 148 | 108 |
| | SEQ ID NO: 108 | | 99 |
| | SEQ ID NO: 109 | | 79 |
| | SEQ ID NO: 110 | | 88 |
| | SEQ ID NO: 111 | | 103 |
| | SEQ ID NO: 116 | SEQ ID NO: 149 | 609 |

†Unless indicated, all values represent the average of two trials (n = 2) of four replicates each.

The results presented in Table 10 showed that each probe tested in the procedure gave a strong hybridization signal following interaction with the WNV target sequence. Numerical values presented in the table are for the probes of SEQ ID NO:96 and SEQ ID NO:109 having their labels joined between nucleobase positions 5 and 6, for the probes of SEQ ID NO:104 and SEQ ID NO:108 having their labels joined between nucleobase positions 6 and 7, for the probes of SEQ ID NO:97, and SEQ ID NO:100 having their labels joined between nucleobase positions 9 and 10, for the probes of SEQ ID NO:111 and SEQ ID NO:116 having their labels joined between nucleobase positions 10 and 11, for the probes of SEQ ID NO:98 and SEQ ID NO:110 having their labels between nucleobase positions 11 and 12, for the probe of SEQ ID NO:105 having its label joined between nucleobase positions 12 and 13, and for the probe of SEQ ID NO:106 having its label joined between positions 14 and 15. However, all of the probes used in the procedure gave S/N values substantially greater than 10 when hybridized with at least one of the synthetic targets. Indeed, the positioning of any detectable label joined to any of the probes described herein can be varied and still fall within the scope of the invention. Each of the probes having one of the alternatively positioned labels particularly described above represents a preferred embodiment of the invented probe.

Although numerical results are not presented in Table 10, additional probes also were tested and shown to hybridize synthetic WNV target nucleic acids with very good results. More specifically, hybridization of the probes having the sequence of SEQ ID NO:112 with a synthetic WNV target having the sequence of CUUUGUUCACCCAGUCCUC-CUG (SEQ ID NO:194) gave signal/noise ratios as high as about 1100. Hybridization of the probes having the sequence of SEQ ID NO:113 with the same synthetic target sequence gave signal/noise ratios as high as about 1050. Hybridization of the probes having the sequence of 115 with a synthetic target having the sequence of ACAUGGAUCACUUCGCG-GCUUUG (SEQ ID NO:196) gave signal/noise ratios as high as about 1480. A probe having the sequence of SEQ ID NO:107, having its linker located between positions 7 and 8, was hybridized to a synthetic WNV target having the sequence of CCAGUCCUCCUGGGGUUGAGUCG-CAGGGCA (SEQ ID NO:193) and gave a signal/noise ratio of about 1000. Accordingly, each of the foregoing probe sequences represents a preferred embodiment of the invention, and falls within at least one of the extended probe domains defined herein.

Still other hybridization probes were tested by the same procedure and found to give good results. Again, all probes and targets were synthesized using 2'-OMe nucleotide analogs. Probes were labeled with chemiluminescent acridinium ester labels joined to the probes by non-nucleotide linkers, as described above. More particularly, a probe having the sequence of CCCTGCGACTCAACCCC (SEQ ID NO:189), having its linker located between positions 11 and 12, was hybridized to a synthetic WNV target having the sequence of SEQ ID NO:193 and gave a signal/noise ratio of about 180. A probe having the sequence of CCTGCGACTCAACCCC (SEQ ID NO:190), having its linker located between positions 13 and 14, was hybridized to a synthetic WNV target having the sequence of SEQ ID NO:193 and gave a signal/noise ratio of about 160. A probe having the sequence of CCTGCGACTCAACCC (SEQ ID NO:191), having its linker located between positions 11 and 12, was hybridized to a synthetic WNV target having the sequence of SEQ ID NO:193 and gave a signal/noise ratio of about 190. Probes having the sequence of AGGAGGACTGGGTGAACAA (SEQ ID NO:192), with labels alternatively located between positions 7 and 8 or positions 8 and 9, were hybridized to a synthetic WNV target having the sequence of GAUCACU-UCGCAGCUUUGUUCACCCAGUCCUCCUGG (SEQ ID NO:195) and gave signal/noise ratios of about 200. Again, each of the foregoing probe sequences represents a preferred embodiment of the invention, and falls within at least one of the extended probe domains defined herein.

The allowability of mismatches between a WNV target sequence and a substantially complementary hybridization probe was illustrated using one of the above-described probes and a collection of synthetic targets representing naturally occurring variant sequences. More specifically, samples containing the above-described AE-labeled probe of SEQ ID NO:111 were hybridized with synthetic target oligonucleotides containing substantially complementary portions of the viral sequences identified by GenBank accession numbers AF297856 (SEQ ID NO:150), AF260969 (SEQ ID NO:151) and AF297847 (SEQ ID NO:152). Each target was mismatched to the labeled hybridization probe at a different position, meaning that the probe and target were not complementary at the position of the mismatch. The standard target of SEQ ID NO:148 was fully complementary to the probe, and so was used as a positive control. The ability of the probe to hybridize each of the targets was assessed by the above-described procedure as a function of the input level of target.

Figure 2:
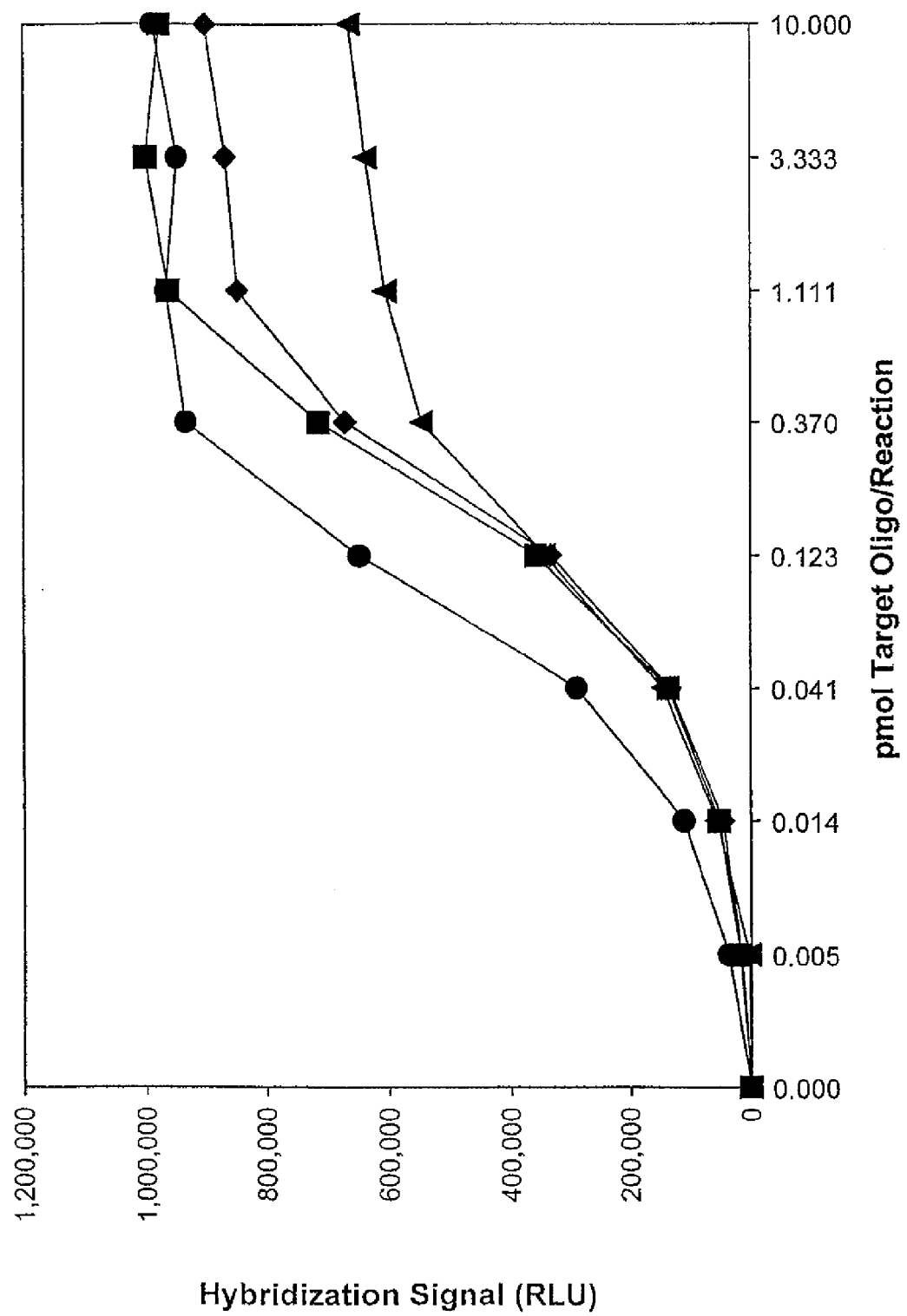
FIG. 2 shows a series of line graphs representing specific probe hybridization signals, measured in relative light units (y-axis) versus increasing levels of input target (x-axis). The target oligonucleotides used in the procedure had the sequences of SEQ ID NO:148 (●), SEQ ID NO:150 (♦), SEQ ID NO:151 (■), and SEQ ID NO:152 (▲).

As illustrated in FIG. 2, the hybridization probe clearly detected the targets which were not fully complementary to the probe sequence. This stringent test proved that mismatches between the hybridization probe and its target could be tolerated without compromising the ability of the probe to detect the target. Indeed, probes of the invention allowably may contain up to 10%, and even up to 20% base mismatches to the target without substantially compromising the ability of the probe to detect the target. Stated differently, the target-complementary sequence of bases included in the invented hybridization probes allowably can differ from the extended domain sequence from which it was derived at up to 10%, or even up to 20% of the base positions. Thus, hybridization probes and primers that are useful for detecting WNV will have target-complementary sequences of bases having a specified length range, and allowably may contain RNA and DNA equivalents, nucleotide analogs, and up to about 10%, or even up to 20% base differences when compared with a specified sequence which otherwise contains the probe or primer sequence. For example, a hybridization probe useful for detecting one of the above-described variant flavivirus sequences can have a target-complementary sequence of bases consisting of 18 contiguous bases contained within the sequence of SEQ ID NO:103 or SEQ ID NO:111 or the complements thereof, allowing for the presence of RNA and DNA equivalents, nucleotide analogs and up to 10% base differences, or even up to 20% base differences.

Hybridization assay probes having the sequences presented in Table 7 were subsequently used for demonstrating that a range of amplification primers and capture oligonucleotides could detect WNV nucleic acids in biological samples. Probes having these sequences or their complements, allowing for the presence of RNA and DNA equivalents and nucleotide analog substitutions, each represent particularly preferred embodiments of the invention.

Primers useful in accordance with the invention also exhibit flexibility with respect to the presence of base mismatches to an otherwise complementary target. This is because the amplification mechanism of nucleic acid amplification requires only transient primer binding to produce a first amplicon that will contain an exact match for complementary primer binding in a subsequent amplification cycle. Accordingly, and similar to the allowability of base differences or mismatches in hybridization probe sequences, primers that are useful for amplifying the nucleic acid sequences of flaviviruses, such as WNV, will have a 3' terminal target-complementary sequence of bases within a specified length range, allowing for the presence of RNA and DNA equivalents, nucleotide analogs and up to 10% base differences, or even up to 20% base differences when compared with a specified sequence that otherwise contains the primer sequence.

Preferred primer combinations for amplifying WNV nucleic acids were identified in a series of procedures that employed WNV virions as the source of nucleic acid templates. Promoter-primers and opposite strand primers were screened in combination using the method described below.

Although these procedures were particularly carried out using a Transcription Mediated Amplification (TMA) protocol, the primers disclosed herein may be used to produce amplicons by alternative in vitro nucleic acid amplification methods that will be familiar to those having an ordinary level of skill in the art.

Example 2 describes the methods that identified useful amplification primers for the West Nile virus 5' non-coding region.

EXAMPLE 2

Identification of Amplification Primers

A viral lysate served as the source of WNV template sequences in amplification reactions that employed paired sets of primers. TMA reactions were carried out essentially as described by Kacian et al., in U.S. Pat. No. 5,399,491, the disclosure of this U.S. patent having been incorporated by reference hereinabove.

Each promoter-primer included a T7 promoter sequence AATTTAATACGACTCACTATAGGGAGA (SEQ ID NO:153) upstream of a WNV-complementary sequence. Amplification reactions were conducted for various primer combinations using either 5 µl or 1.4 µl of a 1:10,000 dilution of a viral lysate of the NY99 WNV strain as a source of the WNV template (each reaction contained less than 1 PFU viral equivalents), and 10 pmoles of each primer in 100 µl of reaction buffer. The viral lysate was obtained from the Centers for Disease Control, National Center for Infectious Disease, Division of Vector-Borne Infectious Disease, Fort Collins, Colo. Nucleic acids underwent specimen processing and target capture prior to amplification essentially according to the procedures disclosed in published International Patent Application No. PCT/US2000/18685, except that the template was captured using WNV-specific oligonucleotides rather than HIV-specific oligonucleotides. Sets of capture oligonucleotides having the sequences of SEQ ID NO:117, SEQ ID NO:118 and SEQ ID NO:119 or the sequences of SEQ ID NO:120, SEQ ID NO:126 and SEQ ID NO:130 were used in combination, each at a level of 2-5 pmoles/reaction for trials conducted using 5 µl of viral lysate as the source of template nucleic acids. In a slight variation of this procedure, capture oligonucleotides having the sequences of SEQ ID NO:120, SEQ ID NO:118 and SEQ ID NO:119 were used in combination, each at a level of 2-5 pmoles/reaction for trials conducted using 1.4 µl of viral lysate as the source of template nucleic acids. Target nucleic acids and primers were heated to 60° C. for 10 minutes and then cooled to 42° C. to facilitate primer annealing. Moloney Murine Leukemia Virus (MMLV) reverse transcriptase (5,600 units/reaction) and T7 RNA polymerase (3,500 units/reaction) were then added to the mixtures. The final amplification reactions contained 50 mM Tris HCl (pH 8.2 to 8.5), 35 mM KCl, 4 mM GTP, 4 mM ATP, 4 mM UTP, 4 mM CIP, 1 mM dATP, 1 mM dTTP, 1 mM dCTP, 1 mM dG4TP, 20 mM $MgCl_2$, 20 mM N-Acetyl-L-Cysteine, and 5% (w/v) glycerol. After a one hour incubation at 42° C., the entire 100 µl amplification reaction was subjected to a hybridization assay essentially as described in Example 1 using the probe of SEQ ID NO:98 (see Table 10). More particularly, the probe was labeled with acridinium ester to a specific activity of about $2 \times 10^8$ RLU/pmol and then used in an amount equivalent to $2 \times 10^6$ RLU for each hybridization reaction. Trials were conducted using replicates of 10. To be judged as a positive result, either the chemiluminescent signal indicating probe hybridization must have exceeded 50,000 RLU in an assay, or the signal-to-noise ratio (where background noise was measured in a negative amplification control reaction) must have been at least 10.

Tables 11 and 12 present results from amplification procedures that were respectively conducted using amounts of WNV templates contained in 5 µl and 1.4 µl of viral lysate and different combinations of amplification primers. Results in the last columns of the tables show the number of positive trials and the number of replicate trials used in the procedures.

TABLE 11

Amplification of WNV Polynucleotide Sequences Using Various Primer Combinations

| WNV-Complementary Sequence of the Promoter-Primer | Opposite Strand Primer | # Positive/ # Tested |
|---|---|---|
| SEQ ID NO: 21 | SEQ ID NO: 4 | 2/10 † |
| | SEQ ID NO: 5 | 10/10 † |
| | SEQ ID NO: 6 | 0/10 † |
| | SEQ ID NO: 7 | 8/10 † |
| | SEQ ID NO: 8 | 0/10 † |
| | SEQ ID NO: 9 | 0/10 † |
| | SEQ ID NO: 13 | 4/10 † |
| | SEQ ID NO: 14 | 10/10 † |
| | SEQ ID NO: 10 | 3/10 ‡ |
| | SEQ ID NO: 11 | 1/10 ‡ |
| | SEQ ID NO: 12 | 0/10 ‡ |
| | SEQ ID NO: 15 | 0/10 ‡ |
| SEQ ID NO: 22 | SEQ ID NO: 4 | 0/10 ‡ |
| | SEQ ID NO: 5 | 0/10 ‡ |
| | SEQ ID NO: 6 | 1/10 ‡ |
| | SEQ ID NO: 7 | 0/10 ‡ |
| | SEQ ID NO: 8 | 0/10 ‡ |
| | SEQ ID NO: 9 | 0/10 ‡ |
| | SEQ ID NO: 13 | 0/10 † |
| | SEQ ID NO: 14 | 0/10 † |
| | SEQ ID NO: 10 | 0/10 ‡ |
| | SEQ ID NO: 11 | 0/10 ‡ |
| | SEQ ID NO: 12 | 1/10 ‡ |
| | SEQ ID NO: 15 | 0/10 ‡ |
| SEQ ID NO: 23 | SEQ ID NO: 4 | 1/10 † |
| | SEQ ID NO: 5 | 10/10 † |
| | SEQ ID NO: 6 | 0/10 † |
| | SEQ ID NO: 7 | 10/10 † |
| | SEQ ID NO: 8 | 0/10 † |
| | SEQ ID NO: 9 | 0/10 † |
| | SEQ ID NO: 13 | 10/10 † |
| | SEQ ID NO: 14 | 10/10 † |
| | SEQ ID NO: 10 | 10/10 ‡ |
| | SEQ ID NO: 11 | 10/10 ‡ |
| | SEQ ID NO: 12 | 10/10 ‡ |
| | SEQ ID NO: 15 | 9/10 ‡ |
| SEQ ID NO: 27 | SEQ ID NO: 4 | 2/10 † |
| | SEQ ID NO: 5 | 0/10 † |
| | SEQ ID NO: 6 | 0/10 † |
| | SEQ ID NO: 7 | 0/10 † |
| | SEQ ID NO: 8 | 0/10 † |
| | SEQ ID NO: 9 | 0/10 † |
| | SEQ ID NO: 13 | 10/10 † |
| | SEQ ID NO: 14 | 10/10 † |
| | SEQ ID NO: 10 | 10/10 ‡ |
| | SEQ ID NO: 11 | 10/10 ‡ |
| | SEQ ID NO: 12 | 10/10 ‡ |
| | SEQ ID NO: 15 | 10/10 ‡ |

† Capture oligonucleotides included the target-complementary sequences of SEQ ID NO: 117, SEQ ID NO: 118 and SEQ ID NO: 119.
‡ Capture oligonucleotides included the target-complementary sequences of SEQ ID NO: 120, SEQ ID NO: 126 and SEQ ID NO: 130.

The results presented in Table 11 showed that many of the primer combinations gave very high levels of WNV detectability, even at template levels lower than 1 PFU of viral equivalents per reaction. Even primer combinations that gave low, but measurable levels of WNV detectability in the results presented herein indicated successful amplification of WNV templates and established the combination as a useful component of a WNV nucleic acid amplification assay. Importantly, the results from these procedures showed that each of the primers complementary to one strand of the WNV nucleic acid could be paired with at least one of the primers complementary to the opposite strand of WNV nucleic acid to result in a highly sensitive amplification-based assay.

TABLE 12

Amplification of WNV Polynucleotide Sequences Using Various Primer Combinations

| WNV-Complementary Sequence of the Promoter-Primer | Opposite Strand Primer | # Positive/ # Tested |
|---|---|---|
| SEQ ID NO: 24 | SEQ ID NO: 10 | 9/10 |
| | SEQ ID NO: 11 | 10/10 |
| | SEQ ID NO: 12 | 9/10 |
| | SEQ ID NO: 15 | 9/10 |
| SEQ ID NO: 25 | SEQ ID NO: 10 | 10/10 |
| | SEQ ID NO: 11 | 10/10 |
| | SEQ ID NO: 12 | 10/10 |
| | SEQ ID NO: 15 | 10/10 |
| SEQ ID NO: 26 | SEQ ID NO: 10 | 10/10 |
| | SEQ ID NO: 11 | 10/10 |
| | SEQ ID NO: 12 | 10/10 |
| | SEQ ID NO: 15 | 9/10 |
| SEQ ID NO: 28 | SEQ ID NO: 10 | 10/10 |
| | SEQ ID NO: 11 | 10/10 |
| | SEQ ID NO: 12 | 10/10 |
| | SEQ ID NO: 15 | 10/10 |

The results presented in Table 12 further illustrate how the above-described capture oligonucleotides, probes and primers could be used in a highly sensitive assay for detecting WNV nucleic acids at very low levels of input template.

Example 3 describes the methods that identified primers useful for amplifying nucleic acids of the West Nile virus 3000 region.

EXAMPLE 3

Identification of Amplification Primers

Amplification reactions employing paired sets of primers specific for the 3000 region of WNV were carried out essentially as described under Example 2, except that promoter-primers having the WNV-complementary sequences presented in Table 4 were used in combination with opposite strand primers having the sequences presented in Table 3. Amplification reactions were conducted for the various primer combinations using 5 μl or 1.4 μl of a 1:10,000 dilution of the above-described viral lysate (each reaction contained less than 1 PFU viral equivalents). Nucleic acids underwent specimen processing in accordance with Example 2, using combinations of capture oligonucleotides that included the target-complementary sequences of SEQ ID NO:117, SEQ ID NO:118 and SEQ ID NO:119 or the target-complementary sequences of SEQ ID NO:120, SEQ ID NO:126, and SEQ ID NO:130. Each capture oligonucleotide was used at a level of 2-5 pmoles/reaction in the target capture step. Target nucleic acids and primers were heated to 60° C. for 10 minutes and then cooled to 42° C. and amplification reactions conducted as described above. At the conclusion of the amplification reactions, the entire reaction volumes were subjected to a hybridization assay using a probe having the sequence of SEQ ID NO:100 (see Table 10). More particularly, the probe was labeled with acridinium ester to a specific activity of about $2\times10^8$ RLU/pmol and then used in an amount equivalent to about $1\times10^6$ to $1\times10^7$ RLU for each hybridization reaction. Trials were conducted using replicates of 10. To be judged as a positive result, the chemiluminescent signal indicating probe hybridization must have exceeded 50,000 RLU in an assay.

Table 13 presents results from amplification procedures that were conducted using different combinations of primers to amplify nucleic acids of the 3000 region of WNV. Results in the last column of the table show the number of positive trials and the number of replicate trials used in the procedure. Unless indicated to the contrary, all reactions were carried out using 5 µl of WNV lysate as the source of viral nucleic acids.

TABLE 13

Amplification of WNV Polynucleotide Sequences Using Various Primer Combinations

| WNV-Complementary Sequence of the Promoter-Primer | Opposite Strand Primer | # Positive/ # Tested |
|---|---|---|
| SEQ ID NO: 53 | SEQ ID NO: 42 | 10/10 † |
| | SEQ ID NO: 43 | 8/10 † |
| | SEQ ID NO: 44 | 0/10 † |
| | SEQ ID NO: 45 | 6/10 † |
| | SEQ ID NO: 46 | 0/10 † |
| | SEQ ID NO: 47 | 10/10 † |
| | SEQ ID NO: 48 | 9/10 † |
| | SEQ ID NO: 49 | 10/10 § ‡ |
| | SEQ ID NO: 50 | 10/10 § ‡ |
| | SEQ ID NO: 51 | 10/10 § ‡ |
| SEQ ID NO: 54 | SEQ ID NO: 42 | 4/10 † |
| | SEQ ID NO: 43 | 1/10 † |
| | SEQ ID NO: 44 | 0/10 † |
| | SEQ ID NO: 45 | 0/10 † |
| | SEQ ID NO: 46 | 0/10 † |
| | SEQ ID NO: 47 | 10/10 † |
| | SEQ ID NO: 48 | 8/10 † |
| | SEQ ID NO: 49 | 8/10 ‡ |
| | SEQ ID NO: 50 | 5/10 ‡ |
| | SEQ ID NO: 51 | 2/10 ‡ |
| SEQ ID NO: 55 | SEQ ID NO: 42 | 0/10 † |
| | SEQ ID NO: 43 | 0/10 † |
| | SEQ ID NO: 44 | 0/10 † |
| | SEQ ID NO: 45 | 0/10 † |
| | SEQ ID NO: 46 | 0/10 † |
| | SEQ ID NO: 47 | 9/10 † |
| | SEQ ID NO: 48 | 0/10 † |
| | SEQ ID NO: 49 | 0/10 † |
| | SEQ ID NO: 50 | 9/10 † |
| | SEQ ID NO: 51 | 10/10 † |

§ WNV template was provided in 1.4 µl of lysate.
† Capture oligonucleotides included the target-complementary sequences of SEQ ID NO: 117, SEQ ID NO: 118 and SEQ ID NO: 119.
‡ Capture oligonucleotides included the target-complementary sequences of SEQ ID NO: 120, SEQ ID NO: 126 and SEQ ID NO: 130.

The results presented in Table 13 showed that many of the listed primer combinations were useful for creating highly sensitive assays that involved amplification of WNV nucleic acids. Indeed, it is contemplated that any of the listed primers complementary to one strand can be used in combination with any of the listed primers complementary to the opposite strand for amplifying WNV nucleic acids at some level of input template.

Example 4 describes the methods that identified primers useful for amplifying nucleic acids of the West Nile virus 3' non-coding region.

EXAMPLE 4

Identification of Amplification Primers

Amplification reactions employing paired sets of primers specific for the 3' non-coding region of WNV were carried out essentially as described under the preceding Example, except that promoter-primers having the WNV-complementary sequences presented in Table 6 were used in combination with opposite strand primers having the sequences presented in Table 5. Amplification reactions were conducted for the various primer combinations using either 1.4 µl or 0.14 µl of a 1:10,000 dilution of the above-described viral lysate (each reaction contained less than 1 PFU viral equivalents). Nucleic acids underwent specimen processing using capture oligonucleotides having the target-complementary sequences of SEQ ID NO:118, SEQ ID NO:119 and SEQ ID NO:120 in combination, each at a level of 2-5 pmoles/reaction. Target nucleic acids and primers were heated to 60° C. for 10 minutes and then cooled to 42° C. and amplification reactions conducted as described above. At the conclusion of the amplification reactions, the entire reaction volumes were subjected to a hybridization assay using a probe having the sequence of SEQ ID NO:104 (see Table 10). More particularly, the probe was labeled with acridinium ester to a specific activity of about $2\times10^8$ RLU/mol and then used in an amount equivalent to about $1\times10^6$ to $1\times10^7$ RLU for each hybridization reaction. Trials were conducted using replicates of 10. To be judged as a positive result, the chemiluminescent signal indicating probe hybridization must have exceeded 50,000 RLU in an assay.

Table 14 presents results from amplification procedures that were conducted using different combinations of primers. Results in the last columns of the table show the number of positive trials and the number of replicate trials used in the procedures.

TABLE 14

Amplification of WNV Polynucleotide Sequences Using Various Primer Combinations

| WNV-Complementary Sequence of the Promoter-Primer | Opposite Strand Primer | # Positive/ # Tested |
|---|---|---|
| SEQ ID NO: 75 | SEQ ID NO: 60 | 6/10 † |
| | SEQ ID NO: 62 | 4/10 † |
| | SEQ ID NO: 63 | 3/10 † |
| | SEQ ID NO: 64 | 5/10 † |
| | SEQ ID NO: 65 | 1/10 † |
| | SEQ ID NO: 66 | 2/10 † |
| SEQ ID NO: 76 | SEQ ID NO: 60 | 5/10 † |
| | SEQ ID NO: 62 | 4/10 † |
| | SEQ ID NO: 63 | 7/10 † |
| | SEQ ID NO: 64 | 10/10 ‡ |
| | SEQ ID NO: 65 | 2/10 ‡ |
| | SEQ ID NO: 66 | 10/10 ‡ |
| SEQ ID NO: 77 | SEQ ID NO: 60 | 4/10 † |
| | SEQ ID NO: 62 | 7/10 † |
| | SEQ ID NO: 63 | 4/10 † |
| | SEQ ID NO: 64 | 10/10 ‡ |
| | SEQ ID NO: 65 | 1/10 ‡ |
| | SEQ ID NO: 66 | 10/10 ‡ |

† tested with 0.14 µl of a 1:10,000 dilution of WNV lysate
‡ tested with 1.4 µl of a 1:10,000 dilution of WNV lysate The results presented in Table 14 showed that the listed primer combinations were useful for creating highly sensitive assays that involved amplification of WNV nucleic acids. Indeed, it is contemplated that any of the listed primers complementary to one strand can be used in combination with any of the listed primers complementary to the opposite strand for amplifying WNV nucleic acids at some level of input template.

Notably, in all but a single instance, other promoter-primers that were used in combination with the opposite strand primers listed in Table 14 gave 0 positive/10 tests at the indicated target input level. More particularly, T7 promoter-primers that included WNV-complementary sequences given by the following oligonucleotides did not give good results when tested using the conditions given above when tested in combination with each of the opposite strand primers listed in Table 14: SEQ ID NO:82, SEQ ID NO:83, SEQ ID NO:80 and SEQ ID NO:81. If all primers were equivalent, then measurable results would have been expected when using these primers, and that was not the case. Primers useful for conducting amplification procedures with extraordinary sensitivity were contained within the highly preferred domains of SEQ ID NO:73 and SEQ ID NO:74.

To further demonstrate flexibility in the assay design, additional procedures were conducted to show how more than one same-sense primer could be used in the amplification reaction without compromising assay sensitivity. Indeed, the ability to employ more than one same-sense primer in the assay represents one strategy for detecting WNV genetic variants.

Reactions for amplifying and detecting WNV in the 3' non-coding region were carried out substantially as described above, with the following minor modifications. Capture oligonucleotides used in the procedure included the target-complementary sequences of SEQ ID NO:134, SEQ ID NO:131 and SEQ ID NO:127+A promoter-primer that included the target-complementary sequence of SEQ ID NO:76 was present in all amplification reactions. Except as indicated in the table of results, all reactions included a primer having the sequence of SEQ ID NO:64 in combination with a second primer of the same sense that hybridized to the same strand of WNV nucleic acid. In one instance the primer having the sequence of SEQ ID NO:68 and the promoter-primer of SEQ ID NO:85, which included the target-complementary sequence of SEQ ID NO:76, were used for amplifying WNV nucleic acids in the absence of a third primer A probe having the sequence of SEQ ID NO:111 was used in all instances for detecting amplicon production. Reactions were carried out in replicates of 10, and were primed using 0.33 µl of the 1:10, 000 dilution of the above-described viral lysate (approximately 10-20 copies of the viral target per reaction). To be judged as a positive result, the chemiluminescent signal indicating probe hybridization must have exceeded 50,000 RLU in an assay. Notably, these trials additionally included an HIV-1 internal control template and primers that did not substantially affect amplification or detection of the WNV target.

The results presented in Table 15 showed that each of the tested primer combinations facilitated amplification and detection of WNV nucleic acids.

TABLE 15

Amplification of WNV Polynucleotide Sequences Using Combinations of Same-Sense Primers

| Promoter-Primer | Opposite Strand Primer No. 1 | Opposite Strand Primer No. 2 | Testing Results |
| --- | --- | --- | --- |
| SEQ ID NO: 85 | SEQ ID NO: 64 | None | 9/10 |
| | | SEQ ID NO: 67 | 10/10 |
| | | SEQ ID NO: 69 | 10/10 |
| | | SEQ ID NO: 68 | 10/10 |
| | | SEQ ID NO: 70 | 10/10 |
| | | SEQ ID NO: 71 | 10/10 |
| | None | SEQ ID NO: 68 | 10/10 |

To illustrate still further the flexibility in the assay design, another procedure was conducted using the same set of capture oligonucleotides, and using multiple primers for generating WNV amplicons, but using different hybridization probes in the detection step. More specifically, capture oligonucleotides used in the procedure included the target-complementary sequences of SEQ ID NO:134, SEQ ID NO:131 and SEQ ID NO:127. A promoter-primer having the WNV-complementary sequence of SEQ ID NO:76 was used in combination with opposite strand primers having the sequences of SEQ ID NO:64 and SEQ ID NO:68. Amplification reactions were conducted using 1.4 µl of the above-described viral lysate as a template source. Detection reactions were carried out as described above using either of two different probes, one having the sequence of SEQ ID NO:107, and the other having the sequence of SEQ ID NO:114, each of these probes having been described above. Results from these procedures gave 10/10 positives using the probe of SEQ ID NO:107, and 18/18 positives using the probe of SEQ ID NO:114. This confirmed the utility of the hybridization probes and further demonstrated how elements of the amplification and detection procedure could be combined to result in sensitive assays. Notably, the probe of SEQ ID NO:114 was found in other procedures to give exceptionally reproducible results, even when biological samples undergoing testing were prepared by slightly different procedures. As noted above, the probe sequence of SEQ ID NO:114 differs slightly from the corresponding sequence contained in the probe domains defined by SEQ ID NO:101, SEQ ID NO:102 and SEQ ID NO:103.

The following Example describes the methods used for testing candidate WNV capture oligonucleotides. In addition to the WNV-specific target capture, amplification primer, and probes described in this procedure, the reactions also tested the effect of including capture oligonucleotides specific for HIV-1, HCV and HBV analytes.

EXAMPLE 5

Detection of WNV Target Sequences Using Different Capture Oligonucleotides

Aliquots of the WNV lysate used in the above-described procedures were dispersed in 400 µl of lysis/capture reagent containing about 4 pmoles of each capture oligonucleotide and about 40 µg of 0.7-1.05µ paramagnetic particles (Seradyn, Indianapolis, Ind.) covalently linked to poly-($dT_{14}$). Capture oligonucleotides used in the procedure had the sequences given in Table 8. The lysis/capture reagent further included an HIV-1 internal amplification control template, HIV-1, HCV and HBV—specific capture oligonucleotides, and a 100 mM HEPES-buffered solution containing 294 mM lithium lauryl sulfate, 730 mM lithium chloride, and 50 mM lithium hydroxide. As stated above, a 5'-TTT-3' spacer sequence was interposed between the WNV-complementary sequence and the oligo-(dA) tail region for each of the capture oligonucleotides shown in Table 8. The mixtures were heated to 55-60° C. for about 15-30 minutes, and then cooled to room temperature to allow hybridization. A magnetic field was applied to collect the particle complexes containing the immobilized capture oligonucleotide and WNV DNA using procedures such as those described by Wang in U.S. Pat. No. 4,895,650. The particles were washed twice with 1 ml of a washing buffer (10 mM HEPES, 6.5 mM NaOH, 1 mM EDTA, 0.3% (v/v) ethanol, 0.02% (w/v) methyl-paraben, 0.01% (w/v) propyl-paraben, 150 mM NaCl, 0.1% (w/v) sodium lauryl sulfate). Washed particles were then resuspended in 75 µl of the amplification reagent described under Example 2. This reagent included salts, nucleotides, ribonucleotides, WNV-specific primers. Some trials additionally included primers capable of amplifying an HIV-1 internal control template. The WNV target nucleic acid was then amplified, and the amplification products detected using a homogenous protection assay, essentially as described under Example 1 using the hybridization probe of SEQ ID NO:98 (see Table 10). Reactions that gave positive signals when hybridized with a probe specific for the internal control amplicon, or with a probe specific for the WNV amplicon, were scored as valid reactions. In order for a valid run to be considered positive for the presence of WNV amplicons, the chemiluminescent signal indicating probe hybridization must have exceeded 50,000 RLU in an assay.

Table 16 presents sample results correlating the identity of the WNV-specific capture oligonucleotide(s) and the ability of the system to amplify and detect WNV sequences efficiently. To achieve a positive result in the amplification reactions, the WNV capture oligonucleotide must have been able to act cooperatively with the amplification primers and probe(s) to capture WNV template nucleic acids, amplify the WNV template nucleic acids, and then detect the amplified nucleic acids.

Notably, promoter-primers used in this procedure and listed in Table 16 are identified by the complete sequence that included the T7 promoter. It is to be understood however, that the WNV-complementary portions of the promoter-primers represent essential sequences for performing amplification reactions by alternative protocols, such as the polymerase chain reaction, with the promoter sequence being optional. Thus, it is to be understood that some of the primers listed in Table 16 possessed optional promoter sequences, and that the corresponding primers which do not include the optional promoter represent the essential WNV-complementary sequences. These latter WNV-complementary sequences are useful in conjunction with opposite strand primers for amplifying WNV nucleic acids.

TABLE 16

Efficiency of WNV Detection Using Different Combinations of Capture Oligonucleotides

| Capture Oligonucleotide(s) | Amplification Primers | # Positive/ # Tested |
|---|---|---|
| None | SEQ ID NO: 35 | 9/20 |
| SEQ ID NO: 118 | SEQ ID NO: 14 | 17/20 |
| SEQ ID NO: 119 | | 16/20 |
| SEQ ID NO: 117 | | 14/20 |
| SEQ ID NO: 118 | | |
| SEQ ID NO: 119 | | |
| SEQ ID NO: 117 | | 20/20 |
| SEQ ID NO: 120 | | 20/20 |
| SEQ ID NO: 130 | | 20/20 |
| SEQ ID NO: 121 | | 20/20 |
| SEQ ID NO: 122 | | 19/20 |
| SEQ ID NO: 123 | | 20/20 |

The results presented in Table 16 confirmed that substantially all of the capture oligonucleotides that were tested, either alone or in combination, were useful in the WNV detection assay.

Like the NY99 strain that was used in the foregoing Examples, the Ugandan strain of West Nile virus is one of more than 100 known strains of the West Nile virus. Based on sequencing and phylogenetic analysis, the known viruses have been divided into two lineages—Lineage 1 and Lineage 2. Epidemiological data indicates that Lineage 2 strains, which have been isolated from either asymptomatic or mild febrile human cases, are somewhat less virulent than Lineage 1 strains. Lineage 1 strains have been associated with epidemics in which there have been human encephalitis cases and fatalities.

A key advantage of the above-described amplification systems was demonstrated using a "proficiency panel" of the West Nile virus Ugandan strain (an example of a Lineage 2 strain). Those having an ordinary level of skill in the art will appreciate that this strain is only distantly related at the nucleic acid level to the NY99 strain (an example of a Lineage 1 strain) that predominates in the United States. Thus, whether an assay can detect both the NY99 and Ugandan strains of WNV represents a highly stringent test for usefulness in a clinical setting.

Example 6 describes the methods used for demonstrating that the Ugandan strain of West Nile virus was detected by the same assays that detected the NY99 strain.

EXAMPLE 6

Amplification and Detection of the West Nile Virus Ugandan Strain

A proficiency panel of samples containing known amounts of the Ugandan strain of WNV in 800 to 1,000 µl volumes of a human serum derivative was obtained from Boston Biomedica Inc. (MA). This panel consisted of a plurality of members, each containing either 0, 30, 100, 1,000 or 10,000 copies/ml of the WNV Ugandan strain RNA. Target-capture, amplification and detection procedures were performed essentially as described in the preceding Examples. In this Example the capture oligonucleotides having the target-complementary sequences of SEQ ID NO:120, SEQ ID NO:130 and SEQ ID NO:126 were used in combination with each other. In a preliminary procedure one of the panel members containing 10,000 copies/ml of the viral RNA was used to create a series of dilutions that contained either 10, 30, 100 or 300 copies of the viral nucleic acid. Amplification and detection reactions were performed using the oligonucleotide reagents listed in Table 17. In the present case the label on the probe having the sequence of SEQ ID NO:98 was located between positions 11 and 12; the label on the probe having the sequence of SEQ ID NO:100 was located between positions 9 and 10; and the label on the probe having the sequence of SEQ ID NO:104 was located between positions 6 and 7. When panel members were used for testing without prior dilution, a 500 µl aliquot was used for a reaction that amplified the 3000 region of the target and the remaining volume of the panel member (amounting to less than 500 µl) was used in a reaction that amplified the 3' non-coding region. Testing was restricted to these two regions because the volumes of undiluted panel members were limiting. Positive results were scored when the signal-to-noise ratio was at least 10.

TABLE 17

Oligonucleotides Used for Amplifying and Detecting the Ugandan Strain of WNV

| Target Region | Reagent | Oligonucleotide Identifier |
|---|---|---|
| 5' Non-Coding Region | Promoter-Primer | SEQ ID NO: 40 |
| | Opposite-Strand Primer | SEQ ID NO: 10 |
| | Probe | SEQ ID NO: 98 |
| 3000 Region | Promoter-Primer | SEQ ID NO: 56 |
| | Opposite-Strand Primer | SEQ ID NO: 47 |
| | Probe | SEQ ID NO: 100 |
| 3' Non-Coding Region | Promoter-Primer | SEQ ID NO: 85 |
| | Opposite-Strand Primer | SEQ ID NO: 64 |
| | Probe | SEQ ID NO: 104 |

Table 18 presents numerical results from this procedure. Precision among the results for each series of reactions conducted at a single target level was determined by calculating a coefficient of variability (% CV).

The results in Table 19 showed that the assays for amplifying and detecting sequences in the 3000 and 3' non-coding

TABLE 18

Sensitivity Testing for Three Amplification Systems using the Ugandan Strain of WNV

| | 5' Non-Coding Region | | | 3000 Region | | | 3' Non-Coding Region | | |
|---|---|---|---|---|---|---|---|---|---|
| C/ml | Avg. RLU | % CV | % Pos | Avg. RLU | % CV | % Pos | Avg. RLU | % CV | % Pos |
| 300 | 1,780,609 (N = 5) | 41 | 100 | 900,886 (N = 5) | 1 | 100 | 1,587,825 (N = 5) | 2 | 100 |
| 100 | 1,991,413 (N = 10) | 12 | 100 | 907,638 (N = 10) | 2 | 100 | 1,514,945 (N = 10) | 8 | 100 |
| 30 | 1,392,727 (N = 10) | 29 | 100 | 910,241 (N = 10) | 2 | 100 | 1,171,792 (N = 10) | 26 | 100 |
| 10 | 896,831 (N = 10) | 56 | 90 | 893,069 (N = 10) | 3 | 100 | 636,116 (N = 10) | 40 | 100 |
| 0 | 1,445 (N = 5) | 37 | 0 | 1,179 (N = 5) | 8 | 0 | 1,383 (N = 5) | 8 | 0 |

The results presented in Table 18 confirmed that each of the three different target regions in the Ugandan strain of WNV could be amplified and detected in highly sensitive manner using the same oligonucleotide reagents that had been used for amplifying and detecting the NY99 strain. Each of the different amplification systems detected viral nucleic acids in 100% of the samples down to 30 copies/ml. The systems for detecting targets in the 3000 region and 3' non-coding region detected viral nucleic acids in 100% of the samples down to 10 copies/ml. Because 0.5 ml samples of the various dilutions were used in the detection procedures, the number of viral RNA copies/reaction was one half of the number of viral RNA copies/ml. Positive results indicating the viral target was detected when source samples contained 10 copies/ml of the viral RNA meant that the assay detected 5 copies of the viral RNA. Notably, the reactions that amplified nucleic acids in the 3000 region and 3' non-coding region advantageously gave low % CV readings, thereby indicating high levels of precision in the amplification reactions.

TABLE 19

Proficiency Testing Verifies Sensitive Detection of WNV Ugandan Strain

| Panel Member | WNV RNA Stock (copies/ml) | Results 3000 Region | Results 3' Non-Coding Region |
|---|---|---|---|
| QWN701.01 | 100 | Positive | Positive |
| QWN701.02 | 0 | Negative | Negative |
| QWN701.03 | 10,000 | Not Tested | Not Tested |
| QWN701.04 | 30 | Positive | Positive |
| QWN701.05 | 1,000 | Positive | Positive |
| QWN701.06 | 300 | Positive | Positive |
| QWN701.07 | 100 | Positive | Positive |
| QWN701.08 | 0 | Negative | Negative |
| QWN701.09 | 30 | Positive | Positive |
| QWN701.10 | 1,000 | Positive | Positive |
| QWN701.11 | 100 | Positive | Positive |
| QWN701.12 | 10,000 | Not Tested | Not Tested |
| QWN701.13 | 0 | Negative | Negative |
| QWN701.14 | 30 | Positive | Positive |
| QWN701.15 | 300 | Positive | Positive |
| Negative Control | 0 | Negative | Negative |
| Negative Control | 0 | Negative | Negative |
| Negative Control | 0 | Negative | Negative |
| Negative Control | 0 | Negative | Negative |
| Negative Control | 0 | Negative | Negative | regions of West Nile virus detected the Ugandan strain of the viral RNA target down to 15 copies/reaction, or lower, without giving any false-positive results. These findings were consistent with the results presented in Table 18.

To illustrate further how the oligonucleotides described herein could be combined to produce highly sensitive assays, different combinations of capture oligonucleotides, primers and a probe were used for amplifying and detecting the West Nile virus Ugandan strain. Procedures similar to those described above were used, except that capture oligonucleotides that included the target-complementary sequences of SEQ ID NO:117, SEQ ID NO:134 and SEQ ID NO:128 were used, the promoter primer of SEQ ID NO:85 included the target-complementary sequence of SEQ ID NO:76, the opposite-strand primer had the sequence of SEQ ID NO:64, and the above-described oligonucleotide having the sequence of SEQ ID NO:111 was used as the probe. Additionally, samples containing 3, 1, 0.3 and 0.1 copies/ml of the virus were tested in replicates of 20 to generate data for accurately quantifying assay sensitivity. Regression analysis using the Probit function in SAS® System software (version 8.02) (Cary, N.C.) was used to calculate the 95% and 50% detection levels. Invalid reactions were not re-tested and were not included in the analysis of analytical sensitivity.

TABLE 20

Quantitative Sensitivity Testing using the Ugandan Strain of WNV

| | | | Analysis | |
|---|---|---|---|---|
| C/ml | % CV | % Positive | 95% Detection Level in copies/ml (95% Confidence) | 50% Detection Level in copies/ml (95% Confidence) |
| 300 | 5.9 | 100 | 9.0 (7.1 to 12.8) | 4.5 (3.5 to 6.1) |
| 100 | 33.9 | 100 | | |
| 30 | 60.7 | 100 | | |
| 10 | 98.4 | 95 | | |
| 3 | 118 | 45 | | |
| 1 | NA | 5 | | |
| 0.3 | 128 | 0 | | |
| 0.1 | 178 | 0 | | |
| 0 | 129 | 0 | | |

The results presented in Table 20 again showed that the Ugandan strain of West Nile virus was detected with excellent sensitivity in the amplified assay. More specifically, analysis of the results predicted 95% detection, using the nucleic acid amplification assay and end-point detection system, down to about 7-13 viral copies/ml, an amount corresponding to about 4-7 copies/reaction.

To further illustrate the versatility of the above-described analyte detection systems, amplicon production was monitored as a function of time in "real-time" amplification procedures. Amplicon-specific molecular beacons that were included in the amplification reactions provided a means for continuous monitoring of amplicon synthesis. Fluorescent emissions that increased with time indicated the production of amplicons that hybridized to the molecular beacon and caused a detectable transition to the "open" conformation of the probe.

Molecular beacons comprise nucleic acid molecules having a target-complementary sequence, an affinity pair (or nucleic acid "arms") that interact to form a "stem" structure by complementary base pairing in the absence of a target (i.e., the "closed" conformation), and a paired set of labels that interact when the probe is in the closed conformation. Those having an ordinary level of skill in the art will understand that the target-complementary sequence contained within the structure of a molecular beacon is generally in the form of a single-stranded "loop" region of the probe. Hybridization of the target nucleic acid and the target-complementary sequence of the probe causes the members of the affinity pair to separate, thereby shifting the probe to the open conformation. This shift is detectable by virtue of reduced interaction between the members of the label pair, which may be, for example, a fluorophore and a quencher. Molecular beacons are fully described in U.S. Pat. No. 5,925,517, the disclosure of this patent document being incorporated by reference herein.

Figure 3:
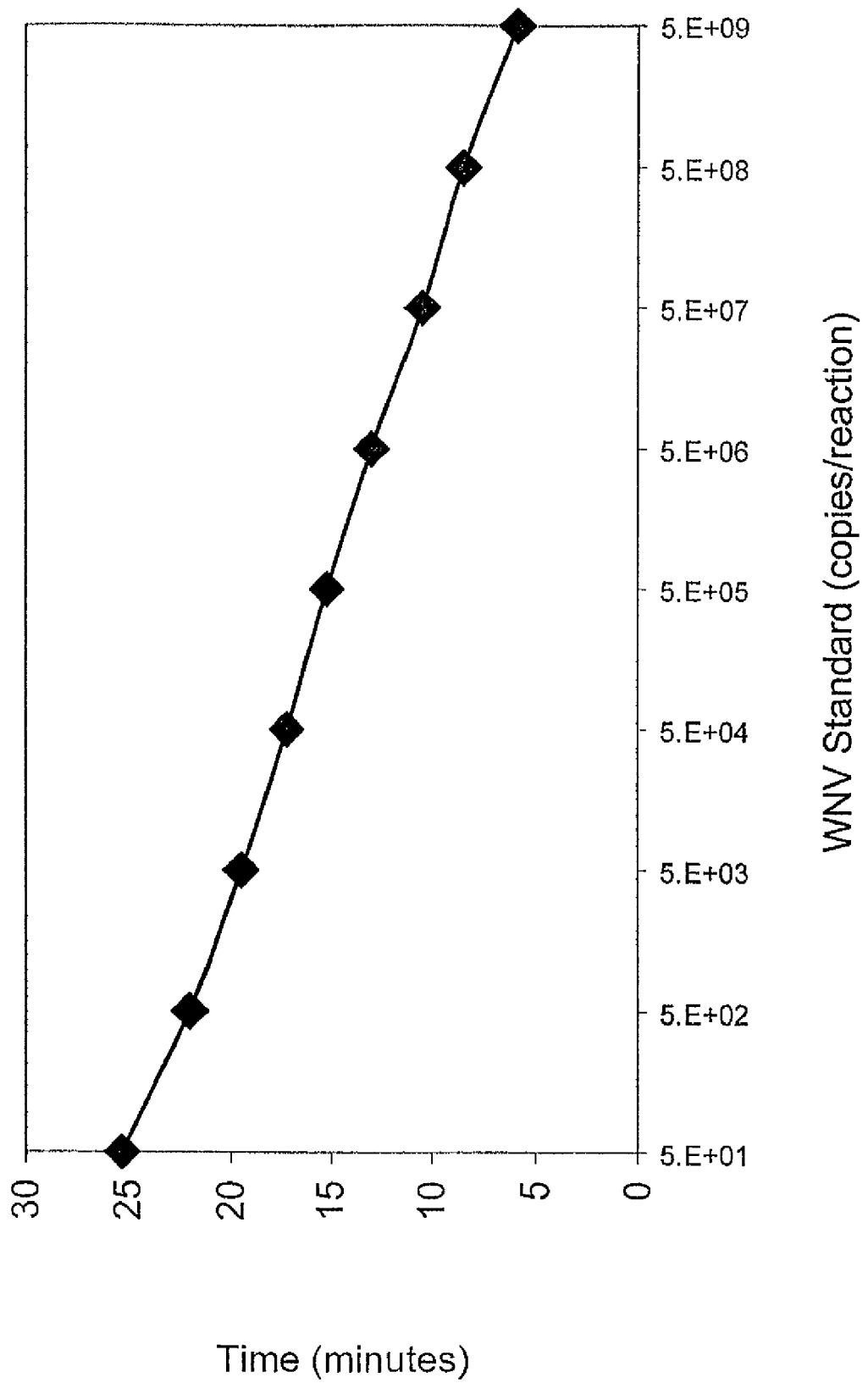
FIG. 3 is a line graph relating the amount of WNV standard input into a real-time nucleic acid amplification reaction (x-axis) and the time-of-emergence of the measured fluorescent signal above a background threshold (y-axis).

Commercially available software was used to analyze time-dependent results obtained using molecular beacons that were specific for amplicons derived from: (1) the 5' non-coding region, (2) the 3000 region, and (3) the 3' non-coding region. Results from these analyses indicated a substantially linear relationship between the number of target copies included in an amplification reaction and the time at which the fluorescent signal exceeded a background threshold (i.e., "time-of-emergence" above background), as illustrated in FIG. 3. As confirmed by the results presented below, these procedures were useful for quantifying analyte target amounts over a very broad range. More particularly, when known amounts of analyte polynucleotides are used as calibration standards, it is possible to determine the amount of analyte present in a test sample by comparing the measured time-of-emergence with the standard plot.

The fact that the amplification reaction used in the below-described procedures operated at constant temperature and without interruption for a separate detection step, so that amplification and detection took place simultaneously, imposed strict requirements on the molecular beacons. More specifically, success in the procedure required that the molecular beacon bind amplicon without inhibiting subsequent use of the amplicon as a template in the exponential amplification mechanism. Indeed, the finding that an amplification reaction could proceed efficiently in the presence of a molecular beacon indicated that interaction of the probe with its target did not irreversibly inhibit or poison the amplification reaction.

Example 7 describes procedures wherein molecular beacon probes, each labeled with an interactive fluorophore/quencher pair, were used for monitoring time-dependent amplicon production in TMA reactions. Although the molecular beacons described in this Example hybridized to only one strand of the amplified nucleic acid product, complementary probe sequences also would be expected to hybridize to the opposite nucleic acid strand, and so fall within the scope of the invention.

EXAMPLE 7

Real-Time Monitoring of Amplicon Production

Molecular beacons having binding specificity for the different WNV amplicons were synthesized by standard solid-phase phosphite triester chemistry using 3' quencher-linked controlled pore glass (CPG) and 5' fluorophore-labeled phosphoramidite on a Perkin-Elmer (Foster City, Calif.) EXPEDITE model 8909 automated synthesizer. Fluorescein was used as the fluorophore, and DABCYL was used as the quencher for construction of the molecular beacons. All of the molecular beacons were constructed using 2'-methoxy nucleotide analogs. The CPG and phosphoramidite reagents were purchased from Glen Research Corporation (Sterling, Va.). Following synthesis, the probes were deprotected and cleaved from the solid support matrix by treatment with concentrated ammonium hydroxide (30%) for two hours at 60° C. Next, the probes were purified using polyacrylamide gel electrophoresis followed by HPLC using standard procedures that will be familiar to those having an ordinary level of skill in the art.

The nucleic acid targets used in the real-time amplification procedures were in vitro synthesized RNA transcripts of known concentration. The three in vitro synthesized WNV targets (a 5' non-coding region target, a 3000 region target, and a 3' non-coding region target) contained portions of the WNV genome that included sequences corresponding to, or complementary to each of the primers. Molecular beacons were used at a level of about 0.2 pmoles/μl (4 pmoles/reaction). Reactions for amplifying WNV nucleic acids were conducted using from as low as $1.5 \times 10^1$ template copies/reaction up to as high as $5 \times 10^9$ template copies/reaction.

Tubes containing 15 μl of a buffered solution that included salts and reagents essentially as described under Example 2, a target polynucleotide, and a molecular beacon were first overlaid with 15 μl of inert oil to prevent evaporation. The tubes were then incubated in a dry heat block for 10 minutes at 60° C. to facilitate primer annealing. Primers for amplifying the 5' non-coding region of the WNV target had the target-complementary sequences of SEQ ID NO:28 (which was contained within the sequence of the SEQ ID NO:40 promoter-primer) and SEQ ID NO:10. Primers for amplifying the 3000 region of the WNV target had the target-complementary sequences of SEQ ID NO:53 (which was contained within the sequence of the promoter-primer of SEQ ID NO:56) and SEQ ID NO:47. Primers for amplifying the 3' non-coding region of the WNV target had the target-complementary sequences of SEQ ID NO:76 (which was contained within the sequence of the promoter-primer of SEQ ID NO:85) and both SEQ ID NO:64 and SEQ ID NO:68. Following the 60° C. incubation step, tubes were transferred to a 42° C. heat block and then incubated for 10 minutes. Five-microliter aliquots of an enzyme reagent that included both MMLV reverse transcriptase and T7 RNA polymerase enzymes were added to each of the tubes using a repeat pipettor. Tubes were vortexed briefly and then transferred to a ROTORGENE-2000 (Corbett Research; Sydney, Australia) rotor that had been pre-warmed to 42° C. Amplification reactions were carried out at 42° C., fluorescence readings were taken every 30 seconds, and the results analyzed in real-time using standard software that was bundled with the ROTOR-GENE-2000 instrument.

Amplification in the 5' Non-Complementary Region

Table 21 presents the WNV target-complementary sequences contained in the loop portions of molecular beacons that were used for monitoring production of amplicons corresponding to the 5' non-coding region. Notably, the ninth position (occupied by an A residue) of the target-complementary loop sequence of SEQ ID NO:158 was mismatched to the amplicon product of the Ugandan strain of West Nile virus. All of the WNV-specific molecular beacons used in the procedure had target-complementary sequences that included 13-15 contiguous nucleotides contained within the sequences of SEQ ID NO:93 and SEQ ID NO:95, allowing for the presence of RNA and DNA equivalents. The target-complementary sequences presented in Table 21 were independently incorporated into the loop regions of molecular beacons.

TABLE 21

Target-Complementary Sequences of WNV-Specific Molecular Beacons (5' Non-Coding Region)

| Sequence | SEQ ID NO: |
|---|---|
| GUCAAUAUGCUAAAA | SEQ ID NO: 154 |
| GUCAAUAUGCUAAA | SEQ ID NO: 155 |
| UGUCAAUAUGCUAAA | SEQ ID NO: 156 |
| GAGCCGGGCUGUC | SEQ ID NO: 157 |
| AAACGCGGAAUGCCC | SEQ ID NO: 158 |

The complete sequences of molecular beacons that contained the WNV-complementary sequences presented in Table 21 appear in Table 22. With the exception of SEQ ID NO:162, each of the molecular beacons included a 5'CCGAG arm sequence, and a 3' CUCGG arm sequence appended to a WNV target-complementary sequence that appears in Table 21. The molecular beacon having the sequence of SEQ ID NO:162 included a 5' GGCAC arm sequence and a 3' GUGCC arm sequence appended to the loop portion of the probe. Notably, the loop portion of the molecular beacon having the sequence of SEQ ID NO:161 included a WNV target-complementary sequence and a single C residue appended to the 3I thereof, which was not complementary to the WNV target. In all instances the WNV-complementary sequences were positioned as loop regions within the molecular beacon structures. Thus, the last position (occupied by a C residue) of the loop sequence of the molecular beacon having the sequence of SEQ ID NO:161 was mismatched to the amplicon target sequence, and the ninth position of the loop sequence (occupied by an A residue) in the molecular beacon having the sequence of SEQ ID NO:163 was mismatched to the amplicon product of the Ugandan strain of West Nile virus. Each of the molecular beacons used in the procedure included a fluorescein fluorophore at its 5'-end, and a DABCYL quencher moiety at its 3'-end. Sequences corresponding to complementary arm structures are represented in Table 22 by underlining.

TABLE 22

Complete Sequences of WNV-Specific Molecular Beacons (5' Non-Coding Region)

| Sequence | SEQ ID NO: |
|---|---|
| CCGAG-GUCAAUAUGCUAAAA-CUCGG | SEQ ID NO: 159 |
| CCGAG-GUCAAUAUGCUAAA-CUCGG | SEQ ID NO: 160 |
| CCGAG-UGUCAAUAUGCUAAAC-CUCGG | SEQ ID NO: 161 |
| GGCAC-GAGCCGGGCUGUC-GUGCC | SEQ ID NO: 162 |
| CCGAG-AAACGCGGAAUGCCC-CUCGG | SEQ ID NO: 163 |

The results presented in Tables 23-25 confirmed that amplification reactions which included one of the WNV-specific molecular beacons desirably produced a fluorescent signal that increased with time until reaching a threshold level of detectability. Because different amounts of WNV template were used for testing the various probes in different procedures, the results of these procedures are presented in separate tables under which similar target amounts are grouped. All results were based on reactions that were conducted in duplicate or triplicate. With the exception of a single molecular beacon tested in this procedure (data not shown), each of the probes gave at least some level of time-dependent analyte detection. There was no attempt made to verify the integrity of the fluorescent labeling or probe synthesis in the case of the nonfunctional probe, and so the reason this probe did not give good results was not determined.

Significantly, the different molecular beacons tested in the procedure behaved somewhat differently in the real-time assay format. For example, reactions that included a molecular beacon having the target-complementary sequence of SEQ ID NO:155 gave exceedingly rapid detection of high target numbers and a strong linear relationship between the fluorescent signal and target amount on a logarithmic plot over the full range of input target levels tested (see FIG. 3). Coefficients of variation (CVs) for the time-of-emergence readings obtained using this probe (see Table 23) were 3.3% or less, thereby indicating very high levels of precision among the data points. Reactions that included a molecular beacon having the target-complementary sequence of SEQ ID NO:158 exhibited somewhat slower detection kinetics, but advantageously were capable of distinguishing low target levels from each other (see Table 24). These characteristics of the probes were reproduced when side-by-side reactions were conducted using molecular beacons containing the target-complementary sequences of SEQ ID NO:155 and SEQ ID NO:158. As indicated in Table 24, 32.2 minutes distinguished the time-of-emergence for reactions that included 15 and $1.5 \times 10^7$ copies of the WNV template, and fully 10.7 minutes distinguished the time-of-emergence for reactions that included 15 and 150 copies of the WNV template when using the molecular beacon containing the WNV-complementary sequence of SEQ ID NO:158. It should be apparent that the slope of the line relating target copy number and time-of-emergence using this probe was particularly advantageous at the low target level range. Reactions that included a molecular beacon having the target-complementary sequence of SEQ ID NO:157 yielded a substantially linear relationship between input target copy number and time-of-emergence, but exhibited a slope that was somewhat more shallow when compared with the probe that included the target-complementary sequence of SEQ ID NO:158. Reactions that included a molecular beacon having the target-complementary sequence of SEQ ID NO:156 were carried out using levels of WNV target as low as about 4 copies reaction (see Table 25), and exhibited a strong, although again somewhat shallow linear relationship between measured time-of-emergence and the target copy number in the range of $4-4.23 \times 10^3$ on a plot such as the one illustrated in FIG. 3. Indeed, a difference of nearly 6 minutes distinguished the time-of-emergence measurements for reactions conducted at these extremes when using a probe comprising the target-complementary sequence of SEQ ID NO:156.

TABLE 23

Measured Time-of-Emergence During Real-Time Amplification

| WNV Target | Time-of-Emergence Measured Using Molecular Beacons Containing Different Target-Complementary Sequences (minutes) | |
| --- | --- | --- |
| copies/rxn | SEQ ID NO: 154 | SEQ ID NO: 155 |
| $5 \times 10^9$ | 9.0 | 5.9 |
| $5 \times 10^8$ | 10.9 | 8.5 |
| $5 \times 10^7$ | 12.2 | 10.5 |
| $5 \times 10^6$ | NT | 13.0 |
| $5 \times 10^5$ | NT | 15.2 |
| $5 \times 10^4$ | NT | 17.2 |
| $5 \times 10^3$ | NT | 19.5 |
| $5 \times 10^2$ | NT | 22.0 |
| $5 \times 10^1$ | NT | 25.3 |

"NT" = not tested
"ND" = not detected

TABLE 24

Measured Time-of-Emergence During Real-Time Amplification

| WNV Target | Time-of-Emergence Measured Using Molecular Beacons Containing Different Target-Complementary Sequences (minutes) | |
| --- | --- | --- |
| copies/rxn | SEQ ID NO: 157 | SEQ ID NO: 158 |
| $1.5 \times 10^7$ | 27.67 | 28.73 |
| $1.5 \times 10^6$ | 33.43 | 34.61 |
| $1.5 \times 10^5$ | 38.3 | 40.54 |
| $1.5 \times 10^4$ | 41.27 | 45.45 |
| $1.5 \times 10^3$ | 44.59 | 47.96 |
| $1.5 \times 10^2$ | 46.26 | 50.3 |
| $1.5 \times 10^1$ | 52.34 | 60.97 |

"NT" = not tested
"ND" = not detected

TABLE 25

Measured Time-of-Emergence During Real-Time Amplification

| WNV Target copies/rxn | Time-of-Emergence Measured Using Molecular Beacon Containing the Target-Complementary Sequence of SEQ ID NO: 156 (minutes) |
| --- | --- |
| $4.23 \times 10^4$ | 37.65 |
| $4.23 \times 10^3$ | 43.02 |
| $4.23 \times 10^2$ | 45.38 |
| $4.2 \times 10^1$ | 46.68 |
| $4 \times 10^0$ | 48.9 |

"NT" = not tested
"ND" = not detected

Amplification in the 3000 Region

Table 26 presents the WNV target-complementary sequences contained in the loop portions of molecular beacons that were used for monitoring production of amplicons corresponding to the 3000 region. All of the WNV-specific molecular beacons had target-complementary sequences that included 10-20 contiguous bases contained in SEQ ID NO:99, allowing for the presence of nucleotide analogs and RNA and DNA equivalents. The target-complementary sequences presented in Table 26 were independently incorporated into the loop regions of molecular beacons.

TABLE 26

Target-Complementary Sequences of WNV-Specific Molecular Beacons (3000 Region)

| Sequence | SEQ ID NO: |
| --- | --- |
| GGUCCUUCGCAAGAGG | SEQ ID NO: 164 |
| GGUCCUUCGCAAGAGGU | SEQ ID NO: 165 |
| GGUCCUUCGC | SEQ ID NO: 166 |
| AGGUCCUUCGCAAGAGGU | SEQ ID NO: 167 |
| GGUCCUUCGCAAGAGGUG | SEQ ID NO: 168 |
| GGUCCUUCGCAAGAGGUGG | SEQ ID NO: 169 |
| AGGUCCUUCGCAAGAGGUGG | SEQ ID NO: 170 |

The complete sequences of molecular beacons that contained the WNV-complementary sequences presented in Table 26 appear in Table 27. Each of the molecular beacons included a 5' CCGAG arm sequence, and a 3' CUCGG arm sequence appended to its WNV target-complementary sequence. Additionally, each of the molecular beacons used in the procedure included a fluorescein fluorophore at its 5'-end, and a DABCYL quencher moiety at its 3'-end. Sequences corresponding to complementary arm structures are represented in Table 27 by underlining.

TABLE 27

Complete Sequences of WNV-Specific Molecular Beacons (3000 Region)

| Sequence | SEQ ID NO: |
|---|---|
| CCGAG-GGUCCUUCGCAAGAGG-CUCGG | SEQ ID NO: 171 |
| CCGAG-GGUCCUUCGCAAGAGGU-CUCCG | SEQ ID NO: 172 |
| CCGAG-GGUCCUUCGC-CUCGG | SEQ ID NO: 173 |
| CCGAG-AGGUCCUUCGCAAGAGGU-CUCGG | SEQ ID NO: 174 |
| CCGAG-GGUCCUUCGCAAGAGGUG-CUCGG | SEQ ID NO: 175 |
| CCGAG-GGUCCUUCGCAAGAGGUGG-CUCGG | SEQ ID NO: 176 |
| CCGAG-AGGUCCUUCGCAAGAGGUGG-CUCGG | SEQ ID NO: 177 |

The results presented in Table 28 confirmed that amplification reactions which included one of the WNV-specific molecular beacons desirably produced a fluorescent signal that increased with time until reaching a threshold level of detectability. Again, the different molecular beacons behaved somewhat differently in the real-time assay format. For example, reactions that included a molecular beacon having the target-complementary sequence of SEQ ID NO:167 gave extraordinarily rapid detection kinetics and a strong linear relationship between the fluorescent signal and target amount on a logarithmic plot over the full range of input target levels tested. Coefficients of variation (CVs) for the time-of-emergence readings obtained using this probe were 1.8% or less, thereby indicating very high levels of precision among the data points. Reactions that included a molecular beacon having the target-complementary sequence of SEQ ID NO:165 exhibited different response characteristics that were somewhat less linear over the full range of target input levels tested. However, it was found that conventional curve-fitting of the numerical results obtained using this probe yielded a curve having an $R^2$ value of greater than 0.99 with a slope that was substantially greater at low levels of input target when compared with high levels of input target. This advantageously permits more accurate quantitation of small differences between low target copy numbers.

TABLE 28

Measured Time-of-Emergence During Real-Time Amplification

| WNV Target | Time-of-Emergence Measured Using Molecular Beacons Containing Different Target-Complementary Sequences (minutes) SEQ ID NOs: | | | | | | |
|---|---|---|---|---|---|---|---|
| copies/rxn | 164 | 165 | 166 | 167 | 168 | 169 | 170 |
| $5 \times 10^9$ | NT | NT | NT | NT | NT | NT | NT |
| $5 \times 10^8$ | 10.9 | NT | 6.4 | NT | NT | NT | NT |
| $5 \times 10^7$ | NT | NT | NT | NT | NT | NT | NT |
| $5 \times 10^6$ | NT | 7.8 | NT | 3.6 | 7.4 | 6.7 | 7.2 |
| $5 \times 10^5$ | NT | 9.3 | NT | 4.9 | 8.8 | 8.1 | 8.5 |
| $5 \times 10^4$ | NT | 11.0 | NT | 6.3 | 10.7 | 9.7 | 10.4 |
| $5 \times 10^3$ | NT | 13.2 | NT | 7.9 | 12.2 | 11.7 | 12.3 |
| $5 \times 10^2$ | NT | 16.7 | NT | 9.6 | 14.2 | 13.6 | 14.0 |
| $5 \times 10^1$ | NT | ND | NT | 11.1 | 17.7 | 16.3 | 16.6 |

"NT" = not tested
"ND" = not detected

Amplification in the 31 Non-Coding Region

Table 29 presents the WNV target-complementary sequences contained in the loop portions of molecular beacons that were used for monitoring production of amplicons corresponding to the 31 non-coding region. The target-complementary sequences contained within the molecular beacons tested in this procedure included 12-18 contiguous nucleotides contained within the sequence of SEQ ID NO:101, more preferably within the sequence of SEQ ID NO:102, or still more preferably within the sequence of SEQ ID NO:103 or within the sequence of TAGACGGTGCTGC-CTGCG (SEQ ID NO:178), allowing for the presence of nucleotide analogs and RNA and DNA equivalents. The target-complementary sequences presented in Table 29 were independently incorporated into the loop regions of molecular beacons.

TABLE 29

Target-Complementary Sequences of WNV-Specific Molecular Beacons (3' Non-Coding Region)

| Sequence | SEQ ID NO: |
|---|---|
| CGGUGCUGCCUGCG | SEQ ID NO: 179 |
| UAGACGGUGCUG | SEQ ID NO: 180 |
| UAGACGGUGCUGCCUGCG | SEQ ID NO: 181 |
| UGAACAAAGCCGCGAAGU | SEQ ID NO: 182 |
| CUCAACCCCAGGAGGAC | SEQ ID NO: 183 |

The complete sequences of molecular beacons that contained the WNV-complementary loop sequences presented in Table 29 appear in Table 30. Each of the molecular beacons included a 5' CCGAG arm sequence, and a 3' CUCGG arm sequence appended to its WNV target-complementary sequence. Additionally, each of the molecular beacons used in the procedure included a fluorescein fluorophore at its 5'-end, and a DABCYL quencher moiety at its 3'-end.

TABLE 30

Complete Sequences of WNV-Specific Molecular Beacons (3' Non-Coding Region)

| Sequence | SEQ ID NO: |
|---|---|
| <u>CCGAG</u>-CGGUGCUGCCUGCG-<u>CUCGG</u> | SEQ ID NO: 184 |
| <u>CCGAG</u>-UAGACGGUGCUG-<u>CUCGG</u> | SEQ ID NO: 185 |
| <u>CCGAG</u>-UAGACGGUGCUGCCUGCG-<u>CUCGG</u> | SEQ ID NO: 186 |
| <u>CCGAG</u>-UGAACAAAGCCGCGAAGU-<u>CUCGG</u> | SEQ ID NO: 187 |
| <u>CCGAG</u>-CUCAACCCCAGGAGGAC-<u>CUCGG</u> | SEQ ID NO: 188 |

The results presented in Table 31 again confirmed that amplification reactions which included one of the WNV-specific molecular beacons desirably produced a fluorescent signal that increased with time until reaching a threshold level of detectability. Notably, some of the results presented in Table 31 were obtained in different experiments. Nonetheless, it should be clear that some of the probes, such as the one that included the target-complementary sequence of SEQ ID NO:182, advantageously detected the WNV target with rapid kinetics, while other probes, such as the one that included the target-complementary sequence of SEQ ID NO:179, exhibited slower detection kinetics. Each species of probe will be useful in a different particular application.

TABLE 31

Measured Time-of-Emergence During Real-Time Amplification

| WNV Target | Time-of-Emergence Measured Using Molecular Beacons Containing Different Target-Complementary Sequences (minutes) SEQ ID NOs: | | | | |
|---|---|---|---|---|---|
| copies/rxn | 179 | 180 | 181 | 182 | 183 |
| $5 \times 10^9$ | 18.7 | NT | NT | 3.1 | 7.5 |
| $5 \times 10^8$ | 27.8 | 15.4 | 15.4 | 5.0 | 14.3 |
| $5 \times 10^7$ | 42.2 | NT | NT | 10.7 | ND |
| $5 \times 10^6$ | ND | NT | NT | ND | ND |
| $5 \times 10^5$ | ND | NT | NT | NT | NT |
| $5 \times 10^4$ | ND | NT | NT | NT | NT |

"NT" = not tested
"ND" = not detected

What is claimed is:

1. A method of determining the presence of a WNV (West Nile Virus) nucleic acid in a sample, said method comprising the steps of:
   (a) synthesizing a double-stranded amplification product in vitro, wherein the double-stranded WNV sequence at one terminus of said double-stranded amplification product is SEQ ID NO: 74 base-paired to the complement thereof; and
   (b) determining that said amplification product has formed as an indication of the presence of said WNV nucleic acid in said sample.

2. The method of claim 1, wherein the synthesizing step comprises synthesizing in an in vitro nucleic acid amplification reaction that comprises reverse transcribing RNA to produce cDNA.

3. The method of claim 1, wherein the synthesizing step comprises synthesizing in an in vitro nucleic acid amplification reaction that comprises extending with a DNA polymerase each of a pair of primers.

4. The method of claim 1, wherein the synthesizing step and the determining step are performed in a single reaction vessel.

5. The method of claim 1, wherein the determining step comprises detecting an optical signal.

6. A method of detecting a WNV (West Nile Virus) nucleic acid sequence synthesized in vitro, comprising the steps of:
   (a) synthesizing in an in vitro nucleic acid amplification reaction a double-stranded DNA amplification product; and
   (b) detecting with an oligonucleotide probe the WNV nucleic acid sequence in a nucleic acid strand synthesized in the in vitro nucleic acid amplification reaction, wherein the double-stranded WNV sequence at one terminus of the double-stranded DNA amplification product consists of SEQ ID NO: 74 base-paired to the complement thereof, and wherein the complement of SEQ ID NO: 74 is a template for enzymatic synthesis of nucleic acid in said in vitro nucleic acid amplification reaction.

7. The method of claim 6, wherein the in vitro nucleic acid amplification reaction of the synthesizing step comprises a pair of primers.

8. The method of claim 7, wherein the detecting step comprises detecting the WNV nucleic acid sequence while the in vitro nucleic acid amplification reaction is occurring.

9. The method of claim 8, wherein the detecting step comprises detecting by fluorimetry.

10. The method of claim 6, wherein the in vitro nucleic acid amplification reaction in the synthesizing step comprises a reverse transcriptase.

* * * * *